(12) United States Patent
Podsiadlo et al.

(10) Patent No.: US 11,325,111 B2
(45) Date of Patent: May 10, 2022

(54) CATALYSTS AND METHODS OF MAKING THE SAME

(71) Applicant: ExxonMobil Research and Engineering Company, Annandale, NJ (US)

(72) Inventors: Paul Podsiadlo, Humble, TX (US); Quanchang Li, Dayton, NJ (US); David C. Calabro, Bridgewater, NJ (US); Kiara M. Benitez, Belvidere, NJ (US); Machteld M. W. Mertens, Boortmeerbeek (BE); Scott J. Weigel, Allentown, PA (US); Doron Levin, Highland Park, NJ (US); Randall D. Partridge, Califon, NJ (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 524 days.

(21) Appl. No.: 16/212,922

(22) Filed: Dec. 7, 2018

(65) Prior Publication Data

US 2019/0105647 A1 Apr. 11, 2019

Related U.S. Application Data

(62) Division of application No. 15/179,032, filed on Jun. 10, 2016, now Pat. No. 10,195,600.

(51) Int. Cl.
| | |
|---|---|
| *B01J 31/00* | (2006.01) |
| *B01J 31/26* | (2006.01) |
| *B01J 29/40* | (2006.01) |
| *B01J 29/44* | (2006.01) |

(Continued)

(52) U.S. Cl.
CPC .............. *B01J 31/26* (2013.01); *B01J 29/40* (2013.01); *B01J 29/44* (2013.01); *B01J 29/70* (2013.01); *B01J 29/703* (2013.01); *B01J 29/7038* (2013.01); *B01J 29/7461* (2013.01); *B01J 29/7476* (2013.01); *B01J 31/125* (2013.01); *B01J 31/127* (2013.01); *B01J 35/0006* (2013.01); *B01J 37/0009* (2013.01);
(Continued)

(58) Field of Classification Search
None
See application file for complete search history.

(56) References Cited

U.S. PATENT DOCUMENTS

| 3,178,392 A | 4/1965 | Kriner |
|---|---|---|
| 3,354,078 A | 11/1967 | Miale et al. |

(Continued)

FOREIGN PATENT DOCUMENTS

| CN | 101804335 A | 8/2010 |
|---|---|---|
| CN | 101980013 A | 2/2011 |

(Continued)

OTHER PUBLICATIONS

WO-2009084936-A2—English translation (Year: 2009).*

(Continued)

*Primary Examiner* — Stefanie J Cohen

(57) ABSTRACT

Catalysts including at least one microporous material (e.g., zeolite), an organosilica material binder, and at least one catalyst metal are provided herein. Methods of making the catalysts, preferably without surfactants and processes of using the catalysts, e.g., for aromatic hydrogenation, are also provided herein.

24 Claims, 4 Drawing Sheets

(51) Int. Cl.
*B01J 29/70* (2006.01)
*B01J 29/74* (2006.01)
*B01J 31/12* (2006.01)
*C07C 5/10* (2006.01)
*B01J 35/00* (2006.01)
*B01J 37/00* (2006.01)
*C10G 45/54* (2006.01)
*C10G 45/64* (2006.01)
*C10G 47/16* (2006.01)

(52) U.S. Cl.
CPC ............... *C07C 5/10* (2013.01); *C10G 45/54* (2013.01); *C10G 45/64* (2013.01); *C10G 47/16* (2013.01); *B01J 2229/32* (2013.01); *B01J 2229/36* (2013.01); *B01J 2229/42* (2013.01); *B01J 2231/641* (2013.01); *B01J 2231/646* (2013.01)

(56) References Cited

U.S. PATENT DOCUMENTS

| | | | |
|---|---|---|---|
| 4,218,308 A | | 8/1980 | Itoh et al. |
| 4,631,267 A | * | 12/1986 | Lachman ............. B01J 37/0018 502/439 |
| 5,348,924 A | | 9/1994 | Potter et al. |
| 5,365,003 A | * | 11/1994 | Chang ..................... B01J 29/06 208/24 |
| 5,630,937 A | | 5/1997 | Betz et al. |
| 5,719,322 A | | 2/1998 | Lansbarkis et al. |
| 6,080,908 A | * | 6/2000 | Guarracino ............... A61L 9/01 604/359 |
| 7,141,306 B1 | | 11/2006 | McKee et al. |
| 7,300,905 B2 | | 11/2007 | Keefer et al. |
| 7,497,965 B2 | | 3/2009 | Wariishi et al. |
| 7,538,065 B2 | | 5/2009 | McCarthy et al. |
| 7,682,502 B2 | | 3/2010 | McCarthy et al. |
| 7,705,062 B2 | | 4/2010 | Markowitz et al. |
| 7,754,330 B2 | | 7/2010 | Hamada et al. |
| 7,767,620 B2 | | 8/2010 | Whitnall et al. |
| 7,902,414 B2 | | 3/2011 | Ou et al. |
| 7,947,799 B2 | | 5/2011 | Manfred et al. |
| 8,110,692 B2 | | 2/2012 | Bellussi et al. |
| 8,211,498 B2 | | 7/2012 | Ku et al. |
| 8,277,600 B2 | | 10/2012 | Hamada et al. |
| 8,277,661 B2 | | 10/2012 | Sah et al. |
| 8,425,762 B2 | | 4/2013 | McCarthy et al. |
| 8,441,006 B2 | | 5/2013 | Michalak et al. |
| 8,470,074 B2 | | 6/2013 | Baugh et al. |
| 8,507,744 B2 | | 8/2013 | Hagemeister et al. |
| 8,545,694 B2 | | 10/2013 | McCarthy et al. |
| 8,562,856 B2 | | 10/2013 | Giannantonio et al. |
| 8,568,520 B2 | | 10/2013 | Ohashi et al. |
| 8,598,070 B1 | | 12/2013 | Baugh et al. |
| 8,598,071 B1 | | 12/2013 | Baugh et al. |
| 8,809,561 B2 | | 8/2014 | Bellussi et al. |
| 9,181,282 B2 | | 11/2015 | Ide et al. |
| 9,795,944 B2 | * | 10/2017 | Kamimura ............. H01M 4/625 |
| 2001/0053340 A1 | * | 12/2001 | Noda .................... B01J 37/0244 423/213.2 |
| 2003/0188991 A1 | | 10/2003 | Shan et al. |
| 2005/0093189 A1 | | 5/2005 | Vo |
| 2006/0058565 A1 | | 3/2006 | De Wild |
| 2006/0070917 A1 | | 4/2006 | McCarthy et al. |
| 2007/0003492 A1 | | 1/2007 | Kitahata et al. |
| 2007/0034992 A1 | | 2/2007 | Wariishi et al. |
| 2007/0054136 A1 | | 3/2007 | Takahashi et al. |
| 2007/0112242 A1 | | 5/2007 | Edmiston |
| 2007/0173401 A1 | | 7/2007 | Landskron et al. |
| 2009/0130412 A1 | | 5/2009 | Hatton et al. |
| 2009/0215612 A1 | | 8/2009 | McCarthy et al. |
| 2009/0294922 A1 | | 12/2009 | Hamada et al. |
| 2010/0155302 A1 | | 6/2010 | Kaminsky et al. |
| 2010/0233482 A1 | | 9/2010 | Hamada et al. |
| 2011/0139685 A1 | | 6/2011 | McCarthy et al. |
| 2011/0190115 A1 | | 8/2011 | Ciriminna et al. |
| 2012/0059181 A1 | * | 3/2012 | Bellussi .................. C01B 37/00 556/10 |
| 2012/0160742 A1 | | 6/2012 | Sohn et al. |
| 2013/0075876 A1 | | 3/2013 | Goethals et al. |
| 2013/0078172 A1 | | 3/2013 | Bingbing et al. |
| 2013/0249049 A1 | | 9/2013 | Michalak et al. |
| 2014/0004358 A1 | | 1/2014 | Blackwell et al. |
| 2014/0186246 A1 | | 7/2014 | Calabro et al. |
| 2014/0208753 A1 | | 7/2014 | Liu et al. |
| 2014/0217324 A1 | * | 8/2014 | Weston ..................... C07C 31/04 252/194 |
| 2015/0011787 A1 | | 1/2015 | Bellussi et al. |
| 2016/0167015 A1 | | 6/2016 | Podsiadlo et al. |
| 2016/0167016 A1 | | 6/2016 | Li et al. |
| 2016/0167032 A1 | | 6/2016 | Podsiadlo et al. |
| 2016/0168171 A1 | | 6/2016 | Li et al. |
| 2016/0168172 A1 | | 6/2016 | Li et al. |
| 2016/0168173 A1 | | 6/2016 | Li et al. |
| 2016/0168174 A1 | | 6/2016 | Li et al. |
| 2016/0168333 A1 | | 6/2016 | Podsiadlo et al. |
| 2016/0168484 A1 | | 6/2016 | Weigel et al. |
| 2016/0168485 A1 | | 6/2016 | Li et al. |
| 2016/0229959 A1 | | 8/2016 | Li et al. |
| 2016/0340548 A1 | | 11/2016 | Gubbels et al. |
| 2017/0306068 A1 | | 10/2017 | Holtcamp et al. |
| 2017/0313791 A1 | | 11/2017 | Mertens et al. |
| 2017/0320971 A1 | | 11/2017 | Holtcamp et al. |
| 2017/0320977 A1 | | 11/2017 | Holtcamp et al. |
| 2017/0327604 A1 | | 11/2017 | Holtcamp et al. |
| 2017/0355822 A1 | | 12/2017 | Calabro et al. |
| 2017/0355823 A1 | | 12/2017 | Peterson et al. |
| 2018/0142066 A1 | | 5/2018 | Falkowski et al. |

FOREIGN PATENT DOCUMENTS

| | | | | |
|---|---|---|---|---|
| CN | 102052713 A | | 5/2011 | |
| CN | 102643429 A | | 8/2012 | |
| CN | 103495340 A | | 1/2014 | |
| CN | 103613975 A | | 3/2014 | |
| CN | 104117343 A | | 10/2014 | |
| CN | 103157362 A | | 6/2016 | |
| EP | 0987220 A1 | * | 3/2000 | ............ C01B 33/20 |
| EP | 1995214 A2 | | 11/2008 | |
| JP | 10503419 A | | 3/1998 | |
| JP | H10151343 A | | 6/1998 | |
| JP | H11295284 A | | 10/1999 | |
| JP | 2003167233 A | | 6/2003 | |
| JP | 2006083311 A | | 3/2006 | |
| JP | 2006095512 A | | 4/2006 | |
| JP | 2007070520 A | | 3/2007 | |
| JP | 2007238761 A | | 9/2007 | |
| JP | 2008045060 A | | 2/2008 | |
| JP | 2008062138 A | | 3/2008 | |
| JP | 2010100492 A | | 5/2010 | |
| JP | 2011025201 A | | 2/2011 | |
| JP | 2012149138 A | | 8/2012 | |
| JP | 2014057941 A | | 4/2014 | |
| JP | 5544672 B1 | | 7/2014 | |
| RU | 2291878 C1 | | 1/2007 | |
| WO | 199603360 A1 | | 2/1996 | |
| WO | 9610537 A1 | | 4/1996 | |
| WO | 2006032140 A1 | | 3/2006 | |
| WO | 2007081212 A1 | | 7/2007 | |
| WO | WO-2009084936 A2 | * | 7/2009 | ........ B01J 20/28097 |
| WO | 2011145933 A1 | | 11/2011 | |
| WO | 2013093022 A1 | | 6/2013 | |
| WO | 2014040512 A1 | | 1/2014 | |
| WO | 2014090757 A1 | | 6/2014 | |
| WO | 2015100198 A1 | | 7/2015 | |
| WO | 2016094784 A1 | | 6/2016 | |
| WO | 2016094803 A1 | | 6/2016 | |

OTHER PUBLICATIONS

International Search Report and Written Opinion PCT/US2016/036933 dated Apr. 12, 2017.

(56) References Cited

OTHER PUBLICATIONS

Landskron et al., "Periodic Mesoporous Organosilicas Containing Interconnected [Si(CH2)]3 Rings", Science, Oct. 10, 2003, pp. 266-269, vol. 302.
Wu et al., "Hydrocarbon Adsorption Characterization of Some High Silica Zeolites", New Developments in Zeolite Science Technology, Proceeding of the 7th International Zeolite Conference, Studies in Surface Science and Catalysis, Aug. 17, 1986, pp. 547-554, Tokyo, Japan, ScienceDirect, Elsevier.
Landolt, "Method for rapid determination of adsorption properties of molecular sieves", Analytical Chemistry, Apr. 1971, pp. 613-615, vol. 43(4), ACS Publications.
Weisz et al., "Superactive crystalline aluminosilicate hydrocarbon catalysts", Journal of Catalysis, Aug. 1965, pp. 527-529, vol. 4, iss. 4, ScienceDirect, Elsevier.
Miale et al., "Catalysis by crystalline aluminosilicates", Journal of Catalysis, Oct. 1966, pp. 278-287, vol. 6. iss. 2, Science Direct, Elsevier.
Topchiev et al., "Preparation of hexa alkoxy derivatives of cyclotrimethylenesilane", Doklady Akademii Nauk SSSR, 1955, pp. 95-96. vol. 103.
Kriner, "The preparation of cyclic silicon methylene compounds", Journal of Organic Chemistry, Jun. 1964, pp. 1601-1606, vol. 29.
Kuivila et al., "Trimethylsilyl-substituted norbornenes, norbornanes, and nortricyclene", Journal of Organic Chemistry, Oct. 1964, pp. 2845-2851, vol. 29.
Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.
Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.
Melde et al., "Mesoporous Sieves with Unified Hybrid Inorganic/Organic Frameworks", Chemistry of Materials, Oct. 9, 1999, pp. 3302-3308, vol. 11.
Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.
Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.
"Vidal et al., ""Adsorption of polycyclic aromatic hydrocarbons from aqueous solutions by modified periodic mesoporous organosilica"", Journal of Colloid and Interface Science, Feb. 3, 2011, pp. 466-473, vol. 357, No. 2."
Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.
Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.
Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.
"Poli et al., ""Different Routes for Preparing Mesoporous Organosilicas Containing the Troger's Base and Their Textural and Catalytic Implications"", The Journal of Physical Chemistry C,Apr. 21, 2011, pp. 7573-7585, vol. 115, No. 15, ACS Publications."
PCT/US2015/065208 International Search Report and Written Opinion dated May 17, 2016.
PCT/US2015/065200 Partial International Search Report and Written Opinion dated May 23, 2016.
"Diaz et al., ""Hybrid organic-inorganic catalytic porous materials synthesized at neutral pH in absence of structural directing agents"",
Journal of Materials Chemistry, Jan. 1, 2009, pp. 5970-5979, vol. 19, No. 33, Royal Society of Chemistry."
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2016.
Goethals et al., "Ultra-low-k cyclic carbon-bridged PMO films with a high chemical resistance", Journal of Materials Chemistry, Feb. 21, 2012, pp. 8281-8286, vol. 22.
PCT/US2015/065258 Partial International Search Report and Written Opinion dated Mar. 16, 2016.
PCT/US2015/065194 International Search Report and Written Opinion dated Mar. 29, 2016.
PCT/US2015/065191 International Search Report and Written Opinion dated Mar. 29, 2016.
PCT/US2015/065306 International Search Report and Written Opinion dated Mar. 29, 2016.
PCT/US2015/065219 International Search Report and Written Opinion dated Apr. 5, 2016.
PCT/US2015/065283 International Search Report and Written Opinion dated Apr. 6, 2016.
PCT/US2015/065199 International Search Report and Written Opinion dated Apr. 8, 2016.
PCT/US2015/065204 International Search Report and Written Opinion dated Apr. 8, 2016.
PCT/US2015/065225 International Search Report and Written Opinion dated Apr. 8, 2016.
Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.
Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.
Eliseeva et al., "Anlifoaming additive for alkaline absorption solutions for removal of carbon dioxide from synthesis gas", Khimicheskaya Promyshlennost, 1999, pp. 632-633, vol. 10.
Brondani et al., "Polyfunctional carbosilanes and organosilicon compounds. Synthesis via Grignard reactions", Tetrahedron Letters, Mar. 2, 2001, pp. 2111-2114, vol. 34.
Gilman et al., "Reactions of triphenylsilyllithium with some dichloropropenes", Journal of Organometallic Chemistry, Apr. 13, 2001, pp. 293-303, vol. 2.
Goethals, et al., "A new procedure to seal the pores of mesoporous low-k films with precondensed organosilica oligomers", Chemical Communications, 2012, pp. 2797-2799, vol. 48, No. 22, Royal Society of Chemistry.
Goethals et al., "Sealed ultra low-k organosilica films with improved electrical, mechanical and chemical properties", Journal of Materials Chemistry C, 2013, vol. 1, No. 25, Royal Society of Chemistry.
Goethals et al., "Hydrophobic high quality ring PMOs with an extremely high stability", Journal of Materials Chemistry, 2010, pp. 1709-1716, vol. 20, No. 9, Royal Society of Chemistry.
Landskron et al., "Periodic Mesoporous Organosilicas: Self-Assembly from Bridged Cyclic Silsesquioxane Precursors", Angewandte Chemie, International Edition, 2005, pp. 2107-2109, vol. 44, No. 14, Wiley-VCH Verlag GmbH & Co. KgaA.
Bahuleyan et al., "One-pot synthesis of spherical periodic mesoporous organosilica supported catalyst bearing Ni(II) α-diimine compleles for ethylene polymerization", Catalysis Communications, 2009, pp. 252-256, vol. 11.
Inagaki et al., "Novel mesoporous materials with uniform distribution of organic groups and inorganic oxide in their framework", J. Am. Chem. Soc., 1999, 121, 9611-9614.
Vidal et al., "Adsorption of polycyclic aromatic hydrocarbons from aqueous solutions by modified periodic mesoporous organosilica", J Colloid and Interface Sci., 2011, 357, 466-473.
Lemaire et al., "Design of hierarchical functional porous mixed oxides from single precursors", 10th symposium of scientific bases for the preparation of heterogeneous catalysts, 2010.

(56) References Cited

OTHER PUBLICATIONS

Chandrasekar et al., "Preparation of SBA-15 extrudates: evaluation of textural and mechanical properties", 2009, J. Porous Materials, 2009, 16, 175-183.

* cited by examiner

CATALYSTS AND METHODS OF MAKING THE SAME

This application is a divisional of application Ser. No. 15/179,032 filed 10 Jun. 2016, now U.S. Pat. No. 10,195,600, the entire contents which are hereby incorporated by reference.

FIELD OF THE INVENTION

This invention relates to a catalyst containing an organosilica material component and methods of making the catalyst.

BACKGROUND OF THE INVENTION

Porous inorganic solids have found great utility as catalysts and separation media for industrial application. In particular, mesoporous materials, such as silicas and aluminas, having a periodic arrangement of mesopores are attractive materials for use in catalysis processes due to their uniform and tunable pores, high surface areas and large pore volumes. Such mesoporous materials are known to have large specific surface areas (e.g., 1000 m$^2$/g) and large pore volumes (e.g., 1 cm$^3$/g). For these reasons, such mesoporous materials enable reactive catalysts.

For example, hydrofinishing technologies have used both base and noble metal catalysts on a mesoporous support. With noble metal catalysts, excellent color and oxidation stability can be achieved at lower pressures and temperatures with smaller reactor volumes than those required when using base metal catalysts. At higher processing temperatures, color quality is sacrificed to achieve sufficient oxidation stability. With noble metal catalysts, it is possible to get superior color stability (water-white), excellent oxidation stability, and almost complete removal of aromatics.

However, mesoporous organosilicas, which may be used as a catalyst binder, are conventionally formed by the self-assembly of the silsequioxane precursor in the presence of a structure directing agent, a porogen and/or a framework element. The precursor is hydrolysable and condenses around the structure directing agent. These materials have been referred to as Periodic Mesoporous Organosilicates (PMOs), due to the presence of periodic arrays of parallel aligned mesoscale channels. For example, Landskron, K., et al. [*Science*, 302:266-269 (2003)] report the self-assembly of 1,1,3,3,5,5 hexaethoxy-1,3,5 trisilacyclohexane [(EtO)$_2$SiCH$_2$]$_3$ in the presence of a base and the structure directing agent, cetyltrimethylammonium bromide, to form PMOs that are bridged organosilicas with a periodic mesoporous framework, which consist of SiO$_3$R or SiO$_2$R$_2$ building blocks, where R is a bridging organic group. In PMOs, the organic groups can be homogenously distributed in the pore walls. U.S. Patent Application Publiaction No. 2012/0059181 reports the preparation of a crystalline hybrid organic-inorganic silicate formed from 1,1,3,3,5,5 hexaethoxy-1,3,5 trisilacyclohexane in the presence of NaAlO$_2$ and base. U.S. Patent Application Publication No. 2007/003492 reports preparation of a composition formed from 1,1,3,3,5,5 hexaethoxy-1,3,5 trisilacyclohexane in the presence of propylene glycol monomethyl ether.

However, the use of a structure directing agent, such as a surfactant, in the preparation of an organosilica material, requires a complicated, energy intensive process to eliminate the structure directing agent at the end of the preparation process. For example, calcining may be required as well as wastewater disposal steps and associated costs to dispose of the structure directing agent. This limits the ability to scale-up the process for industrial applications.

Therefore, there is a need for improved catalysts and/or processes for making catalysts using organosilica materials that can be prepared by a method that can be practiced in the absence of a structure directing agent, a porogen or surfactant.

SUMMARY OF THE INVENTION

It has been found that catalysts comprising a microporous material (e.g., a zeolite) bound with an organosilica material with desirable pore diameter, pore volume, and surface area can be achieved. Further, such catalysts can be successfully prepared without the need for a structure directing agent, a porogen or surfactant.

Thus, in one aspect, embodiments of the invention provide a method of making a catalyst. The method comprising: a) adding at least one compound into an aqueous mixture that contains essentially no structure directing agent and/or porogen to form a solution, wherein the at least one compound is selected from the group consisting of: (i) a compound of Formula [Z$^1$Z$^2$SiCH$_2$]$_3$ (Ia), wherein each Z$^1$ represents a C$_1$-C$_4$ alkoxy group and each Z$^2$ represents a C$_1$-C$_4$ alkoxy group or a C$_1$-C$_4$ alkyl group; and (ii) a cyclic compound of Formula

(IIa)

wherein each R$^3$ is independently a X$^1$OX$^2$X$^3$SiX$^4$ group, wherein each X$^1$ represents a C$_1$-C$_4$ alkyl group; X$^2$ and X$^3$ each independently represent a C$_1$-C$_4$ alkyl group, or a C$_1$-C$_4$ alkoxy group; and each X$^4$ represents a C$_1$-C$_8$ alkylene group bonded to a nitrogen atom of the cyclic compound; (b) mixing at least one microporous material with the solution to form a pre-product; (c) shaping the pre-product to form catalyst particles; (d) curing the catalyst particles; (e) drying the catalyst particles, wherein the catalyst particles comprise the at least one microporous material bound with a polymer comprising independent units of at least one monomer selected from the group consisting of: (i) a monomer of Formula [Z$^{15}$Z$^{16}$SiCH$_2$]$_3$ (I), wherein each Z$^{15}$ represents a hydroxyl group, a C$_1$-C$_4$ alkoxy group or an oxygen atom bonded to a silicon atom of another monomer and each Z$^{16}$ represents a hydroxyl group, a C$_1$-C$_4$ alkoxy group, a C$_1$-C$_4$ alkyl group, or an oxygen atom bonded to a silicon atom of another monomer; and (ii) a cyclic polyurea monomer of Formula

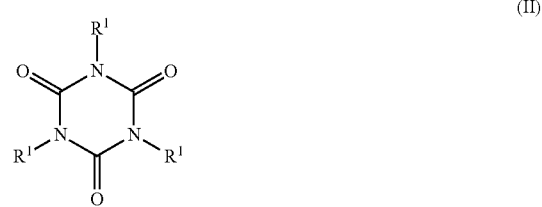

(II)

wherein each R[1] independently is a X[5]OX[6]X[7]SiX[8] group, wherein each X[5] represents a hydrogen atom, a $C_1$-$C_4$ alkyl group, or a bond to a silicon atom of another monomer unit; X[6] and X[7] each independently represent a hydroxyl group, a $C_1$-$C_4$ alkyl group, a $C_1$-$C_4$ alkoxy group, or an oxygen atom bonded to a silicon atom of another monomer unit; and each X[8] represents a $C_1$-$C_8$ alkylene group bonded to a nitrogen atom of the cyclic polyurea; and f) incorporating at least one catalyst metal within the pores of the at least one microporous material, the catalyst particles or a combination thereof.

In still another aspect, embodiments of the invention provide catalyst produced the methods described herein.

In still another aspect, embodiments of the invention provide a catalyst comprising: (i) at least one microporous material; (ii) an organosilica material binder, which is a polymer comprising independent units of a monomer selected from the group consisting of: (a) a monomer of Formula $[Z^{15}Z^{16}SiCH_2]_3$ (I), wherein each $Z^{15}$ represents a hydroxyl group, a $C_1$-$C_4$ alkoxy group or an oxygen atom bonded to a silicon atom of another monomer and each $Z^{16}$ represents a hydroxyl group, a $C_1$-$C_4$ alkoxy group, a $C_1$-$C_4$ alkyl group, or an oxygen atom bonded to a silicon atom of another monomer; and (b) a cyclic polyurea monomer of Formula

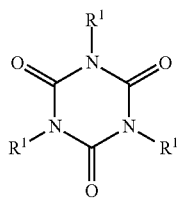

(II)

wherein each R[1] independently is a X[5]OX[6]X[7]SiX[8] group, wherein each X[5] represents a hydrogen atom, a $C_1$-$C_4$ alkyl group, or a bond to a silicon atom of another monomer unit; X[6] and X[7] each independently represent a hydroxyl group, a $C_1$-$C_4$ alkyl group, a $C_1$-$C_4$ alkoxy group, or an oxygen atom bonded to a silicon atom of another monomer unit; and each X[8] represents a $C_1$-$C_8$ alkylene group bonded to a nitrogen atom of the cyclic polyurea; and (iii) at least one catalyst metal.

Other embodiments, including particular aspects of the embodiments summarized above, will be evident from the detailed description that follows.

DETAILED DESCRIPTION OF THE INVENTION

Figure 1:
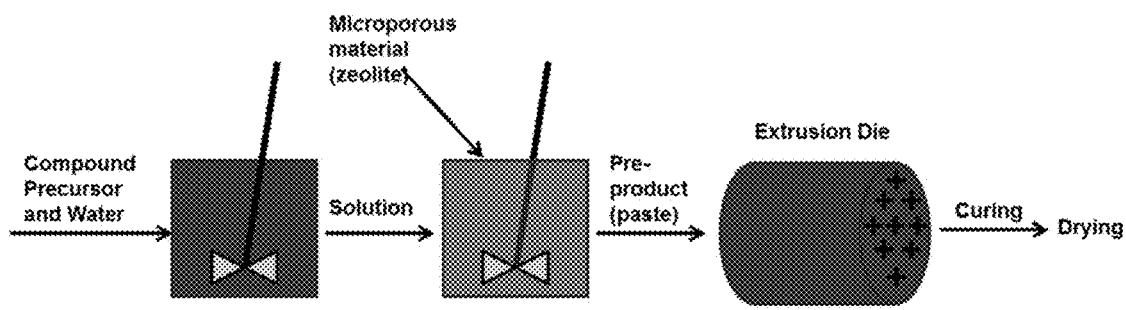
FIG. 1 illustrates a process flow diagram of an embodiment a method of producing a catalyst.

In various aspects of the invention, catalysts and methods for preparing catalysts are provided.

I. Definitions

For purposes of this invention and the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "Cn" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i.e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and "$C_4$ alkyl" refers to butyl (e.g. —$CH_2CH_2CH_2CH_3$, —$(CH_3)CHCH_2CH_3$, —$CH_2CH(CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

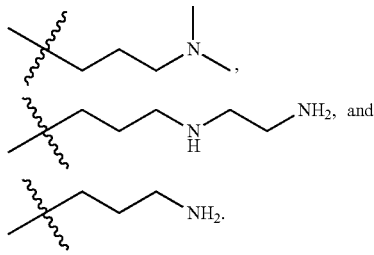

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

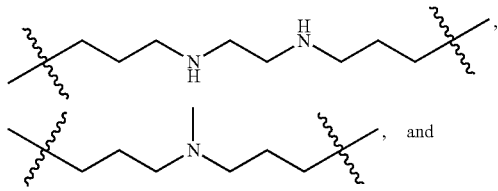

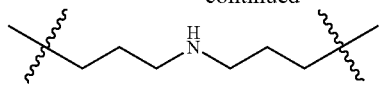

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —CH=CH—, —CH=CHCH$_2$—, —CH=CH=CH—, —$CH_2CH$=CHCH$_2$—, etc. —$CH_2CH_2$—, —$CH(CH_3)CH_2$—, —$CH_2CH_2CH_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_5$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompassses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —$CH_2CH_2$C≡CCH$_2$—, etc. —$CH_2CH_2$—, —$CH(CH_3)CH_2$—, —$CH_2CH_2CH_2$—, etc. The alkynlene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_2$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with a heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group.

As used herein, the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

II. Catalyst

The invention relates to catalysts comprising an organosilica material binder. In a first embodiment, a catalyst is provided comprising: (i) at least one microporous material; (ii) an organosilica material binder, which is a polymer comprising independent units of a monomer selected from the group consisting of: (a) a monomer of Formula $[Z^{15}Z^{16}SiCH_2]_3$ (I), wherein each $Z^{15}$ represents a hydroxyl group, a $C_1$-$C_4$ alkoxy group or an oxygen atom bonded to a silicon atom of another monomer and each $Z^{16}$ represents a hydroxyl group, a $C_1$-$C_4$ alkoxy group, a $C_1$-$C_4$ alkyl group, or an oxygen atom bonded to a silicon atom of another monomer; and (b) a cyclic polyurea monomer of Formula

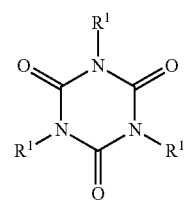

(II)

wherein each $R^1$ independently is a $X^5OX^6X^7SiX^8$ group, wherein each $X^5$ represents a hydrogen atom, a $C_1$-$C_4$ alkyl group, or a bond to a silicon atom of another monomer unit; $X^6$ and $X^7$ each independently represent a hydroxyl group, a $C_1$-$C_4$ alkyl group, a $C_1$-$C_4$ alkoxy group, or an oxygen atom bonded to a silicon atom of another monomer unit; and each $X^8$ represents a $C_1$-$C_8$ alkylene group bonded to a nitrogen atom of the cyclic polyurea; and (iii) at least one catalyst metal.

As used herein, and unless otherwise specified, "a bond to a silicon atom of another monomer" means the bond can advantageously displace a moiety (particularly an oxygen-containing moiety such as a hydroxyl, an alkoxy or the like), if present, on a silicon atom of the another monomer so there may be a bond directly to the silicon atom of the another monomer thereby connecting the two monomers, e.g., via a Si—O—Si linkage. As used herein, and unless otherwise specified, "an oxygen atom bonded to a silicon atom of another monomer" means that the oxygen atom can advantageously displace a moiety (particularly an oxygen-containing moiety such as a hydroxyl, an alkoxy or the like), if present, on a silicon atom of the another monomer so the oxygen atom may be bonded directly to the silicon atom of the another monomer thereby connecting the two monomers, e.g., via a Si—O—Si linkage. For clarity, in the aforementioned bonding scenarios, the "another monomer" can be a monomer of the same type or a monomer of a different type.

II.A. Microporous Material

Typically, the catalyst comprises at least one microporous material, which may have a framework type selected from the following group of framework types: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAG, CAN, CAS, CDO, CFI, CGF, CGS, CHA, CHI, CLO, CON, CRB, CZP, DAC, DDR, DFO, DFT, DIA, DOH, DON, EAB, EDI, EMT, EON, EPI, ERI, ESV, ETR, EUO, EZT, FAR, FAU, FER, FRA, FRL, GIS, GIU, GME, GON, GOO, HEU, IFR, THW, ISV, ITE, ITH, ITW, TWR, IWV, IWW, JBW, KFI, LAU, LCS, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, ZNI, and ZON. Particular examples of these framework types can include AEL, AFO, AHT, ATO, CAN, EUO, FER, HEU, IMF, ITH, LAU, MEL, MFI, MRE, MSE, MTT, NES, OBW, OSI, PON, RRO, SFF, SFG, STF, STI, SZR, TON, TUN and VET.

A suitable microporous material may be a zeolite with the above-mentioned framework type. Generally, the zeolite employed in the present catalyst composition can typically have a silica to alumina molar ratio of at least 20, e.g., from about 20 to about 200. Suitable zeolites can include, but are not necessarily limited to, ZSM-5, ZSM-11, ZSM-12, ZSM-22, ZSM-23, ZSM-35, ZSM-48, ZSM-50, ZSM-57, MCM-49, MCM-22, and the like, as well as intergrowths and combinations thereof. In certain embodiments, the zeolite can comprise, consist essentially of, or be ZSM-5.

Additionally or alternatively, the zeolite may be present at least partly in hydrogen form in the catalyst (e.g., HZSM-5). Depending on the conditions used to synthesize the zeolite, this may implicate converting the zeolite from, for example, the alkali (e.g., sodium) form. This can readily be achieved, e.g., by ion exchange to convert the zeolite to the ammonium form, followed by calcination in air or an inert atmosphere at a temperature from about 400° C. to about 700° C. to convert the ammonium form to the active hydrogen form. If an organic structure directing agent is used in the synthesis of the zeolite, additional calcination may be desirable to remove the organic structure directing agent.

Additionally or alternatively, the microporous material may be an aluminophosphate (i.e., ALPO). Suitable ALPOs can include, but are not necessarily limited to AlPO-11, AlPO-H2, AlPO-31 and AlPO-41.

Additionally or alternatively, the microporous material may be a silicoaluminophosphate (i.e., SAPO). Suitable SAPOs can include, but are not necessarily limited to SAPO-11, SAPO-41, and SAPO-31.

In various aspects, the at least one microporous material may be selected from the group consisting of a zeolite, a SAPO, an ALPO and a combination thereof. In particular, the at least one microporous material may selected from the group consisting of ZSM-5, ZSM-11, ZSM-12, ZSM-22, ZSM-23, ZSM-34, ZSM-35, ZSM-48, ZSM-50, ZSM-57, ZSM-58, MCM-9, MCM-41, MCM-49, MCM-22, SAPO-11, SAPO-41, AlPO-11, AlPO-H2, and AlPO-41.

A person of ordinary skill in the art knows how to make the aforementioned frameworks and molecular sieves. For example, see the references provided in the International Zeolite Association's database of zeolite structures found at www.iza-structure.org/databases.

In various aspects, the microporous material may be present in the catalyst in an amount of at least about 1.0 wt %, at least about 5.0 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt %. Additionally or alternatively, the microporous material may be present in the catalyst in an amount of at most about 95 wt %, at most about 90 wt %, at most about 80 wt %, at most about 70 wt %, at most about 60 wt %, at most about 50 wt %, at most about 40 wt %, at most about 30 wt %, at most about 20 wt %, at most about 10 wt %, ot at most about 5.0 wt %. In particular, the microporous material may be present in the catalyst in an amount of at most about 95 wt %.

Additionally or alternatively, the microporous material may be present in the catalyst in an amount of about 1.0 wt % to about 95 wt %, about 1.0 wt % to about 90 wt %, about 1.0 wt % to about 80 wt %, about 1.0 wt % to about 70 wt %, about 1.0 wt % about 60 wt %, about 1.0 wt % to about 50 wt %, about 1.0 wt % to about 40 wt %, about 1.0 wt % to about 30 wt %, about 1.0 wt % to about 20 wt %, about 1.0 wt % to about 10 wt %, about 1.0 wt % to about 5.0 wt %, about 5.0 wt % to about 95 wt %, about 5.0 wt % to about 90 wt %, about 5.0 wt % to about 80 wt %, about 5.0 wt % to about 70 wt %, about 5.0 wt % to about 60 wt %, about 5.0 wt % to about 50 wt %, about 5.0 wt % to about 40 wt %, about 5.0 wt % to about 30 wt %, about 5.0 wt % to about 20 wt %, about 5.0 wt % to about 10 wt %, about 10 wt % to about 95 wt %, about 10 wt % to about 90 wt %, about 10 wt % to about 80 wt %, about 10 wt % to about 70 wt %, about 10 wt % to about 60 wt %, about 10 wt % to about 50 wt %, about 10 wt % to about 40 wt %, about 10 wt % to about 30 wt %, about 10 wt % to about 20 wt %, about 20 wt % to about 95 wt %, about 20 wt % to about 90 wt %, about 20 wt % to about 80 wt %, about 20 wt % to about 70 wt %, about 20 wt % to about 60 wt %, about 20 wt % to about 50 wt %, about 20 wt % to about 40 wt %, about 20 wt % to about 30 wt %, about 30 wt % to about 95 wt %, about 30 wt % to about 90 wt %, about 30 wt % to about 80 wt %, about 30 wt % to about 70 wt %, about 30 wt % to about 60 wt %, about 30 wt % to about 50 wt %, about 30 wt % to about 40 wt %, about 40 wt % to about 95 wt %, about 40 wt % to about 90 wt %, about 40 wt % to about 80 wt %, about 40 wt % to about 70 wt %, about 40 wt % to about 60 wt %, about 40 wt % to about 50 wt %, about 50 wt % to about 95 wt %, about 50 wt % to about 90 wt %, about 50 wt % to about 80 wt %, about 50 wt % to about 70 wt %, about 50 wt % to about 60 wt %, about 60 wt % to about 95 wt %, about 60 wt % to about 90 wt %, about 60 wt % to about 80 wt %, about 60 wt % to about 70 wt %, about 70 wt % to about 95 wt %, about 70 wt % to about 90 wt %, about 70 wt % to about 80 wt %, 80 wt % to about 95 wt %, about 80 wt % to about 90 wt %, or about 90 wt % to about 95 wt %.

II.B. Organosilica Material Binder

The catalysts contemplated herein include the microporous material described above, which is bound with an organosilica material binder. The organosilica material binder may be a polymer comprising independent units of various monomers, which are described in detail below.

In various aspects, the organosilica material binder may be present in the catalyst in an amount of at least about 1.0 wt %, at least about 5.0 wt %, at least about 10 wt %, at least about 20 wt %, at least about 30 wt %, at least about 40 wt %, at least about 50 wt %, at least about 60 wt %, at least about 70 wt %, at least about 80 wt %, at least about 90 wt %, or at least about 95 wt %. Additionally or alternatively, the organosilica material binder may be present in the catalyst in an amount of at most about 99 wt %, at most about 95 wt %, at most about 90 wt %, at most about 80 wt %, at most about 70 wt %, at most about 60 wt %, at most about 50 wt %, at most about 40 wt %, at most about 30 wt %, at most about 20 wt %, at most about 10 wt %, or at most about 5.0 wt %.

Additionally or alternatively, the organosilica material binder may be present in the catalyst in an amount of about 1.0 wt % to about 99 wt %, about 1.0 wt % to about 95 wt %, about 1.0 wt % to about 90 wt %, about 1.0 wt % to about 80 wt %, about 1.0 wt % to about 70 wt %, about 1.0 wt % to about 60 wt %, about 1.0 wt % to about 50 wt %, about 1.0 wt % to about 40 wt %, about 1.0 wt % to about 30 wt %, about 1.0 wt % to about 20 wt %, about 1.0 wt % to about 10 wt %, about 1.0 wt % to about 5.0 wt %, about 5.0 wt % to about 99 wt %, about 5.0 wt % to about 95 wt %, about 5.0 wt % to about 90 wt %, about 5.0 wt % to about 80 wt %, about 5.0 wt % to about 70 wt %, about 5.0 wt % to about 60 wt %, about 5.0 wt % to about 50 wt %, about 5.0 wt % to about 40 wt %, about 5.0 wt % to about 30 wt %, about 5.0 wt % to about 20 wt %, about 5.0 wt % to about 10 wt %, about 10 wt % to about 99 wt %, about 10 wt % to about 95 wt %, about 10 wt % to about 90 wt %, about 10 wt % to about 80 wt %, about 10 wt % to about 70 wt %, about 10 wt % to about 60 wt %, about 10 wt % to about 50 wt %, about 10 wt % to about 40 wt %, about 10 wt % to about 30 wt %, about 10 wt % to about 20 wt %, about 20 wt % to about 99 wt %, about 20 wt % to about 95 wt %, about 20 wt % to about 90 wt %, about 20 wt % to about 80 wt %, about 20 wt % to about 70 wt %, about 20 wt % to about 60 wt %, about 20 wt % to about 50 wt %, about 20 wt % to about 40 wt %, about 20 wt % to about 30 wt %, about 30 wt % to about 99 wt %, about 30 wt % to about 95 wt %, about 30 wt % to about 90 wt %, about 30 wt % to about 80 wt %, about 30 wt % to about 70 wt %, about 30 wt % to about 60 wt %, about 30 wt % to about 50 wt %, about 30 wt % to about 40 wt %, about 40 wt % to about 99 wt %, about 40 wt % to about 95 wt %, about 40 wt % to about 90 wt %, about 40 wt % to about 80 wt %, about 40 wt % to about 70 wt %, about 40 wt % to about 60 wt %, about 40 wt % to about 50 wt %, 50 wt % to about 99 wt %, about 50 wt % to about 95 wt %, about 50 wt % to about 90 wt %, about 50 wt % to about 80 wt %, about 50 wt % to about 70 wt %, about 50 wt % to about 60 wt %, about 60 wt % to about 99 wt %, about 60 wt % to about 95 wt %, about 60 wt % to about 90 wt %, about 60 wt % to about 80 wt %, about 60 wt % to about 70 wt %, about 70 wt % to about 99 wt %, about 70 wt % to about 95 wt %, about 70 wt % to about 90 wt %, about 70 wt % to about 80 wt %, about 80 wt % to about 99 wt %, 80 wt % to about 95 wt %, about 80 wt % to about 90 wt %, about 90 wt % to about 99 wt %, about 90 wt % to about 95 wt % or 95 wt % to about 99 wt %. In particular, the organosilica material binder may be present in the catalyst in an amount of about 5.0 wt % to about 99 wt %.

1. Monomers of Formula (I)

In various embodiments, the organosilica material binder can be a polymer comprising independent units of a monomer of Formula $[Z^{15}Z^{16}SiCH_2]_3$ (I), wherein each $Z^{15}$ represents a hydroxyl group, a $C_1$-$C_4$ alkoxy group or an oxygen atom bonded to a silicon atom of another monomer and each $Z^{16}$ represents a hydroxyl group, a $C_1$-$C_4$ alkoxy group, a $C_1$-$C_4$ alkyl group, or an oxygen atom bonded to a silicon atom of another monomer In one embodiment, each $Z^{15}$ can be a hydroxyl group.

Additionally or alternatively, each $Z^{15}$ can be a $C_1$-$C_4$ alkoxy group, a $C_1$-$C_3$ alkoxy group, a $C_1$-$C_2$ alkoxy group, or methoxy.

Additionally or alternatively, each $Z^{15}$ can be an oxygen atom bonded to a silicon atom of another monomer.

Additionally or alternatively, each $Z^{15}$ can be a hydroxyl group, a $C_1$-$C_2$ alkoxy group, or an oxygen atom bonded to a silicon atom of another monomer.

Additionally or alternatively, each $Z^{16}$ can be a hydroxyl group.

Additionally or alternatively, each $Z^{16}$ can be a $C_1$-$C_4$ alkoxy group, a $C_1$-$C_3$ alkoxy group, a $C_1$-$C_2$ alkoxy group, or methoxy.

Additionally or alternatively, each $Z^{16}$ can be a $C_1$-$C_4$ alkyl group, a $C_1$-$C_3$ alkyl group, a $C_1$-$C_2$ alkyl group, or methyl.

Additionally or alternatively, each $Z^{16}$ can be an oxygen atom bonded to a silicon atom of another monomer.

Additionally or alternatively, each $Z^{16}$ can be a hydroxyl group, a $C_1$-$C_2$ alkoxy group, a $C_1$-$C_2$ alkyl group, or an oxygen atom bonded to a silicon atom of another monomer.

Additionally or alternatively, each $Z^{15}$ can be a hydroxyl group, a $C_1$-$C_2$ alkoxy group, or an oxygen atom bonded to a silicon atom of another monomer and each $Z^{16}$ can be a hydroxyl group, a $C_1$-$C_2$ alkyl group, a $C_1$-$C_2$ alkoxy group, or an oxygen atom bonded to a silicon atom of another monomer.

Additionally or alternatively, each $Z^{15}$ can be a hydroxyl group, ethoxy, or an oxygen atom bonded to a silicon atom of another siloxane and each $Z^{16}$ can be a hydroxyl group, ethoxy, or an oxygen atom bonded to a silicon atom of another monomer.

Additionally or alternatively, each $Z^{15}$ can be a hydroxyl group or an oxygen atom bonded to a silicon atom of another siloxane and each $Z^{16}$ can be a hydroxyl group, or an oxygen atom bonded to a silicon atom of another monomer.

Additionally or alternatively, each $Z^{15}$ can be a hydroxyl group, ethoxy, or an oxygen atom bonded to a silicon atom of another monomer and each $Z^{16}$ can be methyl. Additionally or alternatively, each $Z^{15}$ can be a hydroxyl group or an oxygen atom bonded to a silicon atom of another monomer and each $Z^{15}$ can be methyl.

2. Monomers of Formula (II)

Additionally or alternatively, the organosilica material binder can be a polymer comprising independent units of a monomer of Formula

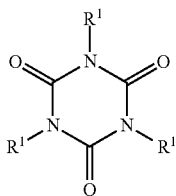

(II)

wherein each $R^1$ independently is a $X^5OX^6X^7SiX^8$ group, wherein each $X^5$ represents a hydrogen atom, a $C_1$-$C_4$ alkyl group, or a bond to a silicon atom of another monomer unit; $X^6$ and $X^7$ each independently represent a hydroxyl group, a $C_1$-$C_4$ alkyl group, a $C_1$-$C_4$ alkoxy group, or an oxygen atom bonded to a silicon atom of another monomer unit; and each $X^8$ represents a $C_1$-$C_8$ alkylene group bonded to a nitrogen atom of the cyclic polyurea In various embodiments, each $X^5$ can be a hydrogen atom.

Additionally or alternatively, each $X^5$ can be a $C_1$-$C_4$ alkyl group, a $C_1$-$C_3$ alkyl group, a $C_1$-$C_2$ alkyl group or methyl.

Additionally or alternatively, each $X^5$ can be a bond to a silicon atom of another monomer.

Additionally or alternatively, each $X^5$ can be a hydrogen atom, a $C_1$-$C_2$ alkyl group or a bond to a silicon atom of another monomer.

Additionally or alternatively, $X^6$ and $X^7$ each independently can be a hydroxyl group.

Additionally or alternatively, $X^6$ and $X^7$ each independently can be a $C_1$-$C_4$ alkyl group, a $C_1$-$C_3$ alkyl group, a $C_1$-$C_2$ alkyl group or methyl.

Additionally or alternatively, $X^6$ and $X^7$ each independently can be a $C_1$-$C_4$ alkoxy group, a $C_1$-$C_3$ alkoxy group, a $C_1$-$C_2$ alkoxy group or methoxy.

Additionally or alternatively, $X^6$ and $X^7$ each independently can be an oxygen atom bonded to a silicon atom of another monomer.

Additionally or alternatively, $X^6$ and $X^7$ each independently can be a hydroxyl group, a $C_1$-$C_2$ alkyl group, a $C_1$-$C_2$ alkoxy group, or an oxygen atom bonded to a silicon atom of another monomer.

Additionally or alternatively, each $X^5$ can be a hydrogen atom, a $C_1$-$C_2$ alkyl group or a bond to a silicon atom of another monomer; and $X^6$ and $X^7$ each independently can be a hydroxyl group, a $C_1$-$C_2$ alkyl group, a $C_1$-$C_2$ alkoxy group, or an oxygen atom bonded to a silicon atom of another monomer.

Additionally or alternatively, each $X^8$ can be a $C_1$-$C_7$ alkylene group bonded to a nitrogen atom of the cyclic polyurea, a $C_1$-$C_7$ alkylene group bonded to a nitrogen atom of the cyclic polyurea, a $C_1$-$C_6$ alkylene group bonded to a nitrogen atom of the cyclic polyurea, a $C_1$-$C_4$ alkylene group bonded to a nitrogen atom of the cyclic polyurea, a $C_1$-$C_3$ alkylene group bonded to a nitrogen atom of the cyclic polyurea, a $C_1$-$C_2$ alkylene group bonded to a nitrogen atom of the cyclic polyurea, or —$CH_2$— bonded to a nitrogen atom of the cyclic polyurea.

Additionally or alternatively, each $X^5$ can be a hydrogen atom, a $C_1$-$C_2$ alkyl group or a bond to a silicon atom of another monomer $X^6$ and $X^7$ each independently can be a hydroxyl group, a $C_1$-$C_2$ alkyl group, a $C_1$-$C_2$ alkoxy group, or an oxygen atom bonded to a silicon atom of another monomer; and $X^8$ can be a $C_1$-$C_4$ alkylene group bonded to a nitrogen atom of the cyclic polyurea.

Additionally or alternatively, each $X^5$ can be a hydrogen atom or a bond to a silicon atom of another monomer; $X^6$ and $X^7$ each independently can be a hydroxyl group, a $C_1$-$C_2$ alkyl group or an oxygen atom bonded to a silicon atom of another monomer; and Xe can be a $C_1$-$C_4$ alkylene group bonded to a nitrogen atom of the cyclic polyurea.

Additionally or alternatively, each $X^5$ can be a hydrogen atom or a bond to a silicon atom of another monomer; $X^6$ and $X^7$ each independently can be a hydroxyl group or an oxygen atom bonded to a silicon atom of another monomer; and Xe can be a $C_1$-$C_4$ alkylene group bonded to a nitrogen atom of the cyclic polyurea.

In a particular embodiment, each $X^5$ can be a hydrogen atom, methyl, or a bond to a silicon atom of another monomer; $X^6$ and $X^7$ each independently can be a hydroxyl group, methoxy or an oxygen atom bonded to a silicon atom of another monomer; and $X^8$ can be —$CH_2CH_2CH_2$— bonded to a nitrogen atom of the cyclic polyurea.

In another particular embodiment, each $X^5$ can be a hydrogen atom or a bond to a silicon atom of another monomer; $X^6$ and $X^7$ each independently can be a hydroxyl group or an oxygen atom bonded to a silicon atom of another monomer; and $X^8$ can be —$CH_2CH_2CH_2$— bonded to a nitrogen atom of the cyclic polyurea.

In another embodiment, the organosilica material binder may comprise independent units of a monomer of Formula (I) and a monomer of Formula (II).

3. Monomers of Formula (III)

In various embodiments, the organosilica material binder may further comprise another monomer in combination with independent units of Formula (I) and/or Formula (II), such as another monomer having at least one independent unit of Formula $[Z^3OZ^4SiCH_2]_3$ (III), wherein each $Z^3$ represents a hydrogen atom, a $C_1$-$C_4$ alkyl group or a bond to a silicon atom of another monomer and $Z^4$ represents a $C_1$-$C_6$ alkyl group;

In various embodiments, each $Z^3$ can be a hydrogen atom.

Additionally or alternatively, each $Z^3$ can be a $C_1$-$C_4$ alkyl group, a $C_1$-$C_3$ alkyl group, a $C_1$-$C_2$ alkyl group or methyl.

Additionally or alternatively, each $Z^3$ can be a hydrogen atom or a $C_1$-$C_2$ alkyl group.

Additionally or alternatively, each $Z^3$ can be a bond to a silicon atom of another monomer.

Additionally or alternatively, each $Z^3$ can be a hydrogen atom, a $C_1$-$C_2$ alkyl group or a bond to a silicon atom of another monomer.

Additionally or alternatively, each $Z^3$ can be a hydrogen atom, ethyl or a bond to a silicon atom of another monomer.

Additionally or alternatively, each $Z^4$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^4$ can be a methyl.

Additionally or alternatively, each $Z^3$ can be a hydrogen atom, a $C_1$-$C_2$ alkyl group or a bond to a silicon atom of another monomer and each $Z^4$ can be a $C_1$-$C_4$ alkyl group or a $C_1$-$C_2$ alkyl.

Additionally or alternatively, each $Z^3$ can be a hydrogen atom, ethyl or a bond to a silicon atom of another monomer and each $Z^4$ can be methyl.

Additionally or alternatively, each $Z^3$ can be a hydrogen atom or a bond to a silicon atom of another monomer and each $Z^4$ can be methyl.

4. Monomers of Formula (IV)

In various embodiments, the organosilica material binder may further comprise another monomer in combination with independent units of Formula (I) and/or Formula (II) and optionally independent units of Formula (III), such as another monomer having at least one independent unit of Formula $Z^5OZ^6Z^7Z^8Si$ (IV), wherein each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer.

Additionally or alternatively, each $Z^5$ can be a hydrogen atom, a $C_1$-$C_4$ alkyl group or a bond to a silicon atom of another monomer; and $Z^6$, $Z^7$ and $Z^8$ each independently can be selected from the group consisting of a hydroxyl group, a $C_1$-$C_4$ alkyl group, a $C_1$-$C_4$ alkoxy group, and an oxygen atom bonded to a silicon atom of another monomer. Additionally or alternatively, $Z^6$, $Z^7$ and $Z^8$ each independently can optionally be a nitrogen-containing $C_1$-$C_{10}$ alkyl group, a nitrogen-containing heteroaralkyl group, and/or a nitrogen-containing optionally substituted heterocycloalkyl group.

In various aspects, each $Z^5$ can be a hydrogen atom.

Additionally or alternatively, each $Z^5$ can be a $C_1$-$C_4$ alkyl group, a $C_1$-$C_3$ alkyl group, a $C_1$-$C_2$ alkyl group or methyl.

Additionally or alternatively, each $Z^5$ can be a hydrogen atom or a $C_1$-$C_2$ alkyl group.

Additionally or alternatively, each $Z^5$ can be a bond to a silicon atom of another monomer.

Additionally or alternatively, each $Z^5$ can be a hydrogen atom, a $C_1$-$C_2$ alkyl group or a bond to a silicon atom of another monomer.

Additionally or alternatively, each $Z^5$ can be a hydrogen atom, ethyl, methyl or a bond to a silicon atom of another monomer.

Additionally or alternatively, $Z^6$, $Z^7$ and $Z^8$ each independently can be a hydroxyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group.

Additionally or alternatively, $Z^6$, $Z^7$ and $Z^8$ each independently can be a $C_1$-$C_4$ alkyl group, a $C_1$-$C_3$ alkyl group, a $C_1$-$C_2$ alkyl group or methyl.

Additionally or alternatively, $Z^6$, $Z^7$ and $Z^8$ each independently can be a hydroxyl group or a $C_1$-$C_2$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be a hydroxyl group or a $C_1$-$C_2$ alkyl group.

Additionally or alternatively, $Z^6$, $Z^7$ and $Z^8$ each independently can be a $C_1$-$C_4$ alkoxy group, a $C_1$-$C_3$ alkoxy group, a $C_1$-$C_2$ alkoxy group or methoxy.

Additionally or alternatively, $Z^6$, $Z^7$ and $Z^8$ each independently can be selected from the group consisting of a hydroxyl group, a $C_1$-$C_2$ alkyl group and a $C_1$-$C_2$ alkoxy group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each can be selected from the group consisting of a hydroxyl group, a $C_1$-$C_2$ alkyl group and a $C_1$-$C_2$ alkoxy group.

Additionally or alternatively, $Z^6$, $Z^7$ and $Z^8$ each independently can optionally be a nitrogen-containing $C_1$-$C_{10}$ alkyl group, a nitrogen-containing $C_1$-$C_9$ alkyl group, a nitrogen-containing $C_1$-$C_5$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^6$, $Z^7$ and $Z^8$ each independently can be a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

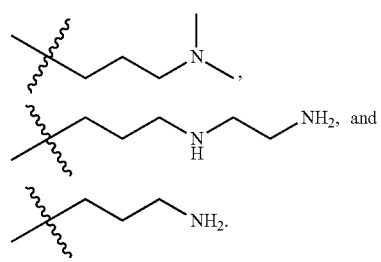

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group.

Additionally or alternatively, $Z^6$, $Z^7$ and $Z^8$ each independently can optionally be a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_5$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group and a nitrogen-containing heteroaralkyl group.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group and a nitrogen-containing heteroaralkyl group.

Additionally or alternatively, $Z^6$, $Z^7$ and $Z^8$ each independently can optionally be a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_5$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group, a nitrogen-containing heteroaralkyl group, and a nitrogen-containing optionally substituted heterocycloalkyl group.

Additionally or alternatively, $Z^6$, $Z^7$ and $Z^8$ each independently can be selected from the group consisting of a hydroxyl group, a $C_1$-$C_2$ alkyl group, a $C_1$-$C_2$ alkoxy group, and an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group and a nitrogen-containing optionally substituted heterocycloalkyl group.

Additionally or alternatively, $Z^6$, $Z^7$ and $Z^8$ each independently can be selected from the group consisting of a hydran oxygen atom bonded to a silicon atom of another monomer.

Additionally or alternatively, $Z^6$, $Z^7$ and $Z^8$ each independently can be an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing heteroaralkyl group, a nitrogen-containing optionally substituted heterocycloalkyl group and an oxygen atom bonded to a silicon atom of another monomer.

Additionally or alternatively, each $Z^5$ can be a hydrogen atom, a $C_1$-$C_2$ alkyl group or a bond to a silicon atom of another monomer; and $Z^6$, $Z^7$ and $Z^8$ each independently can be selected from the group consisting of a hydroxyl group, a $C_1$-$C_2$ alkyl group, a $C_1$-$C_2$ alkoxy group, a nitrogen-containing $C_3$-$C_{10}$ alkyl group, a nitrogen-containing $C_4$-$C_{10}$ heteroaralkyl group, a nitrogen-containing optionally substituted $C_4$-$C_{10}$ heterocycloalkyl group, and an oxygen atom bonded to a silicon atom of another monomer.

Additionally or alternatively, each $Z^5$ can be a hydrogen atom or a bond to a silicon atom of another monomer; and $Z^6$, $Z^7$ and $Z^8$ each independently can be selected from the group consisting of a hydroxyl group, a $C_1$-$C_2$ alkyl group, a nitrogen-containing $C_3$-$C_5$ alkyl group, $C_4$-$C_{10}$ heteroaralkyl group, a nitrogen-containing optionally substituted $C_4$-$C_{10}$ heterocycloalkyl group, and an oxygen atom bonded to a silicon atom of another monomer.

In a particular embodiment, each $Z^5$ can be a hydrogen atom, ethyl or a bond to a silicon atom of another monomer; and $Z^6$, $Z^7$ and $Z^8$ each independently can be selected from the group consisting of a hydroxyl group, ethoxy, and an oxygen atom bonded to a silicon atom of another monomer.

In another particular embodiment, each $Z^5$ can be a hydrogen atom, ethyl or a bond to a silicon atom of another monomer; $Z^6$ and $Z^7$ each independently can be selected from the group consisting of a hydroxyl group, ethoxy, and an oxygen atom bonded to a silicon atom of another monomer; and $Z^8$ can be methyl.

In another particular embodiment, each $Z^5$ can be a hydrogen atom, methyl or a bond to a silicon atom of another monomer; $Z^6$ and $Z^7$ each independently can be selected from the group consisting of a hydroxyl group, methoxy, and an oxygen atom bonded to a silicon atom of another monomer; and each $Z^8$ can be

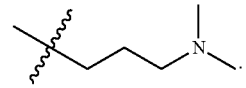 [SMILES: *CCCN(C)C]

In another particular embodiment, each $Z^5$ can be a hydrogen atom, ethyl or a bond to a silicon atom of another monomer; $Z^6$ and $Z^7$ each independently can be selected from the group consisting of a hydroxyl group, ethoxy, and an oxygen atom bonded to a silicon atom of another monomer; and each $Z^8$ can be

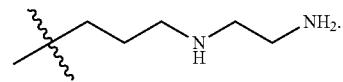 [SMILES: *CCCNCCN]

In another particular embodiment, each $Z^5$ can be a hydrogen atom, ethyl or a bond to a silicon atom of another monomer; $Z^6$ and $Z^7$ each independently can be selected from the group consisting of a hydroxyl group, ethoxy, and an oxygen atom bonded to a silicon atom of another monomer; and each $Z^8$ can be

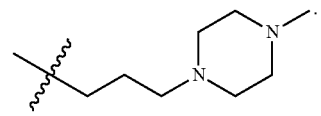 [SMILES: *CCCN1CCN(C)CC1]

In another particular embodiment, each $Z^5$ can be a hydrogen atom, ethyl or a bond to a silicon atom of another monomer; $Z^6$ and $Z^7$ each independently can be selected from the group consisting of a hydroxyl group, ethoxy, and an oxygen atom bonded to a silicon atom of another monomer; and each $Z^8$ can be

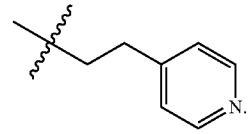 [SMILES: *CCc1ccncc1]

In another particular embodiment, each $Z^5$ can be a hydrogen atom, ethyl or a bond to a silicon atom of another monomer; $Z^6$ and $Z^7$ each independently can be selected from the group consisting of a hydroxyl group, ethoxy, and an oxygen atom bonded to a silicon atom of another monomer; and each $Z^8$ can be

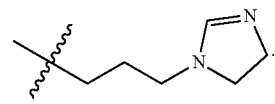 [SMILES: *CCCN1C=NCC1]

In another particular embodiment, each $Z^5$ can be a hydrogen atom, ethyl or a bond to a silicon atom of another monomer; $Z^6$ and $Z^7$ each independently can be selected from the group consisting of a hydroxyl group, ethoxy, and an oxygen atom bonded to a silicon atom of another monomer; and each $Z^8$ can be

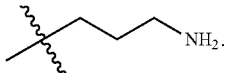

In another particular embodiment, each $Z^5$ can be a hydrogen atom, methyl, ethyl, or a bond to a silicon atom of another monomer; and $Z^6$, $Z^7$ and $Z^8$ each independently can be selected from the group consisting of a hydroxyl group, methyl, methoxy, ethoxy,

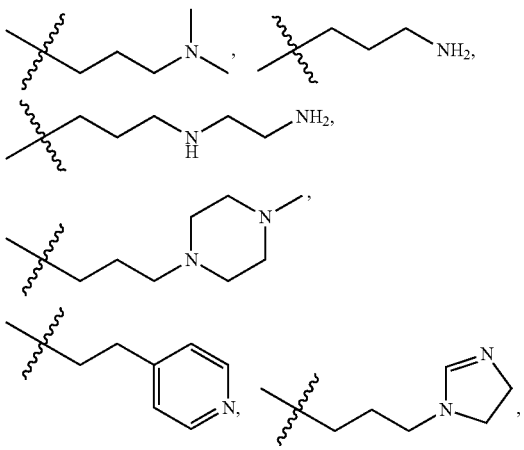

and an oxygen bonded to a silicon atom of another monomer.

5. Monomers of Formula (V)

In various embodiments, the organosilica material may further comprise another monomer in combination with independent units of Formula (I) and/or Formula (II) and optionally, independent units of Formula (III) and/or Formula (IV), such as another monomer having at least one independent unit of Formula $Z^9Z^{10}Z^{11}Si-R-SiZ^9Z^{10}Z^{11}$ (V), wherein each $Z^9$ independently can be a hydroxyl group, a $C_1$-$C_4$ alkoxy group or an oxygen atom bonded to a silicon atom of another monomer; $Z^{10}$ and $Z^{11}$ each independently can a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group.

Additionally or alternatively, each $Z^9$ independently can be a hydroxyl group, a $C_1$-$C_4$ alkoxy group or an oxygen atom bonded to a silicon atom of another monomer; $Z^{10}$ and $Z^{11}$ each independently can a hydroxyl group, a $C_1$-$C_4$ alkoxy group, a $C_1$-$C_4$ alkyl group or an oxygen atom bonded to a silicon atom of another monomer; and each R can be selected from the group consisting a $C_1$-$C_8$ alkylene group, a $C_2$-$C_8$ alkenylene group, and a $C_2$-$C_8$ alkynylene group. Additionally or alternatively, R optionally can be a nitrogen-containing $C_1$-$C_{10}$ alkylene group, an optionally substituted $C_6$-$C_{20}$ aralkyl and/or an optionally substituted $C_4$-$C_{20}$ heterocycloalkyl group.

In various aspects, each $Z^9$ can be a hydroxyl group.

Additionally or alternatively, each $Z^9$ can be a $C_1$-$C_4$ alkoxy group, a $C_1$-$C_3$ alkoxy group, a $C_1$-$C_2$ alkoxy group or methoxy.

Additionally or alternatively, each $Z^9$ can be a hydroxyl group or a $C_1$-$C_2$ alkoxy group.

Additionally or alternatively, each $Z^9$ can be an oxygen atom bonded to a silicon atom of another monomer.

Additionally or alternatively, each $Z^9$ can be a hydroxyl group, a $C_1$-$C_2$ alkoxy group or an oxygen atom bonded to a silicon atom of another monomer.

Additionally or alternatively, each $Z^9$ can be a hydroxyl group or an oxygen atom bonded to a silicon atom of another monomer.

Additionally or alternatively, $Z^{10}$ and $Z^{11}$ each independently can be a hydroxyl group.

Additionally or alternatively, $Z^{10}$ and $Z^{11}$ each independently can be a $C_1$-$C_4$ alkoxy group, a $C_1$-$C_3$ alkoxy group, a $C_1$-$C_2$ alkoxy group or methoxy.

Additionally or alternatively, $Z^{10}$ and $Z^{11}$ each independently can be a hydroxyl group or a $C_1$-$C_2$ alkoxy group.

Additionally or alternatively, $Z^{10}$ and $Z^{11}$ each independently can be a $C_1$-$C_4$ alkyl group, a $C_1$-$C_3$ alkyl group, a $C_1$-$C_2$ alkyl group or methyl.

Additionally or alternatively, $Z^{10}$ and $Z^{11}$ each independently can be a hydroxyl group, a $C_1$-$C_2$ alkoxy group, or a $C_1$-$C_2$ alkyl group.

Additionally or alternatively, $Z^{10}$ and $Z^{11}$ each independently can be an oxygen atom bonded to a silicon atom of another monomer.

Additionally or alternatively, $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer.

Additionally or alternatively, $Z^{10}$ and $Z^{11}$ each independently can be a hydroxyl group, a $C_1$-$C_2$ alkyl group, or an oxygen atom bonded to a silicon atom of another monomer.

Additionally or alternatively, each $Z^9$ can be a hydroxyl group, a $C_1$-$C_2$ alkoxy group or an oxygen atom bonded to a silicon atom of another monomer; and $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer.

Additionally or alternatively, each $Z^9$ can be a hydroxyl group, ethoxy, methoxy or an oxygen atom bonded to a silicon atom of another monomer; and $Z^{10}$ and $Z^{11}$ each independently can be a hydroxyl group, ethoxy, methyl, or an oxygen atom bonded to a silicon atom of another monomer.

Additionally or alternatively, each $Z^9$ can be a hydroxyl group or an oxygen atom bonded to a silicon atom of another monomer; and $Z^{10}$ and $Z^{11}$ each independently can be a hydroxyl group, methyl, or an oxygen atom bonded to a silicon atom of another monomer.

Additionally or alternatively, each R can be a $C_1$-$C_8$ alkylene group, a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group or —$CH_2$—.

Additionally or alternatively, each $Z^9$ can be a hydroxyl group, a $C_1$-$C_2$ alkoxy group or an oxygen atom bonded to a silicon atom of another monomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer; and each R can be a $C_1$-$C_4$ alkylene group.

Additionally or alternatively, each R can be a $C_2$-$C_8$ alkenylene group, a $C_2$-$C_7$ alkenylene group, a $C_2$-$C_6$ alkenylene group, a $C_2$-$C_5$ alkenylene group, a $C_2$-$C_4$ alkenylene group, a $C_2$-$C_3$ alkenylene group, or —HC=CH—.

Additionally or alternatively, each $Z^9$ can be a hydroxyl group, a $C_1$-$C_2$ alkoxy group or an oxygen atom bonded to a silicon atom of another monomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer; and each R can be selected from the group consisting of a $C_1$-$C_4$ alkylene group and a $C_2$-$C_4$ alkenylene group.

Additionally or alternatively, each R can be a $C_2$-$C_8$ alkynylene group, a $C_2$-$C_7$ alkynylene group, a $C_2$-$C_6$ alkynylene group, a $C_2$-$C_5$ alkynylene group, a $C_2$-$C_4$ alkynylene group, a $C_2$-$C_3$ alkynylene group, or —C≡C—.

Additionally or alternatively, each $Z^9$ can be a hydroxyl group, a $C_1$-$C_2$ alkoxy group or an oxygen atom bonded to a silicon atom of another monomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer; and each R can be selected from the group consisting of a $C_1$-$C_4$ alkylene group, a $C_2$-$C_4$ alkenylene group and a $C_2$-$C_4$ alkynylene group.

Additionally or alternatively, each R can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

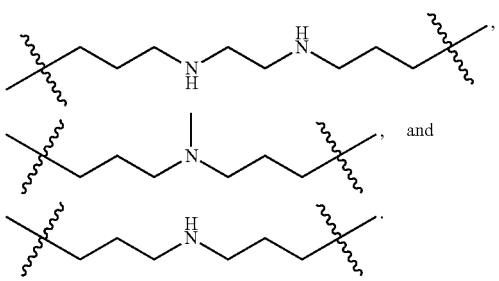

Additionally or alternatively, each $Z^9$ can be a hydroxyl group, a $C_1$-$C_2$ alkoxy group or an oxygen atom bonded to a silicon atom of another monomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer; and each R can be selected from the group consisting of a $C_1$-$C_4$ alkylene group, a $C_2$-$C_4$ alkenylene group, a $C_2$-$C_4$ alkynylene group and a nitrogen-containing $C_4$-$C_{10}$ alkylene group.

Additionally or alternatively, each R can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenylmethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another monomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group and an optionally substituted $C_6$-$C_{10}$ aralkyl.

Additionally or alternatively, each R can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^9$ can be a hydroxyl group, a $C_1$-$C_2$ alkoxy group or an oxygen atom bonded to a silicon atom of another monomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

Additionally or alternatively, each $Z^9$ can be a hydroxyl group, a $C_1$-$C_2$ alkoxy group or an oxygen atom bonded to a silicon atom of another monomer; $Z^{10}$ and $Z^{11}$ each independently can be a hydroxyl group, a $C_1$-$C_2$ alkoxy group, a $C_1$-$C_2$ alkyl group, or an oxygen atom bonded to a silicon atom of another monomer; and R can be selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{10}$ heterocycloalkyl group.

Additionally or alternatively, each $Z^9$ can be a hydroxyl group, ethoxy, methoxy or an oxygen atom bonded to a silicon atom of another monomer; $Z^{10}$ and $Z^{11}$ each independently can be a hydroxyl group, ethoxy, methoxy, methyl, or an oxygen atom bonded to a silicon atom of another monomer; and R can be selected from the group consisting of —$CH_2$—, —$CH_2CH_2$—, —HC=CH—,

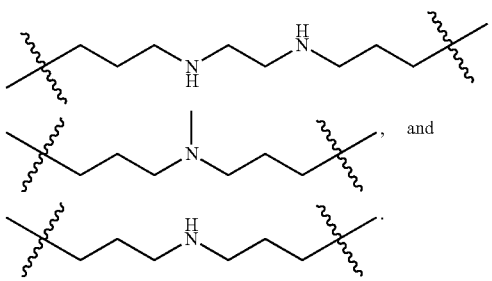

Additionally or alternatively, each $Z^9$ can be a hydroxyl group or an oxygen atom bonded to a silicon atom of another monomer; $Z^{10}$ and $Z^{11}$ each independently can be a hydroxyl group, methyl, or an oxygen atom bonded to a silicon atom of another monomer; and each R can be selected from the group consisting of —CH$_2$—, —CH$_2$CH$_2$—, —HC=CH—,

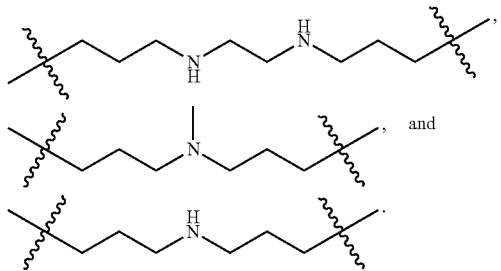

In a particular embodiment, each $Z^9$ can be a hydroxyl group, ethoxy or an oxygen atom bonded to a silicon atom of another monomer; each $Z^{10}$ can be a hydroxyl group, ethoxy, and an oxygen atom bonded to a silicon atom of another monomer; each $Z^{11}$ can be methyl; and each R can be —CH$_2$CH$_2$—.

In another particular embodiment, each $Z^9$ can be a hydroxyl group, ethoxy or an oxygen atom bonded to a silicon atom of another monomer; $Z^{10}$ and $Z^{11}$ each independently can be selected from the group consisting of a hydroxyl group, ethoxy, and an oxygen atom bonded to a silicon atom of another monomer; and R can be —CH$_2$—.

In another particular embodiment, each $Z^9$ can be a hydroxyl group, ethoxy or an oxygen atom bonded to a silicon atom of another monomer; $Z^{10}$ and $Z^{11}$ each independently can be selected from the group consisting of a hydroxyl group, ethoxy, and an oxygen atom bonded to a silicon atom of another monomer; and R can be —HC=CH—.

In another particular embodiment, each $Z^9$ can be a hydroxyl group, methoxy or an oxygen atom bonded to a silicon atom of another monomer; $Z^{10}$ and $Z^{11}$ each independently can be selected from the group consisting of a hydroxyl group, methoxy, and an oxygen atom bonded to a silicon atom of another monomer; and each

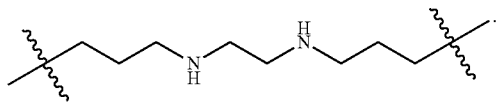 [SMILES: *CCCNCCNCCC*]

In another particular embodiment, each $Z^9$ can be a hydroxyl group, ethoxy or an oxygen atom bonded to a silicon atom of another monomer; $Z^{10}$ can be a hydroxyl group, ethoxy, and an oxygen atom bonded to a silicon atom of another monomer; $Z^{11}$ can be methyl; and each R can be

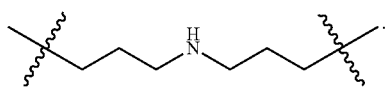 [SMILES: *CCCNCCC*]

In another particular embodiment, each $Z^9$ can be a hydroxyl group, methoxy or an oxygen atom bonded to a silicon atom of another monomer; $Z^{10}$ can be a hydroxyl group, methoxy, and an oxygen atom bonded to a silicon atom of another monomer; $Z^{11}$ can be methyl; and each R can be

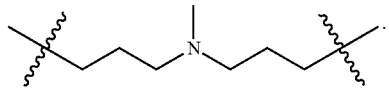 [SMILES: *CCCN(C)CCC*]

In another embodiment, the organosilica material support may comprise independent units of Formula (III) as described herein and independent units of Formula (IV) as described herein and not independent units of Formula (I) as described herein. In particular, each $Z^5$ can be a hydrogen atom, ethyl or a bond to a silicon atom of another monomer; $Z^6$, $Z^7$ and $Z^8$ each independently can be selected from the group consisting of a hydroxyl group, ethoxy, and an oxygen atom bonded to a silicon atom of another monomer and each $Z^9$ can be a hydroxyl group, ethoxy or an oxygen atom bonded to a silicon atom of another monomer; $Z^{10}$ and $Z^{11}$ each independently can be selected from the group consisting of a hydroxyl group, ethoxy, and an oxygen atom bonded to a silicon atom of another monomer; and R can be —CH$_2$—.

6. Monomers of Formula (VI)

In various embodiments, the organosilica material binder may further comprise another monomer in combination with independent units of Formula (I) and/or Formula (II) and optionally independent units of Formula (III), (IV), and/or Formula (V), such as another monomer having at least one independent unit of Formula M$^1$ (OZ$^2$)$_3$ (VI), wherein M$^1$ represents a Group 13 metal and each $Z^{12}$ independently represents a hydrogen atom, a C$_1$-C$_6$ alkyl or a bond to a silicon atom of another monomer;

Additionally or alternatively, M$^1$ can be B, Al, Ga, IN Tl, or Uut. In particular, M$^1$ can be Al or B.

Additionally or alternatively, each $Z^{12}$ can be a hydrogen atom.

Additionally or alternatively, M$^1$ can be Al or B and $Z^3$ can be a hydrogen atom.

Additionally or alternatively, each $Z^{12}$ can be a C$_1$-C$_6$ alkyl group, a C$_1$-C$_5$ alkyl group, a C$_1$-C$_4$ alkyl group, a C$_1$-C$_3$ alkyl group, a C$_1$-C$_2$ alkyl group or methyl. In particular, $Z^3$ can be methyl, ethyl, propyl or butyl.

Additionally or alternatively, M$^1$ can be Al or B and $Z^{12}$ can be a hydrogen atom, methyl, ethyl, propyl or butyl.

Additionally or alternatively, each $Z^{12}$ can be a bond to a silicon atom of another monomer.

Additionally or alternatively, M$^1$ can be Al or B and each $Z^{12}$ can be a hydrogen atom, methyl, ethyl, propyl, butyl or a bond to a silicon atom of another monomer.

Additionally or alternatively, M$^1$ can be Al or B and each $Z^{12}$ can be a hydrogen atom or a bond to a silicon atom of another monomer.

Additionally or alternatively, M$^1$ can be Al and each $Z^{12}$ can be a hydrogen atom, methyl, ethyl, propyl, butyl or a bond to a silicon atom of another monomer.

In a particular embodiment, M$^1$ can be Al and each $Z^{12}$ can be a hydrogen atom, methyl or a bond to a silicon atom of another monomer.

In another particular embodiment, M$^1$ can be Al and each $Z^{12}$ can be a hydrogen atom, ethyl or a bond to a silicon atom of another monomer.

In another particular embodiment, M$^1$ can be Al and each $Z^{12}$ can be a hydrogen atom, propyl or a bond to a silicon atom of another monomer.

In another particular embodiment, M$^1$ can be Al and each $Z^{12}$ can be a hydrogen atom, butyl or a bond to a silicon atom of another monomer.

In another particular embodiment, $M^1$ can be Al or B; and each $Z^{12}$ can be a hydrogen atom or a bond to a silicon atom of another monomer.

7. Monomers of Formula (VII)

In various embodiments, the organosilica material binder may further comprise another monomer in combination with independent units of Formula (I) and/or Formula (II) and optionally independent units Formula (III), (IV), (V) and/or Formula (VI), such as another monomer having at least one independent unit of Formula $(Z^{13}O)_2M^2$-O—Si$(OZ^4)_3$ (VI), wherein $M^2$ represents a Group 13 metal and $Z^{13}$ and $Z^{14}$ each independently represent a hydrogen atom, a $C_1$-$C_6$ alkyl group or a bond to a silicon atom of another monomer.

Additionally or alternatively, $M^2$ can be B, Al, Ga, IN Tl, or Uut. In particular, $M^2$ can be Al or B.

Additionally or alternatively, $Z^{13}$ and/or $Z^{14}$ each can be a hydrogen atom.

Additionally or alternatively, $M^2$ can be Al or B and $Z^{13}$ and/or $Z^{14}$ each can be a hydrogen atom.

Additionally or alternatively, $Z^{13}$ and/or $Z^{14}$ each can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{13}$ and/or $Z^{14}$ can be methyl, ethyl, propyl or butyl.

Additionally or alternatively, $M^2$ can be Al or B; and $Z^{13}$ and/or $Z^{14}$ each independently can be a hydrogen atom, methyl, ethyl, propyl or butyl.

Additionally or alternatively, $Z^{13}$ and/or $Z^{14}$ each can be a bond to a silicon atom of another monomer.

Additionally or alternatively, $M^2$ can be Al or B; and $Z^{13}$ and $Z^{14}$ each independently can be a hydrogen atom, methyl, ethyl, propyl, butyl or a bond to a silicon atom of another monomer.

Additionally or alternatively, $M^2$ can be Al or B; and $Z^{13}$ and $Z^{14}$ each independently can be a hydrogen atom or a bond to a silicon atom of another monomer.

Additionally or alternatively, $M^2$ can be Al; and $Z^{13}$ and $Z^{14}$ each independently can be a hydrogen atom, methyl, ethyl, propyl, butyl or a bond to a silicon atom of another monomer.

In a particular embodiment, $M^2$ can be Al; and $Z^{13}$ and $Z^{14}$ each independently can be a hydrogen atom, methyl or a bond to a silicon atom of another monomer.

In another particular embodiment, $M^2$ can be Al; and $Z^{13}$ and $Z^{14}$ each independently can be a hydrogen atom, ethyl or a bond to a silicon atom of another monomer.

In another particular embodiment, $M^2$ can be Al; and $Z^{13}$ and $Z^{14}$ each independently can be a hydrogen atom, propyl or a bond to a silicon atom of another monomer.

In another particular embodiment, $M^2$ can be Al; and $Z^{13}$ and $Z^{14}$ each independently can be a hydrogen atom, butyl or a bond to a silicon atom of another monomer.

In another particular embodiment, $M^2$ can be Al or B; and $Z^{13}$ and $Z^{14}$ each independently can be a hydrogen atom or a bond to a silicon atom of another monomer.

The organosilica material binders described herein can be characterized as described in the following sections.

8. Pore Size

The catalysts described herein may advantageously be in a mesoporous form. As indicated previously, the term mesoporous refers to solid materials having pores with a diameter within the range of from about 2 nm to about 50 nm. The average pore diameter of the catalyst can be determined, for example, using nitrogen adsorption-desorption isotherm techniques within the expertise of one of skill in the art, such as the BET (Brunauer Emmet Teller) method.

Additionally or alternatively, the catalyst can advantageously have an average pore diameter within the mesopore range of about 2.0 nm, about 2.5 nm, about 3.0 nm, about 3.5 nm, about 4.0 nm, about 4.5 nm, about 5.0 nm, about 6.0 nm, about 7.0 nm, about 7.5 nm, about 8.0 nm, about 8.5 nm, about 9 nm, about 10 nm, about 11 nm, about 13 nm, about 15 nm, about 20 nm, about 25 nm, about 30 nm, about 40 nm, about 45 nm, or about 50 nm.

Additionally or alternatively, the catalyst can have an average pore diameter of about 2.0 nm to about 50 nm, about 2.0 nm to about 40 nm, about 2.0 nm to about 30 nm, about 2.0 nm to about 25 nm, about 2.0 nm to about 20 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.5 nm, about 2.0 nm to about 8 nm, about 2.0 nm to about 7.5 nm, about 2.0 nm to about 7.0 nm, about 2.0 nm to about 6.0 nm, about 2.0 nm to about 5.0 nm, about 2.0 nm to about 4.5 nm, about 2.0 nm to about 4.0 nm, about 2.0 nm to about 3.0 nm, about 3.0 nm to about 50 nm, about 3.0 nm to about 40 nm, about 3.0 nm to about 30 nm, about 3.0 nm to about 25 nm, about 3.0 nm to about 20 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.5 nm, about 3.0 nm to about 8 nm, about 3.0 nm to about 7.5 nm, about 3.0 nm to about 7.0 nm, about 3.0 nm to about 6.0 nm, about 3.0 nm to about 5.0 nm, about 2.0 nm to about 4.5 nm, or about 3.0 nm to about 4.0 nm. In particular, the catalysts can have an average pore diameter of about 2.0 nm to about 20 nm.

9. Surface Area

The surface area of the catalyst can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method.

In various embodiments, the catalyst can have a total surface area greater than or equal to about 100 $m^2$/g, greater than or equal to about 200 $m^2$/g, greater than or equal to about 300 $m^2$/g, greater than or equal to about 400 $m^2$/g, greater than or equal to about 450 $m^2$/g, greater than or equal to about 500 $m^2$/g, greater than or equal to about 550 $m^2$/g, greater than or equal to about 600 $m^2$/g, greater than or equal to about 700 $m^2$/g, greater than or equal to about 800 $m^2$/g, greater than or equal to about 850 $m^2$/g, greater than or equal to about 900 $m^2$/g, greater than or equal to about 1,000 $m^2$/g, greater than or equal to about 1,050 $m^2$/g, greater than or equal to about 1,100 $m^2$/g, greater than or equal to about 1,150 $m^2$/g, greater than or equal to about 1,200 $m^2$/g, greater than or equal to about 1,250 $m^2$/g, greater than or equal to about 1,300 $m^2$/g, greater than or equal to about 1,400 $m^2$/g, greater than or equal to about 1,450 $m^2$/g, greater than or equal to about 1,500 $m^2$/g, greater than or equal to about 1,550 $m^2$/g, greater than or equal to about 1,600 $m^2$/g, greater than or equal to about 1,700 $m^2$/g, or greater than or equal to about 1,800 $m^2$/g Additionally or alternatively, the catalyst may have a total surface area of about 50 $m^2$/g to about 1,800 $m^2$/g, about 50 $m^2$/g to about 1,500 $m^2$/g, about 50 $m^2$/g to about 1,000 $m^2$/g, about 100 $m^2$/g to about 1,800 $m^2$/g, about 100 $m^2$/g to about 1,700 $m^2$/g, about 100 $m^2$/g to about 1,600 $m^2$/g, about 100 m²/g to about 1,550 m²/g, about 100 m²/g to about 1,500 m²/g, about 100 m²/g to about 1,450 m²/g, about 100 m²/g to about 1,400 m²/g, about 100 m²/g to about 1,300 m²/g, about 100 m²/g to about 1,250 m²/g, about 100 m²/g to about 1,200 m²/g, about 100 m²/g to about 1,150 m²/g, about 100 m²/g to about 1,100 m²/g, about 100 m²/g to about 1,050 m²/g, about 100 m²/g to about 1,000 m²/g, about 100 m²/g to about 900 m²/g, about 100 m²/g to about 850 m²/g, about 100 m²/g to about 800 m²/g, about 100 m²/g to about 700 m²/g, about 100 m²/g to about 600 m²/g, about 100 m²/g to about 550 m²/g, about 100 m²/g to about 500 m²/g, about 100 m²/g to about 450 m²/g, about 100 m²/g to about 400 m²/g, about 100 m²/g to about 300 m²/g, about 100 m²/g to about 200 m²/g, about 300 m²/g to about 1,800 m²/g, about 300 m²/g to about 1,700 m²/g, about 300 m²/g to about 1,600 m²/g, about 300 m²/g to about 1,550 m²/g, about 300 m²/g to about 1,500 m²/g, about 300 m²/g to about 1,450 m²/g, about 300 m²/g to about 1,400 m²/g, about 300 m²/g to about 1,300 m²/g, about 300 m²/g to about 1,250 m²/g, about 300 m²/g to about 1,200 m²/g, about 300 m²/g to about 1,150 m²/g, about 300 m²/g to about 1,100 m²/g, about 300 m²/g to about 1,050 m²/g, about 300 m²/g to about 1,000 m²/g, about 300 m²/g to about 900 m²/g, about 300 m²/g to about 850 m²/g, about 300 m²/g to about 800 m²/g, about 300 m²/g to about 700 m²/g, about 300 m²/g to about 600 m²/g, about 300 m²/g to about 550 m²/g, about 300 m²/g to about 500 m²/g, about 300 m²/g to about 450 m²/g, or about 300 m²/g to about 400 m²/g. In particular, the catalyst may have a total surface area of about 300 m²/g to about 1,500 m²g.

10. Pore Volume

The pore volume of the catalyst described herein can be determined, for example, using nitrogen adsorption-desorption isotherm techniques within the expertise of one of skill in the art, such as the BET (Brunauer Emmet Teller) method.

In various embodiments, the catalyst can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, or greater than or equal to about 1.5 cm³/g.

Additionally or alternatively, the catalyst can have a pore volume of about 0.1 cm³/g to about 1.5 cm³/g, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.3 cm³/g to about 1.5 cm³/g, about 0.3 cm³/g to about 1.0 cm³/g, about 0.3 cm³/g to about 0.9 cm³/g, about 0.1 cm³/g to about 0.8 cm³/g, about 0.3 cm³/g to about 0.7 cm³/g, about 0.3 cm³/g to about 0.6 cm³/g, about 0.3 cm³/g to about 0.5 cm³/g, or about 0.3 cm³/g to about 0.4 cm³/g. In particular, the catalyst can have a pore volume of about 0.3 cm³/g to about 1.0 cm³/g.

II.C. Catalyst Metal

The catalyst may further comprise at least one catalyst metal. The at least one catalyst metal may be incorporated within the pores of the organosilica material binder and/or within the pores of the microporous material (e.g., zeolite). Exemplary catalyst metals can include, but are not limited to, a Group 6 metal, a Group 8 metal, a Group 9 metal, a Group 10 metal or a combination thereof. Exemplary Group 6 metals can include, but are not limited to, chromium, molybdenum, and/or tungsten, particularly including molybdenum and/or tungsten. Exemplary Group 8 metals can include, but are not limited to, iron, ruthenium, and/or osmium. Exemplary Group 9 metals can include, but are not limited to, cobalt, rhodium, and/or iridium, particularly including cobalt. Exemplary Group 10 metals can include, but are not limited to, nickel, palladium and/or platinum.

In a particular embodiment, the catalyst metal may be selected from the group consisting of a Group 8 metal, a Group 9 metal, a Group 10 metal and a combination thereof. Additionally or alternatively, the at least one catalyst metal may be selected from the group consisting of platinum (Pt), palladium (Pd), iridium (Ir), rhodium (Rh), rehenium (Re), ruthenium (Ru), osmium (Os) or a combination thereof, particularly, platinum (Pt), palladium (Pd), and a mixture thereof.

Additionally or alternatively, the catalyst metal may be present in an amount of at least about 0.010 wt %, at least about 0.050 wt %, at least about 0.10 wt %, at least about 0.20 wt %, at least about 0.40 wt %, at least about 0.50 wt %, at least about 0.60 wt %, at least about 0.80 wt %, at least about 1.0 wt %, at least about 1.2 wt %, at least about 1.4 wt %, at least about 1.5 wt %, at least about 1.6 wt %, at least about 1.8 wt %, at least about 2.0 wt %, at least about 2.2 wt %, at least about 2.4 wt %, at least about 2.6 wt %, at least about 2.8 wt %, at least about 3.0 wt %, at least about 3.5 wt %, at least about 4.0 wt %, at least about 5.0 wt %, at least about 7.0 wt %, at least about 10 wt %, at least about 12 wt %, at least about 15 wt %, at least about 17 wt % or at least 20 wt %. All metals weight percents are on support. By "on support" it is meant that the percents are based on the weight of the support, i.e., microporous material (e.g., zeolite) and/or the organosilica material binder. For example, if the support were to weigh 100 grams, then 20 wt % catalyst metal would mean that 20 grams of the catalyst metal was on the support.

Additionally or alternatively, the catalyst metal may be present in an amount of about 0.010 wt % to about 20 wt %, about 0.010 wt % to about 15 wt %, about 0.010 wt % to about 10 wt %, about 0.010 wt % to about 5.0 wt %, about 0.010 wt % to about 4.0 wt %, about 0.010 wt % to about 3.5 wt %, about 0.010 wt % to about 3.0 wt %, about 0.010 wt % to about 2.8 wt %, about 0.010 wt % to about 2.6 wt %, about 0.010 wt % to about 2.4 wt %, about 0.010 wt % to about 2.2 wt %, about 0.010 wt % to about 2.0 wt %, about 0.010 wt % to about 1.8 wt %, about 0.010 wt % to about 1.6 wt %, about 0.010 wt % to about 1.5 wt %, about 0.010 wt % to about 1.4 wt %, about 0.010 wt % to at least about 1.2 wt %, about 0.010 wt % to about 1.0 wt %, about 0.010 wt % to about 0.80 wt %, about 0.010 wt % to about 0.60 wt %, about 0.010 wt % to about 0.50 wt %, about 0.010 wt % to about 0.40 wt %, about 0.010 wt % to about 0.20 wt %, about 0.010 wt % to about 0.10 wt %, about 0.10 wt % to about 20 wt %, about 0.10 wt % to about 15 wt %, about 0.10 wt % to about 10 wt %, about 0.10 wt % to about 5.0 wt %, about 0.10 wt % to about 4.0 wt %, about 0.10 wt % to about 3.5 wt %, about 0.10 wt % to about 3.0 wt %, about 0.10 wt % to about 2.8 wt %, about 0.10 wt % to about 2.6 wt %, about 0.10 wt % to about 2.4 wt %, about 0.10 wt % to about 2.2 wt %, about 0.10 wt % to about 2.0 wt %, about 0.10 wt % to about 1.8 wt %, about 0.10 wt % to about 1.6 wt %, about 0.10 wt % to about 1.5 wt %, about 0.10 wt % to about 1.4 wt %, about 0.10 wt % to at least about 1.2 wt %, about 0.10 wt % to about 1.0 wt %, about 0.10 wt % to about 0.80 wt %, about 0.10 wt % to about 0.60 wt %, about 0.10 wt % to about 0.50 wt %, about 0.10 wt % to about 0.40 wt %, about 0.10 wt % to about 0.20 wt %, about 1.0 wt % to about 20 wt %, about 1.0 wt % to about 15 wt %, about 1.0 wt % to about 10 wt %, about 1.0 wt % to about 5.0 wt %, about 1.0 wt % to about 4.0 wt %, about 1.0 wt % to about 3.5 wt %, about 1.0 wt % to about 3.0 wt %, about 1.0 wt % to about 2.8 wt %, about 1.0 wt % to about 2.6 wt %, about 1.0 wt % to about 2.4 wt %, about 1.0 wt % to about 2.2 wt %, about 1.0 wt % to about 2.0 wt %, about 1.0 wt % to about 1.8 wt %, about 1.0 wt % to about 1.6 wt %, about 1.0 wt % to about 1.5 wt %, about 1.0 wt % to about 1.4 wt %, or about 1.0 wt % to at least about 1.2 wt %.

In particular, the catalyst metal may be present in an amount of about 0.010 wt % to about 20 wt %, about 0.010 wt % to about 10 wt %, about 0.010 wt % to about 4.0 wt %, about 0.05 wt % to about 3.5 wt %, about 0.1 wt % to about 2.0 wt %, or about 0.1 wt % to about 1.4 wt %.

II.D. Further Binder Material

In various aspects, the catalyst may further comprise a further binder in addition to the organosilica material binder described above. Suitable further binders, include but are not limited to active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the further binder may be selected from the group consisting of active and inactive materials, inorganic materials, clays, alumina, silica, silica-alumina, titania, zirconia, or a combination thereof. Particularly, the further binder may be silica-alumina, alumina and/or zirconia, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst.

II.E. Further Metals

In some embodiments, the organosilica material binder can further comprise cationic metal sites incorporated into the network structure. Such cationic metal sites may be incorporated by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Additionally or alternatively, the organosilica material support can further comprise a surface metal incorporated within the pores of the organosilica material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-10 and/or 13 elements may be present on an exterior and/or interior surface of the organosilica material support. For example, one or more of the Group 1, 2 and/or 13 elements may be present in a first layer on the organosilica material and one or more of the Group 6, 8, 9 and/or 10 elements may be present in a second layer, e.g., at least partially atop the Group 1, 2 and/or 13 elements. Additionally or alternatively, only one or more Group 6, 8, 9 and/or 10 elements may present on an exterior and/or interior surface of the organosilica material. The surface metal(s) can be incorporated into/onto the organosilica material by any convenient method, such as by impregnation, deposition, grafting, co-condensation, by ion exchange, and/or the like. In particular, a Group 13 metal, such as, but not limited to, aluminum may be grafted onto a surface of the organosilica material support. Additionally or alternatively, a Group 4 metal, such as, but not limited to, titanium, zirconium and hafnium, may be grafted onto a surface of the organosilica material support.

III. Methods of Making Catalysts

In another embodiment, methods of producing the catalysts described herein are provided. The method can comprise:

a) adding at least one compound (also referred to as a organosilica material binder precursor) into an aqueous mixture that contains essentially no structure directing agent and/or porogen to form a solution, wherein the at least one compound is selected from the group consisting of:
(i) a compound of Formula $[Z^1Z^2SiCH_2]_3$ (Ia), wherein each $Z^1$ represents a $C_1$-$C_4$ alkoxy group and each $Z^2$ represents a $C_1$-$C_4$ alkoxy group or a $C_1$-$C_4$ alkyl group; and
(ii) a cyclic compound of Formula

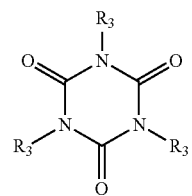

(IIa)

wherein each $R^3$ is independently a $X^1OX^2X^3SiX^4$ group, wherein each $X^1$ represents a $C_1$-$C_4$ alkyl group; $X^2$ and $X^3$ each independently represent a $C_1$-$C_4$ alkyl group, or a $C_1$-$C_4$ alkoxy group; and each $X^4$ represents a $C_1$-$C_8$ alkylene group bonded to a nitrogen atom of the cyclic compound;

(b) mixing at least one microporous material with the solution to form a pre-product;
(c) shaping the pre-product to form catalyst particles;
(d) curing the catalyst particles;
(e) drying the catalyst particles, wherein the catalyst particles comprise the at least one microporous material bound with a polymer of at least one monomer selected from the group consisting of:
(i) a monomer of Formula $[Z^{15}Z^{16}SiCH_2]_3$ (I), wherein each $Z^{15}$ represents a hydroxyl group, a $C_1$-$C_4$ alkoxy group or an oxygen atom bonded to a silicon atom of another monomer and each $Z^{16}$ represents a hydroxyl group, a $C_1$-$C_4$ alkoxy group, a $C_1$-$C_4$ alkyl group, or an oxygen atom bonded to a silicon atom of another monomer; and (ii) a cyclic polyurea monomer of Formula

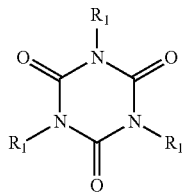

(II)

wherein each $R^1$ independently is a $X^5OX^6X^7SiX^8$ group, wherein each $X^5$ represents a hydrogen atom, a $C_1$-$C_4$ alkyl group, or a bond to a silicon atom of another monomer unit; $X^6$ and $X^7$ each independently represent a hydroxyl group, a $C_1$-$C_4$ alkyl group, a $C_1$-$C_4$ alkoxy group, or an oxygen atom bonded to a silicon atom of another monomer unit; and each $X^8$ represents a $C_1$-$C_8$ alkylene group bonded to a nitrogen atom of the cyclic polyurea; and (f) incorporating at least one catalyst metal within the pores of the at least one microporous material, the catalyst particles or a combination thereof.

III.A. Aqueous Mixture

The catalysts described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

1. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4))a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

2. Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyper-branched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

3. Base/Acid

In various embodiments, the aqueous mixture used in the methods provided herein can comprise a base and/or an acid. It is understood that pH of the aqueous mixture may change over time.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 9 to about 14 or about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

The above described pHs may correspond to the pH of the aqueous mixture before, during and/or after addition of the at least one compound (precursor).

III.B. Compounds of Formula (Ia)

The methods provided herein comprise the step of adding at least one compound of Formula $[Z^1Z^2SiCH_2]_3$ (Ia) into the aqueous mixture to form a solution, wherein each $Z^1$ can be a $C_1$-$C_4$ alkoxy group and each $Z^2$ can be a $C_1$-$C_4$ alkoxy group or a $C_1$-$C_4$ alkyl group.

In one embodiment, each $Z^1$ can be a $C_1$-$C_3$ alkoxy or a $C_1$-$C_2$ alkoxy or methoxy or ethoxy.

Additionally or alternatively, each $Z^2$ can be a $C_1$-$C_4$ alkoxy, or a $C_1$-$C_3$ alkoxy, or a $C_1$-$C_2$ alkoxy or methoxy or ethoxy. Additionally or alternatively, each $Z^2$ can comprise methyl, ethyl or propyl, such as a methyl or ethyl.

Additionally or alternatively, each $Z^1$ can be a $C_1$-$C_2$ alkoxy group and $Z^2$ can be a $C_1$-$C_2$ alkoxy group or a $C_1$-$C_2$ alkyl group.

Additionally or alternatively, each $Z^1$ can be methoxy or ethoxy and each $Z^2$ can be methyl or ethyl.

In a particular embodiment, $Z^1$ and $Z^2$ can be ethoxy, such that the compound corresponding to Formula (Ia) can be 1,1,3,3,5,5-hexaethoxy-1,3,5-trisilacyclohexane, $([(EtO)_2SiCH_2]_3)$.

In a particular embodiment, $Z^1$ can be ethoxy and $Z^2$ can be methyl, such that compound corresponding to Formula (Ia) can be 1,3,5-trimethyl-1,3,5-triethoxy-1,3,5-trisilacyclohexane, $([EtOCH_3SiCH_2]_3)$.

Additionally or alternatively, the method can further comprise adding to the aqueous mixture a further compound Formula (Ia), which may be the same or different. For example, 1,1,3,3,5,5-hexaethoxy-1,3,5-trisilacyclohexane, $([(EtO)_2SiCH_2]_3)$ and 1,3,5-trimethyl-1,3,5-triethoxy-1,3,5-trisilacyclohexane, $([EtOCH_3SiCH_2]_3)$ may be added to the aqueous mixture.

When more than one compound of Formula (Ia) is used, the respective compounds may be used in a wide variety of molar ratios. For example, if two compounds of Formula (Ia) are used, the molar ratio of each compound may vary from 1:99 to 99:1, such as from 10:90 to 90:10. The use of different compounds of Formula (Ia) allows to tailor the properties of the catalyst made by the process of the invention, as will be further explained in the examples and in the section of this specification describing the properties of the catalysts made by the present processes.

III.C. Compounds of Formula (IIa)

Additionally or alternatively, the methods provided herein comprise the step of adding at least one a cyclic compound of Formula

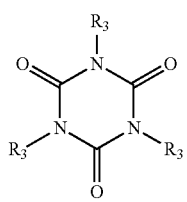

(IIa)

wherein each $R^3$ is independently a $X^1OX^2X^3SiX^4$ group, wherein each $X^1$ represents a $C_1$-$C_4$ alkyl group; $X^2$ and $X^3$ each independently represent a $C_1$-$C_4$ alkyl group, or a $C_1$-$C_4$ alkoxy group; and each $X^4$ represents a $C_1$-$C_8$ alkylene group bonded to a nitrogen atom of the cyclic compound.

In various embodiments, each $X^1$ can be a $C_1$-$C_4$ alkyl, a $C_1$-$C_3$ alkyl, a $C_1$-$C_2$ alkyl or methyl.

Additionally or alternatively, each $X^2$ and $X^3$ each independently can be a $C_1$-$C_4$ alkyl group, a $C_1$-$C_3$ alkyl group, a $C_1$-$C_2$ alkyl group or methyl.

Additionally or alternatively, each $X^2$ and $X^3$ each independently can be a $C_1$-$C_4$ alkoxy group, a $C_1$-$C_3$ alkoxy group, a $C_1$-$C_2$ alkoxy group or methoxy.

Additionally or alternatively, each $X^2$ and $X^3$ each independently can be a $C_1$-$C_2$ alkyl group or a $C_1$-$C_2$ alkoxy group.

Additionally or alternatively, each $X^1$ can be $C_1$-$C_2$ alkyl group; and $X^2$ and $X^3$ each independently can be a $C_1$-$C_2$ alkyl group or a $C_1$-$C_2$ alkoxy group.

Additionally or alternatively, each $X^4$ can be a $C_1$-$C_7$ alkylene group bonded to a nitrogen atom of the cyclic compound, a $C_1$-$C_7$ alkylene group bonded to a nitrogen atom of the cyclic compound, a $C_1$-$C_6$ alkylene group bonded to a nitrogen atom of the cyclic compound, a $C_1$-$C_4$ alkylene group bonded to a nitrogen atom of the cyclic compound, a $C_1$-$C_3$ alkylene group bonded to a nitrogen atom of the cyclic compound, a $C_1$-$C_2$ alkylene group bonded to a nitrogen atom of the cyclic compound, or —$CH_2$— bonded to a nitrogen atom of the cyclic compound.

Additionally or alternatively, each $X^1$ can be a $C_1$-$C_2$ alkyl group; $X^2$ and $X^3$ each independently can be a $C_1$-$C_2$ alkyl group or a $C_1$-$C_2$ alkoxy group; and $X^4$ can be a $C_1$-$C_4$ alkylene group bonded to a nitrogen atom of the cyclic compound.

In a particular embodiment, each $X^1$ can be methyl; $X^2$ and $X^3$ each independently can be methoxy; and $X^4$ can be —$CH_2CH_2CH_2$—, such that the compound corresponding to Formula (IIa) can be tris(3-trimethoxysilylpropyl)isocyanurate.

III.D. Compounds of Formula (IIIa)

In additional embodiments, the methods provided herein can further comprise adding to the aqueous solution a compound of Formula $Z^{17}OZ^{18}Z^{19}Z^{20}Si$ (IIIa), wherein each $Z^{17}$ can be a $C_1$-$C_6$ alkyl group, and $Z^{15}$, $Z^{19}$ and $Z^{20}$ each independently can be selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group.

Additionally or alternatively, each $Z^{17}$ can be a $C_1$-$C_6$ alkyl group, and $Z^{18}$, $Z^{19}$ and $Z^{20}$ each independently can be selected from the group consisting of a $C_1$-$C_6$ alkyl group and a $C_1$-$C_6$ alkoxy group. Additionally or alternatively, $Z^{18}$, $Z^{19}$ and $Z^{20}$ each independently optionally can be a nitrogen-containing $C_1$-$C_{10}$ alkyl group, a nitrogen-containing heteroaralkyl group, and a nitrogen-containing optionally substituted heterocycloalkyl group.

In various aspects, each $Z^{17}$ can be a $C_1$-$C_5$ alkyl group, a $C_1$-$C_4$ alkyl group, a $C_1$-$C_3$ alkyl group, a $C_1$-$C_2$ alkyl group, or methyl. In particular, $Z^{17}$ can be methyl or ethyl.

Additionally or alternatively, $Z^{18}$, $Z^{19}$ and $Z^{20}$ can be each independently a $C_1$-$C_5$ alkyl group, a $C_1$-$C_4$ alkyl group, a $C_1$-$C_3$ alkyl group, a $C_1$-$C_2$ alkyl group, or methyl.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group.

Additionally or alternatively, $Z^{15}$, $Z^{19}$ and $Z^{20}$ can be each independently a $C_1$-$C_5$ alkoxy group, a $C_1$-$C_4$ alkoxy group, a $C_1$-$C_3$ alkoxy group, a $C_1$-$C_2$ alkoxy group, or methoxy.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkoxy group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group or a $C_1$-$C_2$ alkoxy group.

Additionally or alternatively, $Z^{15}$, $Z^{19}$ and $Z^{20}$ can be each independently a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^{15}$, $Z^{19}$ and $Z^{20}$ can be each independently a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_5$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

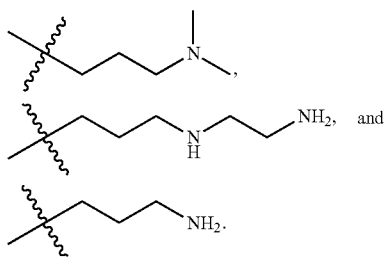

Additionally or alternatively, each $Z^{17}$ can be a $C_1$-$C_2$ alkyl group and $Z^{18}$, $Z^{19}$ and $Z^{20}$ can be each independently a nitrogen-containing $C_3$-$C_8$ alkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group or a nitrogen-containing $C_3$-$C_8$ alkyl group.

Additionally or alternatively, $Z^{18}$, $Z^{19}$ and $Z^{20}$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, each $Z^{17}$ can be a $C_1$-$C_2$ alkyl group and $Z^{18}$, $Z^{19}$ and $Z^{20}$ can be each independently a nitrogen-containing heteroaralkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_5$ alkyl group or a nitrogen-containing heteroaralkyl group.

Additionally or alternatively, $Z^{18}$, $Z^{19}$ and $Z^{20}$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_5$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, each $Z^{17}$ can be a $C_1$-$C_2$ alkyl group and $Z^{18}$, $Z^{19}$ and $Z^{20}$ can be each independently a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group.

Additionally or alternatively, each $Z^{17}$ can be a $C_1$-$C_2$ alkyl group and $Z^{18}$, $Z^{19}$ and $Z^{20}$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

In a particular embodiment, $Z^{17}$ can be ethyl and $Z^{18}$, $Z^{19}$ and $Z^{20}$ can be ethoxy, such that the compound corresponding to Formula (IIIa) can be tetraethyl orthosilicate (TEOS) ((EtO)$_4$Si).

In another particular embodiment, a compound of Formula (Ia) can be 1,1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IIIa) can be tetraethyl orthosilicate (TEOS) ((EtO)$_4$Si).

In another particular embodiment, $Z^{17}$ can be ethyl, $Z^{18}$ can be methyl and $Z^{19}$ and $Z^{20}$ can be ethoxy, such that the compound corresponding to Formula (IIIa) can be methyltriethoxysilane (MTES) ((EtO)$_3$CH$_3$Si).

In another particular embodiment, a compound of Formula (Ia) can be 1,1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IIIa) can be methyltriethoxysilane (MTES) ((EtO)$_3$CH$_3$Si).

In another particular embodiment, a compound of Formula (Ia) can be 1,3,5-trimethyl-1,3,5-triethoxy-1,3,5-trisilacyclohexane ([EtOCH$_3$SiCH$_2$]$_3$) and/or a compound of Formula (IIa) can be tris(3-trimethoxysilylpropyl)isocyanurate and/or a compound of Formula (IIIa) can be methyltriethoxysilane (MTES) ((EtO)$_3$CH$_3$Si).

In another particular embodiment, a compound of Formula (Ia) can be 1,3,5-trimethyl-1,3,5-triethoxy-1,3,5-trisilacyclohexane ([EtOCH$_3$SiCH$_2$]$_3$ and/or a compound of Formula (IIa) can be tris(3-trimethoxysilylpropyl)isocyanurate and/or a compound of Formula (IIIa) can be tetraethyl orthosilicate (TEOS) ((EtO)$_4$Si).

In another particular embodiment, $Z^{17}$ can be ethyl, $Z^{18}$ and $Z^{19}$ can be ethoxy and $Z^{20}$ can be

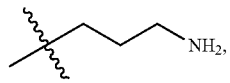

such that the compound corresponding to Formula (IIIa) can be (3-aminopropyl)triethoxysilane (H$_2$N(CH$_2$)$_3$(EtO)$_3$Si).

In another particular embodiment, a compound of Formula (Ia) can be 1,1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a a compound of Formula (IIIa) can be (3-aminopropyl)triethoxysilane (H$_2$N(CH$_2$)$_3$(EtO)$_3$Si).

In another particular embodiment, $Z^{17}$ can be methyl, $Z^{18}$ and $Z^{19}$ can be methoxy and $Z^{20}$ can be

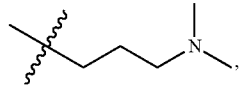 [SMILES: *CCCN(C)C]

such that the compound corresponding to Formula (IIIa) can be (N,N-dimethylaminopropyl)trimethoxysilane ((($CH_3$)$_2$N ($CH_2$)$_3$)(MeO)$_3$Si).

In another particular embodiment, a compound of Formula (Ia) can be 1, 1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IIIa) can be (N,N-dimethylaminopropyl)trimethoxysilane ((($CH_3$)$_2$N($CH_2$)$_3$)(MeO)$_3$Si).

In another particular embodiment, $Z^{17}$ can be ethyl, $Z^{18}$ and $Z^{19}$ can be ethoxy and $Z^{20}$ can be

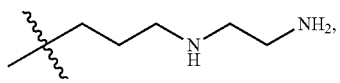 [SMILES: *CCCNCCN]

such that the compound corresponding to Formula (IIIa) can be (N-(2-aminoethyl)-3-aminopropyltriethoxysilane (($H_2$N ($CH_2$)$_2$NH ($CH_2$)$_3$)(EtO)$_2$Si).

In another particular embodiment, a compound of Formula (Ia) can be 1, 1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IIIa) can be (N-(2-aminoethyl)-3-aminopropyltriethoxysilane (($H_2$N(CH$_2$)$_2$NH (CH$_2$)$_3$)(EtO)$_2$Si).

In another particular embodiment, $Z^{17}$ can be ethyl, $Z^{18}$ and $Z^{19}$ can be ethoxy and $Z^{20}$ can be

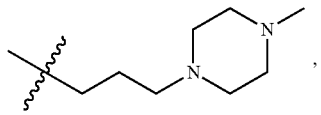 [SMILES: *CCCN1CCN(C)CC1]

such that the compound corresponding to Formula (IIIa) can be 4-methyl-1-(3-triethoxysilylpropyl)-piperazine.

In another particular embodiment, a compound of Formula (Ia) can be 1, 1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IIIa) can be 4-methyl-1-(3-triethoxysilylpropyl)-piperazine.

In another particular embodiment, $Z^{17}$ can be ethyl, $Z^{18}$ and $Z^{19}$ can be ethoxy and $Z^{20}$ can be

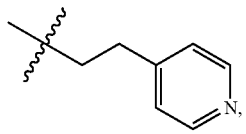 [SMILES: *CCc1ccncc1]

such that the compound corresponding to Formula (IIIa) can be 4-(2-(triethoxysily)ethyl)pyridine.

In another particular embodiment, a compound of Formula (Ia) can 1, 1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IIIa) can be 4-(2-(triethoxysily) ethyl)pyridine.

In another particular embodiment, $Z^{17}$ can be ethyl, $Z^{18}$ and $Z^{19}$ can be ethoxy and $Z^{20}$ can be

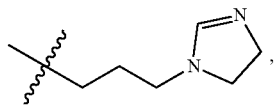 [SMILES: *CCCN1C=NCC1]

such that the compound corresponding to Formula (IIIa) can be 1-(3-(triethoxysilyl)propyl)-4,5-dihydro-1H-imidazole.

In another particular embodiment, a compound of Formula (Ia) can be 1, 1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IIIa) can be 1-(3-(triethoxysilyl) propyl)-4,5-dihydro-1H-imidazole.

In another particular embodiment, the compound of Formula (IIIa) is selected from the group consisting of tetraethyl orthosilicate, methyltriethoxysilane, (N,N-dimethylaminopropyl)trimethoxysilane, N-(2-aminoethyl)-3-aminopropyltriethoxysilane, 4-methyl-1-(3-triethoxysilylpropyl)-piperazine, 4-(2-(triethoxysily)ethyl)pyridine, 1-(3-(triethoxysilyl)propyl)-4,5-dihydro-1H-imidazole, and (3-aminopropyl) triethoxysilane.

The molar ratio of compound of Formula (Ia) to compound of Formula (IIIa) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (IIIa) can be from about 4:1 to 1:4 or from about 2.5:1 to about 1:2.5, about 2:1 to about 1:2, such as about 1.5:1 to about 1.5:1.

The molar ratio of compound of Formula (IIa) to compound of Formula (IIIa) may vary within wide limits, such as from about 99:1 to about 1:99, from about 1:5 to about 5:1, from about 4:1 to about 1:4 or from about 3:2 to about 2:3. For example, a molar ratio of compound of Formula (IIa) to compound of Formula (IIIa) can be from about 4:1 to 1:4 or from about 2.5:1 to about 1:2.5, about 2:1 to about 1:2, such as about 1.5:1 to about 1.5:1.

III.E. Compounds of Formula (IVa)

In additional embodiments, the methods provided herein can further comprise adding to the aqueous solution a compound of Formula $Z^{21}Z^{22}Z^{23}$Si—$R^1$—Si $Z^{21}Z^{23}Z^{24}$ (IVa) wherein each $Z^{21}$ independently can be a $C_1$-$C_4$ alkoxy group; $Z^{22}$ and $Z^{23}$ each independently can be a $C_1$-$C_4$ alkoxy group or a $C_1$-$C_4$ alkyl group; and each $R^1$ can be selected from the group consisting a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl group, and an optionally substituted $C_4$-$C_{20}$ heterocycloalkyl group.

Additionally or alternatively, each $Z^{21}$ independently can be a $C_1$-$C_4$ alkoxy group; $Z^{22}$ and $Z^{23}$ each independently can be a $C_1$-$C_4$ alkoxy group or a $C_1$-$C_4$ alkyl group; and each $R^1$ can be selected from the group consisting a $C_1$-$C_8$ alkylene group, a $C_2$-$C_8$ alkenylene group, and a $C_2$-$C_8$ alkynylene group. Additionally or alternatively, $R^1$ can optionally be a nitrogen-containing $C_1$-$C_{10}$ alkylene group, an optionally substituted $C_6$-$C_{20}$ aralkyl group, and/or an optionally substituted $C_4$-$C_{20}$ heterocycloalkyl group.

In various embodiments, each $Z^{21}$ can be a $C_1$-$C_3$ alkoxy group, a $C_1$-$C_2$ alkoxy group, or methoxy.

Additionally or alternatively, $Z^{22}$ and $Z^{23}$ each independently can be a $C_1$-$C_3$ alkoxy group, a $C_1$-$C_2$ alkoxy group, or methoxy.

Additionally or alternatively, each $Z^{21}$ can be a $C_1$-$C_2$ alkoxy group and $Z^{22}$ and $Z^{23}$ each independently can be a $C_1$-$C_2$ alkoxy group.

Additionally or alternatively, $Z^{22}$ and $Z^{33}$ each independently can be a $C_1$-$C_3$ alkyl group, a $C_1$-$C_2$ alkyl group, or methyl.

Additionally or alternatively, each $Z^{21}$ can be a $C_1$-$C_2$ alkoxy group and $Z^{22}$ and $Z^{23}$ each independently can be a $C_1$-$C_2$ alkyl group.

Additionally or alternatively, $Z^{21}$ can be a $C_1$-$C_2$ alkoxy group and $Z^{22}$ and $Z^{23}$ each independently can be a $C_1$-$C_2$ alkoxy group or a $C_1$-$C_2$ alkyl group.

Additionally or alternatively, each $R^1$ can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —$CH_2$—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^7$ can be a $C_1$-$C_2$ alkylene group.

Additionally or alternatively, each $R^1$ can be a $C_2$-$C_7$ alkenylene group, a $C_1$-$C_6$ alkenylene group, a $C_2$-$C_5$ alkenylene group, a $C_2$-$C_4$ alkenylene group, a $C_2$-$C_3$ alkenylene group, or —CH=CH—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_1$-$C_2$ alkenylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_1$-$C_2$ alkylene group or a $C_1$-$C_2$ alkenylene group.

Additionally or alternatively, each $R^1$ can be a $C_2$-$C_7$ alkynylene group, a $C_1$-$C_6$ alkynylene group, a $C_2$-$C_5$ alkynylene group, a $C_2$-$C_4$ a alkynylene group, a $C_2$-$C_3$ alkynylene group, or —C≡C—.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and $R^1$ can be a $C_2$-$C_4$ alkynylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group or a $C_2$-$C_4$ alkynylene group.

Additionally or alternatively, each $R^1$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to, Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a nitrogen-containing $C_4$-$C_{10}$ alkylene group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_1$-$C_4$ alkylene group, a $C_2$-$C_4$ alkenylene group, a $C_2$-$C_4$ alkynylene group or a nitrogen-containing $C_4$-$C_{10}$ alkylene group.

Additionally or alternatively, each $R^1$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be an optionally substituted $C_6$-$C_{10}$ aralkyl.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group, or an optionally substituted $C_6$-$C_{10}$ aralkyl.

Additionally or alternatively, $R^1$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and $R^1$ can be an optionally substituted $C_4$-$C_{12}$ heterocycloalkyl group.

Additionally or alternatively, each $Z^{21}$ can be a $C_1$-$C_2$ alkoxy group; $Z^{22}$ and $Z^{23}$ each independently can be a $C_1$-$C_2$ alkoxy group or a $C_1$-$C_2$ alkyl group; and each $R^1$ can be a $C_2$-$C_4$ alkylene group, a $C_2$-$C_4$ alkenylene group, a $C_2$-$C_4$ alkynylene group, an optionally substituted $C_6$-$C_{10}$ aralkyl, or an optionally substituted $C_4$-$C_{12}$ heterocycloalkyl group.

In a particular embodiment, $Z^{21}$ and $Z^{22}$ can be ethoxy, $Z^{23}$ can be methyl and $R^1$ can be —$CH_2CH_2$—, such that compound corresponding to Formula (IVa) can be 1,2-bis(methyldiethoxysilyl)ethane ($CH_3(EtO)_2Si$—$CH_2CH_2$—$Si(EtO)_2CH_3$).

In another particular embodiment, a compound of Formula (Ia) can be 1,1,3,3,5,5-hexaethoxy-1,3,5-trisilacyclohexane ($[(EtO)_2SiCH_2]_3$), and/or a compound of Formula (IIa) can be tris(3-trimethoxysilylpropyl)isocyanurate and/or a compound of Formula (IVa) can be 1,2-bis(methyldiethoxysilyl)ethane ($CH_3(EtO)_2Si$—$CH_2CH_2$—$Si(EtO)_2CH_3$).

In another particular embodiment, $Z^{21}$, $Z^{22}$ and $Z^{23}$ can be ethoxy and $R^1$ can be —$CH_2$—, such that compound corresponding to Formula (IVa) can be bis(triethoxysilyl)methane (($EtO)_3Si$—$CH_2$—$Si(EtO)_3$).

In another particular embodiment, a compound of Formula (Ia) can be 1,1,3,3,5,5-hexaethoxy-1,3,5-trisilacyclo-

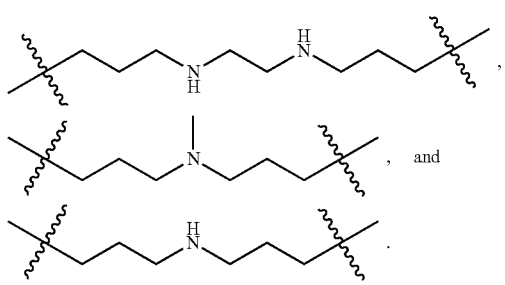

hexane ([(EtO)$_2$SiCH$_2$]$_3$) and/or a compound of Formula (IIa) can be tris(3-trimethoxysilylpropyl)isocyanurate and/or a compound of Formula (IVa) can be bis(triethoxysilyl)methane ((EtO)$_3$Si—CH$_2$—Si(EtO)$_3$).

In another particular embodiment, $Z^{21}$, $Z^{22}$ and $Z^{23}$ can be ethoxy and $R^1$ can be —HC=CH—, such that compound corresponding to Formula (IVa) can be 1,2-bis(triethoxysilyl)ethylene ((EtO)$_3$Si—HC=CH—Si(EtO)$_3$).

In another particular embodiment, a compound of Formula (Ia) can be 1,1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IVa) can be 1,2-bis(triethoxysilyl)ethylene ((EtO)$_3$Si—HC=CH—Si(EtO)$_3$).

In another particular embodiment, a compound of Formula (IVa) can be bis(triethoxysilyl)methane ((EtO)$_3$Si—CH$_2$—Si(EtO)$_3$) and/or a compound of Formula (IIa) can be tris(3-trimethoxysilylpropyl)isocyanurate and/or a compound of Formula (IIIa) can be tetraethyl orthosilicate (TEOS) ((EtO)$_4$Si).

In a particular embodiment, $Z^{21}$, $Z^{22}$ and $Z^{23}$ can be methoxy and $R^1$ can be

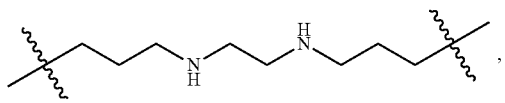 [SMILES: *CCCNCCNCCC*]

such that compound corresponding to Formula (IVa) can be N,N'-bis[(3-trimethoxysilyl)propyl]ethylenediamine.

In another particular embodiment, a compound of Formula (Ia) can be 1,1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IVa) can be N,N'-bis[(3-trimethoxysilyl)propyl]ethylenediamine.

In another particular embodiment, $Z^{21}$ and $Z^{22}$ can be ethoxy, $Z^{23}$ can be methyl and $R^1$ can be

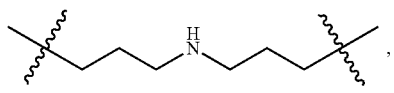 [SMILES: *CCCNCCC*]

such that compound corresponding to Formula (IVa) can be bis[(methyldiethoxysilyl)propyl]amine.

In another particular embodiment, Formula (Ia) can be 1,1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IVa) can be bis[(methyldiethoxysilyl)propyl]amine.

In another particular embodiment, $Z^{21}$ and $Z^{22}$ can be methoxy, $Z^{23}$ can be methyl and $R^1$ can be

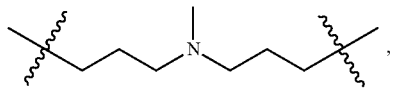 [SMILES: *CCCN(C)CCC*]

such that compound corresponding to Formula (IVa) can be bis[(methyldimethoxysilyl)propyl]-N-methylamine.

In another particular embodiment, a compound of Formula (Ia) can be 1,1,3,3,5,5-hexaethoxy-1,3,5-trisilacyclohexane ([(EtO)$_2$SiCH$_2$]$_3$) and/or a compound of Formula (IIa) can be tris(3-trimethoxysilylpropyl)isocyanurate and/or a compound of Formula (IVa) can be bis[(methyldimethoxysilyl)propyl]-N-methylamine and optionally, no other compounds are added to the aqueous mixture.

In another particular embodiment, a compound of Formula (Ia) can be selected from the group consisting of 1,2-bis(methyldiethoxysilyl)ethane, bis(triethoxysilyl)methane, 1,2-bis(triethoxysilyl)ethylene, N,N'-bis[(3-trimethoxysilyl)propyl]ethylenediamine, bis[(methyldiethoxysilyl)propyl]amine, and bis[(methyldimethoxysilyl)propyl]-N-methylamine.

The molar ratio of compound of Formula (Ia) to compound of Formula (IVa) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (IVa) can be from about 4:1 to 1:4 or from about 2.5:1 to 1:2.5, about 2:1 to about 1:2, such as about 1.5:1 to about 1.5:1.

The molar ratio of compound of Formula (IIa) to compound of Formula (IVa) may vary within wide limits, such as from about 99:1 to about 1:99, from about 1:5 to about 5:1, from about 4:1 to about 1:4 or from about 3:2 to about 2:3. For example, a molar ratio of compound of Formula (IIa) to compound of Formula (IVa) can be from about 4:1 to 1:4 or from about 2.5:1 to 1:2.5, about 2:1 to about 1:2, such as about 1.5:1 to about 1.5:1.

III.F. Sources of Trivalent Metal Oxide

In additional embodiments, the methods provided herein can comprise adding to the aqueous mixture a source of a trivalent metal oxide.

Sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, Al$_2$O$_3$, aluminum halides (e.g., AlCl$_3$), NaAlO$_2$, boron nitride, B$_2$O$_3$ and/or H$_3$BO$_3$.

In various aspects, the source of trivalent metal oxide may be a compound of Formula M$^3$(OZ$^{24}$)$_3$ (Va), wherein M$^3$ can be a Group 13 metal and each $Z^{24}$ independently can be a $C_1$-$C_6$ alkyl group.

In one embodiment, M$^3$ can be B, Al, Ga, In, Il, or Uut. In particular, M$^3$ can be Al or B.

Additionally or alternatively, each $Z^{24}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{15}$ can be methyl, ethyl, propyl or butyl.

Additionally or alternatively, M$^3$ can be Al or B and each $Z^{24}$ can be methyl, ethyl, propyl or butyl.

In a particular embodiment, M$^3$ can be Al and each $Z^{24}$ can be methyl, such that compound corresponding to Formula (Va) can be aluminum trimethoxide.

In a particular embodiment, M$^3$ can be Al and each $Z^{24}$ can be ethyl, such that compound corresponding to Formula (Va) can be aluminum triethoxide.

In a particular embodiment, M$^3$ can be Al and each $Z^{24}$ can be propyl, such that compound corresponding to Formula (Va) can be aluminum isopropoxide.

In a particular embodiment, M$^3$ can be Al and each $Z^{24}$ can be butyl, such that compound corresponding to Formula (Va) can be aluminum tri-sec-butoxide.

In another particular embodiment, a compound of Formula (Ia) can be 1,1,3,3,5,5-hexaethoxy-1,3,5-trisilacyclohexane, ([(EtO)$_2$SiCH$_2$]$_3$) and/or a compound of Formula (IIa) can be tris(3-trimethoxysilylpropyl)isocyanurate and/or a compound of Formula (Va) can be selected from the group consisting of aluminum trimethoxide, aluminum triethoxide, aluminum isopropoxide, and aluminum tri-sec-butoxide.

In another particular embodiment, a compound of Formula (Ia) can be 1, 1,3,3,5,5-hexaethoxy-1,3,5-trisilacyclohexane ($[(EtO)_2SiCH_2]_3$) and/or a compound of Formula (IIa) can be tris(3-trimethoxysilylpropyl)isocyanurate and/or a compound of Formula (Va) can be aluminum tri-sec-butoxide.

Additionally or alternatively, the source of trivalent metal oxide may be a compound of Formula $(Z^{16}O)_2M^4\text{-}O\text{-}Si(OZ^{17})_3$ (VIa), wherein $M^4$ can be a Group 13 metal and $Z^{25}$ and $Z^{26}$ each independently can be a $C_1$-$C_6$ alkyl group.

In one embodiment, $M^4$ can be B, Al, Ga, In, Il, or Uut. In particular, $M^4$ can be Al or B.

Additionally or alternatively, $Z^{25}$ and $Z^{26}$ each independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{25}$ and $Z^{26}$ each independently can be methyl, ethyl, propyl or butyl.

Additionally or alternatively, $M^4$ can be Al or B and $Z^{25}$ and $Z^{26}$ each independently can be methyl, ethyl, propyl or butyl.

Additionally or alternatively, the source of a trivalent metal oxide may be a source of a compound of Formula (Va) (e.g., $AlCl_3$), and/or a source of a compound of Formula (VIa).

The molar ratio of compound of Formula (Ia) or Formula (Iia) to trivalent metal oxide may vary within wide limits, such as from about 99:1 to about 1:99, from about 30:1 to about 1:1, from about 25:1 to about 1:1, from about 20:1 to about 3:1 or from about 20:1 to about 5:1.

III.G. Molar Ratio

In the methods described herein, a molar ratio of Formula (Ia):Formula (Ia), Formula (Ia):Formula (IIIa), Formula (Ia):Formula (IVa), Formula (IVa):Formula (IIIa), Formula (Ia):Formula (Va), Formula (Ia):Formula (IIa), Formula (Ia):Formula (VIa), Formula (IIa):Formula (Ia), Formula (IIa):Formula (IIIa) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1 about 5:2 and about 15:1 may be used. For example, a molar ratio of Formula (Ia):Formula (Ia) can be about 3:2. A molar ratio of Formula (Ia):Formula (IIIa) can be about 2:3, about 4:3, about 4:1 or about 3:2. A molar ratio of Formula (Ia):Formula (IVa) can be about 2:3, and about 4:1. A molar ratio of Formula (IVa):Formula (IIIa) can be about 5:2, about 1:1, about 1:2 or about 2:3. A molar ratio of Formula (Ia):Formula (Va) and Formula (Ia):Formula (VIa) can be about 15:1 or about 5:1. A molar ratio of Formula (IIa):Formula (Ia), and/or Formula (IIa):Formula (IIIa) can be about 3:2.

For the sake of the following discussion, the compounds of Formula (Ia), (IIIa), and (IVa) shall be referred to collectively as starting siloxane. Depending on the choice of starting materials, the solution may have a variety of compositions. For example, if base is used, the solution may have molar ratios of starting siloxane to OHF of from about 1:5 to about 1:20, such as from about 1:5 to about 1:15 or from about 1:5 to about 1:10, or from about 1:6 to about 1:20. If acid is used, the solution may have molar ratios of starting siloxane:$H^+$ of from about 50:1 to about 5:1, such as from about 45:1 to about 10:1. In both cases when acid or base is used, the molar ratios of starting siloxane to $H_2O$ may vary from about 1:50 to about 1:1000, such as from about 1:100 to about 1:500.

III.H. Microporous Material

The methods described herein comprise mixing at least one microporous material as described herein with the solution to form a pre-product. The pre-product may have the consistency of a paste.

As discussed herein, a suitable microporous material may be a zeolite with the framework types described herein. For example, suitable zeolites can include, but are not necessarily limited to, ZSM-5, ZSM-11, ZSM-12, ZSM-22, ZSM-23, ZSM-35, ZSM-48, ZSM-50, ZSM-57, MCM-49, MCM-22, and the like, as well as intergrowths and combinations thereof.

Additionally or alternatively, the microporous material may be an aluminophosphate (i.e., ALPO), such as, but not limited to AlPO-11, AlPO-$H_2$, AlPO-31 and AlPO-41. Additionally or alternatively, the microporous material may be a silicoaluminophosphate (i.e., SAPO), such as, but not limited to SAPO-11, SAPO-41, and SAPO-31.

In various aspects, the at least one microporous material may be selected from the group consisting of a zeolite, a SAPO, an ALPO and a combination thereof. In particular, the at least one microporous material may selected from the group consisting of ZSM-5, ZSM-11, ZSM-22, ZSM-23, ZSM-35, ZSM-48, ZSM-50, ZSM-57, MCM-49, MCM-22, SAPO-11, SAPO-41, AlPO-11, AlPO-$H_2$, and AlPO-41.

The microporous material and the solution may be mixed for any suitable amount of time to form a pre-product. For example, the microporous material and the solution may be mixed for at least about 0.050 hour, at least about 0.10 hour, at least about 0.20 hour, at least about 0.30 hour, at least about 0.40 hour, at least about 0.50 hour, at least about 0.60 hour, at least about 0.70 hour, at least about 0.80 hour, at least about 0.90 hour, at least about 1.0 hour, at least about 2.0 hours, at least about 5.0 hours, at least about 10 hours, at least about 15 hours, or at least about 20 hours.

Additionally or alternatively, the microporous material and the solution may be mixed for about 0.050 hour to about 20 hours, about 0.050 hour to about 15 hours, about 0.050 hour to about 10 hours, about 0.050 hour to about 5.0 hours, about 0.050 hour to about 1.0 hours, about 0.050 hour to about 0.50 hours, about 0.10 hour to about 20 hours, about 0.10 hour to about 15 hours, about 0.10 hour to about 10 hours, about 0.10 hour to about 5.0 hours, about 0.10 hour to about 1.0 hours, about 0.10 hour to about 0.50 hours, about 0.50 hour to about 20 hours, about 0.50 hour to about 15 hours, about 0.50 hour to about 10 hours, about 0.50 hour to about 5.0 hours, or about 0.50 hour to about 1.0 hours. In particular, the microporous material and the solution may be mixed for about 0.050 hour to about 20 hours, about 0.10 hour to about 20 hours, about 0.10 hour to about 10 hours, or about 0.10 hour to about 1.0 hour.

Additionally or alternatively, the microporous material and the solution may be mixed at a temperature of at least about 10° C., at least about 12° C., at least about 14° C., at least about 16° C., at least about 18° C., at least about 20° C., at least about 22° C., at least about 24° C., at least about 26° C., at least about 28° C., at least about 30° C., at least about 32° C., at least about 34° C., at least about 36° C., at least about 38° C., or at least about 40° C. In particular, the microporous material and the solution may be mixed at a temperature about 10° C. to about 40° C., particularly about 12° C. to about 34° C., particularly about 14° C. to about 30° C., particularly about 18° C. to about 28° C., or particularly about 20° C. to about 28° C.

III.I. Shaping the Pre-Product

The methods described herein may comprise shaping the pre-product by any suitable means to form catalyst particles. For example, the pre-product may be extruded into variously shaped catalyst particles. Examples of catalyst particle shapes include, but are not limited to cylinders, spheres, bilobes, trilobes, quadralobes, rings and monoliths.

Additionally or alternatively, the pre-product may molded into catalyst particles by milling and/or spray-drying processes. In particular, shaping the pre-product may comprise extruding, milling, spray-drying and a combination thereof.

III.J. Curing the Catalyst Particles

The methods described herein may further comprise curing the catalyst particles at a suitable temperature, for example, in an oven. The catalyst particles may be cured in the presence of any suitbal gas, e.g., air. The catalyst particles may be cured at a temperature of, at least about 0° C., at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C. at least about 130° C., at least about 140° C., or at least about 150° C., at least about 175° C., or at least about 200° C.

Additionally or alternatively, the catalyst particles formed in the methods described herein may be cured at a temperature of about 0° C. to about 200° C., about 0° C. to about 175° C., about 0° C. to about 150° C., about 0° C. to about 140° C., about 0° C. to about 130° C., about 0° C. to about 120° C., about 0° C. to about 110° C., about 0° C. to about 100° C., about 0° C. to about 90° C., about 0° C. to about 80° C., about 0° C. to about 70° C., about 0° C. to about 60° C., about 0° C. to about 50° C., about 0° C. to about 40° C., about 0° C. to about 30° C., about 20° C. to about 200° C., about 20° C. to about 175° C., about 20° C. to about 150° C., about 20° C. to about 140° C., about 20° C. to about 130° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 20° C. to about 40° C., about 20° C. to about 30° C., about about 40° C. to about 200° C., about 40° C. to about 175° C., about 40° C. to about 150° C., about 40° C. to about 140° C., about 40° C. to about 130° C., about 40° C. to about 120° C., about 40° C. to about 110° C., about 40° C. to about 100° C., about 40° C. to about 90° C., about 40° C. to about 80° C., about 40° C. to about 70° C., about 40° C. to about 60° C., about 40° C. to about 50° C., about 50° C. to about 200° C., about 50° C. to about 175° C., about 50° C. to about 150° C., about 50° C. to about 140° C., about 50° C. to about 130° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 60° C. to about 200° C., about 60° C. to about 175° C., about 60° C. to about 150° C., about 60° C. to about 140° C., about 60° C. to about 130° C., about 60° C. to about 120° C., about 60° C. to about 110° C., about 60° C. to about 100° C., about 60° C. to about 90° C., about 60° C. to about 80° C., about 60° C. to about 70° C., about 70° C. to about 200° C., about 70° C. to about 175° C., about 70° C. to about 150° C., about 70° C. to about 140° C., about 70° C. to about 130° C., about 70° C. to about 120° C., about 70° C. to about 110° C., about 70° C. to about 100° C., about 70° C. to about 90° C., about 70° C. to about 80° C., about 80° C. to about 200° C., about 80° C. to about 175° C., about 80° C. to about 150° C., about 80° C. to about 140° C., about 80° C. to about 130° C., about 80° C. to about 120° C., about 80° C. to about 110° C., about 80° C. to about 100° C., or about 80° C. to about 90° C. In particular, the catalyst particles may be cured at a temperature of about 0° C. to about 150° C., about 40° C. to about 150° C., about 50° C. to about 150° C., or about 60° C. to about 110° C.

Additionally or alternatively, the catalyst particles formed in the methods described herein can be cured, optionally at the temperatures described above, for at least about 0.01 hours, at least about 1 hours, at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days), at least about 144 hours (6 days) at least about 200 hours, at least about 300 hours, at least about 400 hours, at least about 500 hours, at least about 600 hours, at least about 700 hours, at least about 800 hours, at least about 900 hours, at least about 1000 hours or at least about 1100 hours.

Additionally or alternatively, the catalyst particles formed in the methods described herein can be cured, optionally at the temperatures described above, for about 0.01 hours to about 1100 hours, about 0.01 hours to about 1000 hours, about 0.01 hours to about 800 hours, about 0.01 hours to about 600 hours, about 0.01 hours to about 500 hours, about 0.01 hours to about 200 hours, about 0.01 hours to about 144 hours (6 days), about 0.01 hours to about 120 hours (5 days), about 4 hours to about 1100 hours, about 4 hours to about 1000 hours, about 4 hours to about 800 hours, about 4 hours to about 600 hours, about 4 hours to about 500 hours, about 4 hours to about 200 hours, about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 1100 hours, about 6 hours to about 1000 hours, about 6 hours to about 800 hours, about 6 hours to about 600 hours, about 6 hours to about 500 hours, about 6 hours to about 200 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 1000 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 1000 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours (1 day) to about 1000 hours, about 24 hours (1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 1000 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 1000 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 1000 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 1000 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours to about 1000 hours, about 72 hours (3 days) to about 144 hours (6 days), about 72 hours (3 days) to about 120 hours (5 days), about 72 hours (3 days) to about 96 hours (4 days), about 96 hours (4 days) to about 1000 hours, about 96 hours (4 days) to about 144 hours (6 days), about 96 hours (4 days) to about 120 hours (5 days), about 120 hours (5 days) to about 1000 hours, about 120 hours (5 days) to about 144 hours (6 days), about 144 hours (6 days) to about 1000 hours, about 200 hours to about 1000 hours, about 400 hours to about 1000 hours, about 500 hours to about 1000 hours, about 600 hours to about 1000 hours, or about 800 hours to about 1000 hours.

In a particular embodiment, the catalyst particles formed in the method can be cured at temperature from about 0° C. to about 150° C. and/or for about 0.1 hours to about 1000 hours.

III.K. Drying the Catalyst Particles

The methods described herein may further comprise drying the catalyst particles at a suitable temperature. The catalyst particles may be dried at a temperature of greater than or equal to about −20° C., greater than or equal to about 0° C., greater than or equal to about 20° C., greater than or equal to about 50° C., greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the catalyst particles formed in the method can be dried at a temperature of about −20° C. to about 600° C., about −20° C. to about 550° C., about −20° C. to about 500° C., about −20° C. to about 450° C., about −20° C. to about 400° C., about −20° C. to about 350° C., about −20° C. to about 300° C., about −20° C. to about 250° C., about −20° C. to about 200° C., about −20° C. to about 150° C., about −20° C. to about 120° C., about −20° C. to about 110° C., about −20° C. to about 100° C., about −20° C. to about 80° C., about −20° C. to about 70° C., about −20° C. to about 50° C., about −20° C. to about 20° C., about −20° C. to about 0° C., about 0° C. to about 600° C., about 0° C. to about 550° C., about 0° C. to about 500° C., about 0° C. to about 450° C., about 0° C. to about 400° C., about 0° C. to about 350° C., about 0° C. to about 300° C., about 0° C. to about 250° C., about 0° C. to about 200° C., about 0° C. to about 150° C., about 0° C. to about 120° C., about 0° C. to about 110° C., about 0° C. to about 100° C., about 0° C. to about 80° C., about 0° C. to about 70° C., about 0° C. to about 50° C., about 0° C. to about 20° C., about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 110° C., about 70° C. to about 100° C., about 70° C. to about 80° C., about 80° C. to about 600° C., about 70° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C. In particular, the catalyst particles formed in the method can be dried at a temperature of about −20° C. to about 200° C.

Additionally or alternatively, the catalyst particles formed in the method can be dried for the amount of time described above for curing the catalyst particles in Sec.

III.J. In particular, the catalyst particles formed in the method can be dried for about 0.1 hours to about 100 hours.

In a particular embodiment, the catalyst particles formed in the method can be dried at temperature from about −20° C. to about 200° C. and/or for about 0.1 hours to about 100 hours.

Additionally or alternatively, the catalyst particles formed in the method can be dried in a $N_2$, air atmosphere and/or under a vacuum.

III.L. Catalyst Particles

The catalyst particles formed in the methods described herein can comprise the at least one microporous material bound with a polymer comprising independent units of at least one monomer selected from the group consisting of a monomer of Formula (I) as described herein, a cyclic polyurea monomer of Formula (II) as described herein and a combination thereof.

In various aspects, each $Z^{15}$ represents a hydroxyl group, a $C_1$-$C_2$ alkoxy group, or an oxygen atom bonded to a silicon atom of another monomer and each $Z^{16}$ represent a hydroxyl group, a $C_1$-$C_2$ alkyl group, a $C_1$-$C_2$ alkoxy group, or an oxygen atom bonded to a silicon atom of another monomer.

Additionally or alternatively, each $Z^{15}$ represents a hydroxyl group, ethoxy, or an oxygen atom bonded to a silicon atom of another monomer and each $Z^{16}$ represent a hydroxyl group, ethoxy, or an oxygen atom bonded to a silicon atom of another monomer.

Additionally or alternatively, each $X^5$ represents a hydrogen atom, a $C_1$-$C_2$ alkyl group or a bond to a silicon atom of another monomer; $X^6$ and $X^7$ each independently represent a hydroxyl group, a $C_1$-$C_2$ alkyl group, a $C_1$-$C_2$ alkoxy group or an oxygen atom bonded to a silicon atom of another monomer; and $X^8$ represents a $C_1$-$C_4$ alkylene group bonded to a nitrogen atom of the cyclic polyurea.

Additionally or alternatively, each $X^5$ represents a hydrogen atom, methyl or a bond to a silicon atom of another monomer unit; $X^6$ and $X^7$ each independently represent a hydroxyl group, methoxy or an oxygen atom bonded to a silicon atom of another monomer unit and $X^8$ represents —$CH_2CH_2CH_2$— bonded to a nitrogen atom of the cyclic polyurea.

In various embodiments, the catalyst particles formed in the methods described herein can comprise the at least one microporous material bound with a polymer further comprising another monomer in combination with independent units of Formula (I) as described herein and/or Formula (II) as described herein, such as another monomer having at least one independent unit of Formula (III) as described herein.

In various embodiments, the catalyst particles formed in the methods described herein can comprise the at least one microporous material bound with a polymer further comprising another monomer in combination with independent units of Formula (I) as described herein and/or Formula (II) as described herein and optionally independent units of Formula (III) as described herein, such as another monomer having at least one independent unit of Formula (IV) as described herein.

In various embodiments, the catalyst particles formed in the methods described herein can comprise the at least one microporous material bound with a polymer further comprising another monomer in combination with independent units of Formula (I) as described herein and/or Formula (II) as described herein and optionally independent units of Formula (III) as described herein and/or Formula (IV) as described herein, such as another monomer having at least one independent unit of Formula (V) as described herein.

In various embodiments, the catalyst particles formed in the methods described herein can comprise the at least one microporous material bound with a polymer further comprising another monomer in combination with independent units of Formula (I) as described herein and/or Formula (II) as described herein and optionally independent units of Formula (III) as described herein, Formula (IV) as described herein and/or Formula (V) as described herein, such as another monomer having at least one independent unit of Formula (VI) as described herein.

In various embodiments, the catalyst particles formed in the methods described herein can comprise the at least one microporous material bound with a polymer further comprising another monomer in combination with independent units of Formula (I) as described herein and/or Formula (II) as described herein and optionally independent units of Formula (III) as described herein, Formula (IV) as described herein, Formula (V) as described herein and/or Formula (VI) as described herein, such as another monomer having at least one independent unit of Formula (VII) as described herein.

III.M. Catalyst Metal Incorporation

In additional embodiments, the methods of making a catalyst can further comprise incorporating at least one catalyst metal as described herein within the pores of the at least one microporous material, the catalyst particles or a combination thereof. In particular, the at least one catalyst metal can be selected from the group consisting of a Group 6 element, a Group 8 element, a Group 9 element, a Group 10 element or a combination thereof, particularly a Group 8, 9, and/or 10 metal (e.g., Pt, Pd, Ir, Rh, Re, Ru, Os or a combination thereof). In particular, the at least one catalyst metal can be selected from the group consisting of Pt, Pd, and a mixture thereof. In an alternative embodiment, the catalyst metal component can be a combination of a non-noble Group VIII metal with a Group VI metal. Suitable combinations can include Ni, Co, or Fe with Mo or W, preferably Ni with Mo or W.

In various aspects, the at least one catalyst metal may be incorporated within the pores of the catalyst particles after curing and/or drying of the catalyst particles. Additionally or alternatively, the at least one catalyst metal may be incorporated within the pores of the at least one microporous material before it is mixed with the solution.

The catalyst metal can be incorporated into the microporous material and/or the catalyst particles by any convenient method, such as by impregnation, by incipient wetness, by ion exchange, by complexation to surface sites or physically admixed with the microporous material and/or the catalyst particles. If the catalyst metal is to be impregnated into or exchanged onto the microporous material and/or the catalyst particles, it may be done, for example, by treating the microporous material and/or the catalyst particles with a suitable ion containing the catalyst metal. If the catalyst metal is platinum, suitable platinum compounds include chloroplatinic acid, platinous chloride and various compounds containing the platinum amine complex. The catalyst metal may also be incorporated into, onto, or with the microporous material and/or the catalyst particles by utilizing a compound(s) wherein the catalyst metal is present in the cation of the compound and/or compounds or in which it is present in the anion of the compound(s). It should be noted that both cationic and anionic compounds can be used. Non-limiting examples of suitable palladium or platinum compounds in which the metal is in the form of a cation or cationic complex are $Pd(NH_3)_4Cl_2$ or $Pt(NH_3)_4Cl_2$ are particularly useful, as are anionic complexes such as the vanadate and metatungstate ions. Cationic forms of other metals are also very useful since they may be exchanged onto the crystalline material or impregnated into it. Additionally or alternatively, the catalyst metal may be incorporated into the microporous material and/or the catalyst particles by complexation to surface sites, or during mullmixing.

The catalyst metal so incorporated may be employed to promote any one of a number of catalytic tranformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof. In particular, the catalyst metal may be employed for aromatic hydrogenation and/or saturation.

III.N. Addition of Organosilica Material

Figure 2:
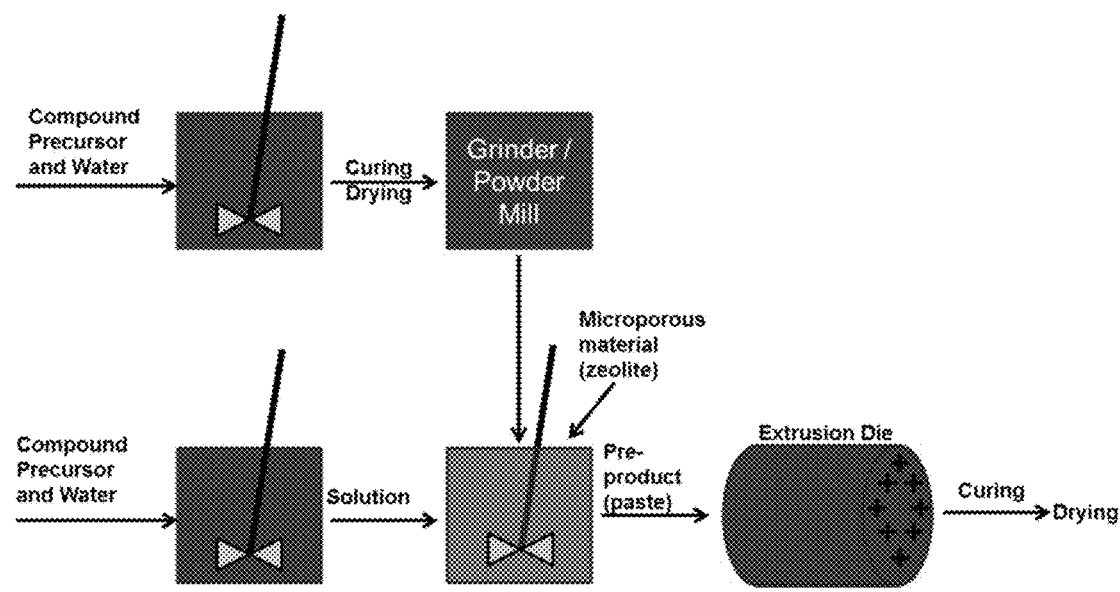
FIG. 2 illustrates a process flow diagram of another embodiment a method of producing a catalyst.

In additional embodiments, the methods of making a catalyst can further comprise adding a further organosilica material to the at least one microporous material and the solution to form the pre-product (e.g., see FIG. 2). This addition of further organosilica material may increase the amount of organosilica material binder present in the catalyst. The organosilica material may be a polymer comprising independent units of at least one monomer selected from the group consisting of a monomer of Formula (I) as described herein, a cyclic polyurea monomer of Formula (II) as described herein and a combination thereof.

Additionally or alternatively, the organosilica material may further comprises at least one other monomer selected from the group consisting of:

(i) an independent unit of Formula (III) as described herein;

(ii) an independent unit of Formula (IV) as described herein;

(iii) an independent unit of Formula (V) as described herein;

(iv) an independent unit of Formula (VI) as described herein;

(v) an independent unit of Formula (VII) as described herein;

(vi) a combination thereof.

The organosilica materials described herein may be produced by the methods described in any one of co-pending U.S. patent application Ser. Nos. 14/965,992, 14/966,001, 14/966,071, 14/965,984, 14/966,383, 14/966,015, 14/966,284, 14/966,407, 14/966,445, 14/966,534, and 14/966,790, each of which are incorporated by reference herein.

III.O. Addition of Binder

In additional embodiments, the methods of making a catalyst can further comprise adding an additional binder material as described herein. In particular, the binder material may be selected from the group consisting of active and inactive materials, inorganic materials, clays, alumina, silica, silica-alumina, titania, zirconia, or a combination thereof. Particularly, the binder may be silica-alumina, alumina and/or zirconia.

III.P. Further Metals

In additional embodiments, the methods of making a catalyst can further comprise adding a surface metal as described herein incorporated within the pores of the microporous material and/or the catalyst particles. Addition of the surface metal can occur prior to impregnation of the microporous material and/or the catalyst particles with the catalyst material. The surface metal can be selected from a Group 1 element, a Group 2 element, a Group 13 element, and a combination thereof as described above. Additionally or alternatively, sources of the surface metal may be compounds of Formulas (X) and/or (XI) as described herein. In particular, the methods described herein can further comprise grafting aluminum on a surface of the microporous material and/or the catalyst particles prior to impregnating the the microporous material and/or the catalyst particles.

III.Q. Calcining

In some embodiments, the method can further comprise calcining the catalyst particles to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 400° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 400° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

IV. Catalyst Product-By-Process

Catalysts can be made from the methods described herein. In another particular embodiment, catalysts can be made from: (a) adding at least one compound into an aqueous mixture as described herein that contains essentially no structure directing agent or porogen as described herein to form a solution as described herein, wherein the at least one compound is selected from the group consisting of: a compound of Formula (Ia) as described herein, a cyclic compound of Formula (IIa) as described herein, and a combination thereof; (b) mixing at least one microporous material as described herein with the solution to form a pre-product as described herein; (c) shaping the pre-product to form catalyst particles as described herein; (d) curing the catalyst particles as described herein; (e) drying the catalyst particles as described herein; and (f) incorporating at least one catalyst metal within the pores of the at least one microporous material, the catalyst particles or a combination thereof as described herein, wherein the catalyst particles may comprise the at least one microporous material bound with: (i) a homopolymer comprising units of Formula (I) as described herein; (ii) a homopolymer comprising units of Formula (II) as described herein; (iii) a copolymer comprising independent units of Formula (I) as described herein and at least one other monomer comprising units of Formulas (II) (III), (IV), (V), (VI) and/or (VII) as described herein; or (iv) a copolymer comprising independent units of Formula (II) as described herein and at least one other monomer comprising units of Formulas (I) (III), (IV), (V), (VI) and/or (VII) as described herein.

V. Aromatic Hydrogenation Process

In various embodiments, an aromatics hydrogenation process for a hydrocarbon feedstream is provided herein.

The aromatics hydrogenation process can comprise contacting a hydrocarbon feedstream comprising aromatics with a catalyst as described herein in the presence of a hydrogen-containing treat gas in a first reaction stage operated under effective aromatics hydrogenation conditions to produce a reaction product with reduced aromatics content. As understood herein, a catalyst can be used for both hydrogenation and aromatic saturation of a feedstream. Similarly, a hydrogenation process can refer to either hydrogenation or aromatic saturation of a feedstream.

In various embodiments, the hydrogenation process can be achieved by contacting a hydrocarbon feedstream with a catalyst described herein in the presence of a hydrogen-containing treat gas in a first reaction stage operated under effective aromatics hydrogenation conditions to produce a reaction product with reduced aromatics content.

Hydrogen-containing treat gasses suitable for use in a hydrogenation process can be comprised of substantially pure hydrogen or can be mixtures of other components typically found in refinery hydrogen streams. It is preferred that the hydrogen-containing treat gas stream contains little, more preferably no, hydrogen sulfide. The hydrogen-containing treat gas purity should be at least about 50% by volume hydrogen, preferably at least about 75% by volume hydrogen, and more preferably at least about 90% by volume hydrogen for best results. It is most preferred that the hydrogen-containing stream be substantially pure hydrogen.

Feedstreams suitable for hydrogenation by the hydrogenation catalyst described herein include any conventional hydrocarbon feedstreams where hydrogenation or aromatic saturation is desirable. Typically, an input feed for an aromatic saturation process can be generated as a product or side-product from a previous type of hydroprocessing, such as hydrocracking for fuels or lubricant base stock production. A wide range of petroleum and chemical feedstocks can be hydroprocessed. Such feedstreams can include hydrocarbon fluids, diesel, kerosene, lubricating oil feedstreams, heavy coker gasoil (HKGO), de-asphalted oil (DAO), FCC main column bottom (MCB), steam cracker tar. Such feedstreams can also include other distillate feedstreams such as light to heavy distillates including raw virgin distillates, wax-containing feedstreams such as feeds derived from crude oils, shale oils and tar sands. Synthetic feeds such as those derived from the Fischer-Tropsch process can also be aromatically saturated using the hydrogenation catalyst described herein. Typical wax-containing feedstocks for the preparation of lubricating base oils have initial boiling points of about 315° C. or higher, and include feeds such as whole and reduced petroleum crudes, hydrocrackates, raffinates, hydrotreated oils, gas oils (such as atmospheric gas oils, vacuum gas oils, and coker gas oils), atmospheric and vacuum residues, deasphalted oils/residua (e.g., propane deasphalted residua, brightstock, cycle oil), dewaxed oils, slack waxes and Fischer-Tropsch wax, and mixtures of these materials. Such feeds may be derived from distillation towers (atmospheric and vacuum), hydrocrackers, hydrotreaters and solvent extraction units, and may have wax contents of up to 50% or more. Preferred lubricating oil boiling range feedstreams include feedstreams which boil in the range of 650-1100° F. Diesel boiling range feedstreams include feedstreams which boil in the range of 480-660° F. Kerosene boiling range feedstreams include feedstreams which boil in the range of 350-617° F.

Hydrocarbon feedstreams suitable for use herein also contain aromatics and nitrogen- and sulfur-contaminants. Feedstreams containing up to 0.2 wt. % of nitrogen, based on the feedstream, up to 3.0 wt. % of sulfur, and up to 50 wt. % aromatics can be used in the present process In various embodiments, the sulfur content of the feedstreams can be below about 500 wppm, or below about 300 wppm, or below about 200 wppm, or below about 100 wppm, or below about 50 wppm, or below about 15 wppm. The pressure used during an aromatic hydrogenation process can be modified based on the expected sulfur content in a feedstream. Feeds having a high wax content typically have high viscosity indexes of up to 200 or more. Sulfur and nitrogen contents may be measured by standard ASTM methods D2622 (sulfur), and D5453 and/or D4629 (nitrogen), respectively.

Effective hydrogenation conditions may be considered to be those conditions under which at least a portion of the aromatics present in the hydrocarbon feedstream are saturated, preferably at least about 50 wt. % of the aromatics are saturated, more preferably greater than about 75 wt. %. Effective hydrogenation conditions can include temperatures of from 150° C. to 400° C., a hydrogen partial pressure of from 100 to 3000 psig (700 to 20100 kPag), a liquid hourly space velocity (LHSV) of from 0.1 to 10 $hr^{-1}$, and a hydrogen to feed ratio of from 500 to 10000 scf/B (85 to 1700 $Nm^3/m^3$).

Additionally or alternatively, effective hydrogenation conditions may be conditions effective at removing at least a portion of the nitrogen and organically bound sulfur contaminants and hydrogenating at least a portion of said aromatics, thus producing at least a liquid lube boiling range product having a lower concentration of aromatics and nitrogen and organically bound sulfur contaminants than the lube boiling range feedstream.

Additionally or alternatively, effective hydrogenation conditions may be conditions effective at removing at least a portion of the nitrogen and organically bound sulfur contaminants and hydrogenating at least a portion of said aromatics, thus producing at least a liquid diesel boiling range product having a lower concentration of aromatics and nitrogen and organically bound sulfur contaminants than the diesel boiling range feedstream.

As stated above, in some instances, the hydrocarbon feedstream (e.g., lube oil boiling range) may be hydrotreated to reduce the sulfur contaminants to below about 500 wppm, particularly below about 300 wppm, particularly below about 200 wppm or particularly below about 100 wppm. In such an embodiment, the process may comprise at least two reaction stages, the first reaction state containing a hydrotreating catalyst operated under effective hydrotreating conditions, and the second containing a catalyst has described herein operated under effective hydrogenation conditions as described above. Therefore, in such an embodiment, the hydrocarbon feedstream can be first contacted with a hydrotreating catalyst in the presence of a hydrogen-containing treat gas in a first reaction stage operated under effective hydrotreating conditions in order to reduce the sulfur content of the feedstream to within the above-described range. Thus, the term "hydrotreating" as used herein refers to processes wherein a hydrogen-containing treat gas is used in the presence of a suitable catalyst that is active for the removal of heteroatoms, such as sulfur, and nitrogen. Suitable hydrotreating catalysts for use in the present invention are any conventional hydrotreating catalyst and includes those which are comprised of at least one Group 8 metal, preferably Fe, Co and Ni, more preferably Co and/or Ni, and most preferably Ni; and at least one Group 6 metal, preferably Mo and W, more preferably Mo, on a high surface area support material, preferably alumina. Additionally or alternatively, more than one type of hydrotreating catalyst can be used in the same reaction vessel. The Group 8 metal may typically be present in an amount ranging from about 2 to 20 wt %, preferably from about 4 to 12 wt %. The Group 6 metal can typically be present in an amount ranging from about 5 to 50 wt %, preferably from about 10 to 40 wt %, and more preferably from about 20 to 30 wt %. All metals weight percents are "on support" as described above.

Effective hydrotreating conditions may be considered to be those conditions that can effectively reduce the sulfur content of the feedstream (e.g., lube oil boiling range) to within the above-described ranges. Typical effective hydrotreating conditions can include temperatures ranging from about 150° C. to about 425° C., preferably about 200° C. to about 370° C., more preferably about 230° C. to about 350° C. Typical weight hourly space velocities ("WHSV") may range from about 0.1 to about 20 $hr^{-1}$, preferably from about 0.5 to about 5 $hr^{-1}$. Any effective pressure can be utilized, and pressures can typically range from about 410 to about 7100 kPag (about 4 to about 70 atmospheres), such as about 1000 to about 4100 kPag (about 10 to about 40 atmospheres). In a particular embodiment, said effective hydrotreating conditions may be conditions effective at removing at least a portion of said organically bound sulfur contaminants and hydrogenating at least a portion of said aromatics, thus producing at least a reaction product (e.g., liquid lube oil boiling range product) having a lower concentration of aromatics and organically bound sulfur contaminants than the lube oil boiling range feedstream.

The contacting of the hydrocarbon feedstream with the hydrotreating catalyst may produce a reaction product comprising at least a vapor product and a liquid product. The vapor product may typically comprise gaseous reaction products, such as $H_2S$, and the liquid reaction product may typically comprise a liquid hydrocarbon having a reduced level of nitrogen and sulfur contaminants. The total reaction product can be passed directly into the second reaction stage, but it may be preferred that the gaseous and liquid reaction products be separated, and the liquid reaction product conducted to the second reaction stage. Thus, in one embodiment, the vapor product and the liquid product may be separated, and the liquid product may be conducted to the second reaction stage. The method of separating the vapor product from the liquid product can be accomplished by any means known to be effective at separating gaseous and liquid reaction products. For example, a stripping tower or reaction zone can be used to separate the vapor product from the liquid product (e.g., liquid lube oil boiling range product). The liquid product thus conducted to the second reaction stage can have a sulfur concentration within the range of about 500 wppm, particularly below about 300 wppm, or particularly below about 200 wppm or particularly below about 100 wppm.

Advantageously, the catalyst described herein may be dual functional. For example, the microporous material (e.g., zeolite) may provide a dewaxing function while the organosilica material binder may provide the aromatic saturation function. Thus, the catalysts described herein may be utilized in more than process, e.g., aromatic saturation and catalytic dewaxing.

In still other embodiments, the hydrogenation catalysts described herein can be used in integrated hydroprocessing methods. In addition to the hydrofinishing and/or aromatic hydrogenation/saturation processes involving the hydrogenation catalyst described herein, an integrated hydroprocessing method can also include various combinations of hydrotreating, hydrocracking, catalytic dewaxing (such as hydrodewaxing), and/or solvent dewaxing. The scheme of hydrotreating followed by hydrofinishing described above represents one type of integrated process flow. Another integrated processing example is to have a dewaxing step, either catalytic dewaxing or solvent dewaxing, followed by hydroprocessing with the hydrogenation catalysts described herein. Still another example is a process scheme involving hydrotreating, dewaxing (catalytic or solvent), and then hydroprocessing with the hydrogenation catalysts described herein. Yet another example is hydroprocessing with the hydrogenation catalysts described herein followed by dewaxing (catalytic or solvent). Alternatively, multiple hydrofinishing and/or aromatic hydrogenation steps can be employed with hydrotreatment, hydrocracking, or dewaxing steps. An example of such a process flow is hydrofinishing, dewaxing (catalytic or solvent), and then hydrofinishing again, where at least one of the hydrofinishing steps may use a hydrogenation catalysts described herein. For processes involving catalytic dewaxing, effective catalytic dewaxing conditions can include temperatures of from 150° C. to 400° C., preferably 250° C. to 350° C., pressures of from 100 to 3000 psig (700 to 21000 kPag), such as from 200 to 2500 psig (from 1400 to 17500 kPag), liquid hourly space velocities of from 0.1 to 10 $hr^{-1}$, such as 0.1 to 5 $hr^{-1}$; and hydrogen treat gas rates from 250 to 10000 scf/B (from 40 to 1700 $Nm^3/m^3$), such as from 500 to 5000 scf/B (from 85 to 850 $Nm^3/m^3$). Any suitable dewaxing catalyst may be used.

In embodiments where the product of an aromatic saturation process will be a lubricant base oil, the input feed should also have suitable lubricant base oil properties. For example, an input feed intended for use as a Group I or Group II base oil can have a viscosity index (VI) of at least about 80, preferably at least about 90 or at least about 95. An input feed intended for use as a Group I+ base oil can have a VI of at least about 100, while an input feed intended for use as a Group II+ base oil can have a VI of at least 110. The viscosity of the input feed can be at least 2 cSt at 100° C., or at least 4 cSt at 100° C., or at least 6 cSt at 100° C.

VI. Further Embodiments

The invention can additionally or alternately include one or more of the following embodiments.

Embodiment 1

A method of making a catalyst, the method comprising:
a) adding at least one compound into an aqueous mixture that contains essentially no structure directing agent and/or porogen to form a solution, wherein the at least one compound is selected from the group consisting of:
(i) a compound of Formula $[Z^1Z^2SiCH_2]_3$ (Ia), wherein each $Z^1$ represents a $C_1$-$C_4$ alkoxy group and each $Z^2$ represents a $C_1$-$C_4$ alkoxy group or a $C_1$-$C_4$ alkyl group; and
(ii) a cyclic compound of Formula (IIa)

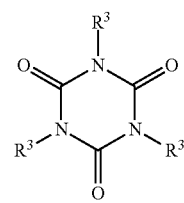

wherein each $R^3$ is independently a $X^1OX^2X^3SiX^4$ group, wherein each $X^1$ represents a $C_1$-$C_4$ alkyl group; $X^2$ and $X^3$ each independently represent a $C_1$-$C_4$ alkyl group, or a $C_1$-$C_4$ alkoxy group; and each $X^4$ represents a $C_1$-$C_8$ alkylene group bonded to a nitrogen atom of the cyclic compound;

(b) mixing at least one microporous material with the solution to form a pre-product;

(c) shaping the pre-product to form catalyst particles;

(d) curing the catalyst particles;

(e) drying the catalyst particles, wherein the catalyst particles comprise the at least one microporous material bound with a polymer comprising independent units of at least one monomer selected from the group consisting of:

(i) a monomer of Formula $[Z^{15}Z^6SiCH_2]_3$ (I), wherein each $Z^{15}$ represents a hydroxyl group, a $C_1$-$C_4$ alkoxy group or an oxygen atom bonded to a silicon atom of another monomer and each $Z^{16}$ represents a hydroxyl group, a $C_1$-$C_4$ alkoxy group, a $C_1$-$C_4$ alkyl group, or an oxygen atom bonded to a silicon atom of another monomer; and (ii) a cyclic polyurea monomer of Formula

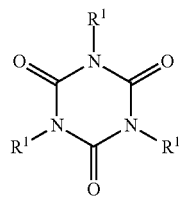

(II)

wherein each $R^1$ independently is a $X^5OX^6X^7SiX^8$ group, wherein each $X^5$ represents a hydrogen atom, a $C_1$-$C_4$ alkyl group, or a bond to a silicon atom of another monomer unit; $X^6$ and $X^7$ each independently represent a hydroxyl group, a $C_1$-$C_4$ alkyl group, a $C_1$-$C_4$ alkoxy group, or an oxygen atom bonded to a silicon atom of another monomer unit; and each $X^8$ represents a $C_1$-$C_8$ alkylene group bonded to a nitrogen atom of the cyclic polyurea; and (f) incorporating at least one catalyst metal within the pores of the at least one microporous material, the catalyst particles or a combination thereof.

Embodiment 2

The method of embodiment 1, wherein each $Z^1$ represents a $C_1$-$C_2$ alkoxy group.

Embodiment 3

The method of embodiment 1 or 2, wherein each $Z^2$ represents a $C_1$-$C_4$ alkoxy group.

Embodiment 4

The method of any one of the previous embodiments, wherein each $Z^2$ represents a $C_1$-$C_2$ alkoxy group.

Embodiment 5

The method of any one of the previous embodiments, wherein the at least one compound of Formula (Ia) is 1,1,3,3,5,5-hexaethoxy-1,3,5-trisilacyclohexane.

Embodiment 6

The method of any one of the previous embodiments, wherein each $X^1$ represents a $C_1$-$C_2$ alkyl group; $X^2$ and $X^3$ each independently represent a $C_1$-$C_2$ alkyl group, or a $C_1$-$C_2$ alkoxy group; and each $X^4$ represents a $C_1$-$C_4$ alkylene group bonded to a nitrogen atom of the cyclic compound.

Embodiment 7

The method of any one of the previous embodiments, wherein the at least one compound of Formula (IIa) is tris(3-trimethoxysilylpropyl)isocyanurate.

Embodiment 8

The method of any one of the previous embodiments, wherein each $Z^{15}$ represents a hydroxyl group, a $C_1$-$C_2$ alkoxy group, or an oxygen atom bonded to a silicon atom of another monomer and each $Z^{16}$ represent a hydroxyl group, a $C_1$-$C_2$ alkyl group, a $C_1$-$C_2$ alkoxy group, or an oxygen atom bonded to a silicon atom of another monomer.

Embodiment 9

The method of any one of the previous embodiments, wherein each $Z^{15}$ represents a hydroxyl group, ethoxy, or an oxygen atom bonded to a silicon atom of another monomer and each $Z^{16}$ represent a hydroxyl group, ethoxy, or an oxygen atom bonded to a silicon atom of another monomer.

Embodiment 10

The method of any one of the previous embodiments, wherein each $X^5$ represents a hydrogen atom, a $C_1$-$C_2$ alkyl group or a bond to a silicon atom of another monomer; $X^6$ and $X^7$ each independently represent a hydroxyl group, a $C_1$-$C_2$ alkyl group, a $C_1$-$C_2$ alkoxy group or an oxygen atom bonded to a silicon atom of another monomer; and $X^8$ represents a $C_1$-$C_4$ alkylene group bonded to a nitrogen atom of the cyclic polyurea.

Embodiment 11

The method of any one of the previous embodiments, wherein each $X^5$ represents a hydrogen atom, methyl or a bond to a silicon atom of another monomer unit; $X^6$ and $X^7$ each independently represent a hydroxyl group, methoxy or an oxygen atom bonded to a silicon atom of another monomer unit and $X^8$ represents —$CH_2CH_2CH_2$— bonded to a nitrogen atom of the cyclic polyurea.

Embodiment 12

The method of any one of the previous embodiments, further comprising adding to the aqueous mixture at least one compound selected from the group consisting of:

(i) a further compound of Formula (Ia);

(ii) a further compound of Formula (IIa);

(iii) a compound of Formula $Z^{17}OZ^{18}Z^{19}Z^{20}Si$ (IIIa), wherein each $Z^{17}$ represents a $C_1$-$C_6$ alkyl group, and $Z^{18}$, $Z^{19}$ and $Z^{20}$ are each independently selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group;

(iv) a compound of Formula $Z^{21}Z^{22}Z^{23}Si-R^1-Si Z^{21}Z^{23}Z^{24}$ (IVa), wherein each $Z^{21}$ independently represents a $C_1$-$C_4$ alkoxy group; $Z^{22}$ and $Z^{23}$ each independently represent a $C_1$-$C_4$ alkoxy group or a $C_1$-$C_4$ alkyl group; and $R^1$ is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;

(v) a source of a trivalent metal oxide; and (vi) a combination thereof.

Embodiment 13

The method of embodiment 12, wherein the at least one compound is a further compound of Formula (Ia), wherein each $Z^1$ represents a $C_1$-$C_2$ alkoxy group and each $Z^2$ represent $C_1$-$C_2$ alkoxy group or a $C_1$-$C_2$ alkyl group.

Embodiment 14

The method of embodiment 12 or 13, wherein the compound of Formula (Ia) is 1,3,5-trimethyl-1,3,5-triethoxy-1,3,5-trisilacyclohexane.

Embodiment 15

The method of any one of embodiments 12-14, wherein the at least one compound is a compound of Formula (IIIa), wherein each $Z^{17}$ represents a $C_1$-$C_2$ alkyl group and $Z^{18}$, $Z^{19}$ and $Z^{20}$ each independently selected from the group consisting of a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, and a nitrogen-containing optionally substituted $C_4$-$C_{10}$ heterocycloalkyl group.

Embodiment 16

The method of any one of embodiments 12-15, wherein the compound of Formula (IIIa) is selected from the group consisting of tetraethyl orthosilicate, methyltriethoxysilane, (N,N-dimethylaminopropyl)trimethoxysilane, N-(2-aminoethyl)-3-aminopropyltriethoxysilane, 4-methyl-1-(3-triethoxysilylpropyl)-piperazine, 4-(2-(triethoxysily)ethyl) pyridine, 1-(3-(triethoxysilyl)propyl)-4,5-dihydro-1H-imidazole, and (3-aminopropyl)triethoxysilane.

Embodiment 17

The method of any one of embodiments 12-16, wherein the at least one compound is a compound of Formula (IVa), wherein each $Z^{21}$ represents a $C_1$-$C_2$ alkoxy group; $Z^{22}$ and $Z^{23}$ each independently represent a $C_1$-$C_2$ alkoxy group, or a $C_1$-$C_2$ alkyl group; and $R^1$ is selected from the group consisting of a $C_1$-$C_4$ alkylene group, a $C_2$-$C_4$ alkenylene group, a $C_2$-$C_4$ alkynylene group, and a nitrogen-containing $C_4$-$C_{10}$ alkylene group.

Embodiment 18

The method of any one of embodiments 12-17, wherein the compound of Formula (IVa) is selected from the group consisting of 1,2-bis(methyldiethoxysilyl)ethane, bis(triethoxysilyl)methane, 1,2-bis(triethoxysilyl)ethylene, N,N'-bis[(3-trimethoxysilyl)propyl]ethylenediamine, bis[(methyldiethoxysilyl)propyl]amine, and bis[(methyldimethoxysilyl)propyl]-N-methylamine.

Embodiment 19

The method of any one of embodiments 12-18, wherein the at least one compound is a source of trivalent metal oxide, wherein the source of trivalent metal oxide is at least one of:

(i) a compound of Formula $M^3(OZ^{24})_3$ (Va), wherein $M^3$ represents a Group 13 metal and each $Z^{24}$ independently represents a $C_1$-$C_6$ alkyl group; or (ii) a compound of Formula $(Z^{25}O)_2M^4-O-Si(OZ^{26})_3$ (VIa), wherein $M^4$ represents a Group 13 metal and $Z^{25}$ and $Z^{26}$ each independently represent a $C_1$-$C_6$ alkyl group.

Embodiment 20

The method of any one of embodiments 12-19, wherein the source of trivalent metal oxide is a compound of Formula (Va), wherein $M^3$ is Al or B and each $Z^{24}$ represents a $C_1$-$C_4$ alkyl group.

Embodiment 21

The method of any one of embodiments 12-20, wherein the source of trivalent metal is a compound of Formula (VIa), wherein $M^4$ is Al or B; and $Z^{25}$ and $Z^{26}$ each independently represent a $C_1$-$C_4$ alkyl group.

Embodiment 22

The method of any one of embodiments 12-21, wherein the source of a trivalent metal oxide is selected from the group consisting of aluminum trimethoxide, aluminum triethoxide, aluminum isopropoxide, and aluminum-tri-sec-butoxide.

Embodiment 23

The method of any one of the previous embodiments, wherein the aqueous mixture comprises a base (e.g., ammonium hydroxide, metal hydroxide) and has a pH from about 8 to about 14.

Embodiment 24

The method of any one of the previous embodiments, wherein the aqueous mixture comprises an acid (e.g., an inorganic acid, such as hydrochloric acid) and has a pH from about 0.01 to about 6.0.

Embodiment 25

The method of any one of the previous embodiments, wherein the at least one microporous material and the solution are mixed in step (b) for about 0.10 hour to about 10 hours.

Embodiment 26

The method of any one of the previous embodiments, wherein the catalyst particles are cured at a temperature of about 0° C. to about 150° C.

Embodiment 27

The method of any one of the previous embodiments, wherein the catalyst particles are dried at a temperature of about −20° C. to about 200° C.

Embodiment 28

The method of any one of the previous embodiments, wherein the at least one catalyst metal is selected from the group consisting of a Group 8 metal, a Group 9 metal, a Group 10 metal and a combination thereof, particularly selected from the group consisting of Pt, Pd, Ir, Rh, Re, Ru, Os and a combination thereof and more particularly, selected from the group consisting of Pt, Pd, and a mixture thereof.

Embodiment 29

The method of any one of the previous embodiments, wherein the at least one catalyst metal is incorporated within the pores of the catalyst particles after drying of the catalyst particles or the at least one catalyst metal is incorporated within the pores of the at least one microporous material before it is mixed with the solution.

Embodiment 30

The method of any one of the previous embodiments, wherein the at least one microporous material is selected from the group consisting of a zeolite, a SAPO, an ALPO and a combination thereof, particularly selected from the group consisting of ZSM-5, ZSM-11, ZSM-22, ZSM-23, ZSM-35, ZSM-48, ZSM-50, ZSM-57, MCM-49, MCM-22, SAPO-11, SAPO-41, AlPO-11, AlPO-$H_2$, and AlPO-4.

Embodiment 31

The method of any one of the previous embodiments further comprising adding a further organosilica material to the at least one microporous material and the solution to form the pre-product, wherein the further organosilica material is a polymer comprising independent units of at least one monomer selected from the group consisting of:
(i) a monomer of Formula (I); and
(ii) a cyclic polyurea monomer of Formula (II).

Embodiment 32

The method of embodiment 31, wherein the organosilica material further comprises at least one other monomer selected from the group consisting of
(i) at least one independent unit of Formula $[Z^3OZ^4SiCH_2]_3$ (III), wherein each $Z^3$ represents a hydrogen atom, a $C_1$-$C_4$ alkyl group or a bond to a silicon atom of another monomer and $Z^4$ represents a $C_1$-$C_6$ alkyl group;
(ii) at least one independent unit of Formula $Z^5OZ^6Z^7Z^8Si$ (IV), wherein each $Z^5$ represents a hydrogen atom or a $C_1$-$C_4$ alkyl group or a bond to a silicon atom of another monomer; and $Z^6$, $Z^7$ and $Z^8$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group and an oxygen atom bonded to a silicon atom of another monomer;
(iii) at least one independent unit of Formula $Z^9Z^{10}Z^{11}Si$—R—S—R—$SiZ^9Z^{11}$ (V), wherein each $Z^9$ independently represents a hydroxyl group, a $C_1$-$C_4$ alkoxy group or an oxygen bonded to a silicon atom of another monomer; $Z^{10}$ and $Z^{11}$ each independently represent a hydroxyl group, a $C_1$-$C_4$ alkoxy group, a $C_1$-$C_4$ alkyl group or an oxygen bonded to a silicon atom of another monomer; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
(iv) at least one independent unit of Formula $M^1(OZ^{12})_3$ (VI), wherein $M^1$ represents a Group 13 metal and each $Z^{12}$ independently represents a hydrogen atom, a $C_1$-$C_6$ alkyl or a bond to a silicon atom of another monomer;
(v) at least one independent unit of Formula $(Z^{13}O)_2M^2$—O—$Si(OZ^4)_3$ (VII), wherein $M^2$ represents a Group 13 metal and $Z^{13}$ and $Z^{14}$ each independently represent a hydrogen atom, a $C_1$-$C_6$ alkyl group or a bond to a silicon atom of another monomer; and
(vi) a combination thereof.

Embodiment 33

The method of any one of the previous embodiments, wherein shaping the pre-product comprises extruding, milling, spray-drying or a combination thereof.

Embodiment 34

A catalyst made according to the method of any one of the previous embodiments.

Embodiment 35

A catalyst comprising:
(i) at least one microporous material;
(ii) an organosilica material binder, which is a polymer comprising independent units of a monomer selected from the group consisting of:
(a) a monomer of Formula $[Z^{15}Z^{16}SiCH_2]_3$ (I), wherein each $Z^{15}$ represents a hydroxyl group, a $C_1$-$C_4$ alkoxy group or an oxygen atom bonded to a silicon atom of another monomer and each $Z^{16}$ represents a hydroxyl group, a $C_1$-$C_4$ alkoxy group, a $C_1$-$C_4$ alkyl group, or an oxygen atom bonded to a silicon atom of another monomer; and
(b) a cyclic polyurea monomer of Formula

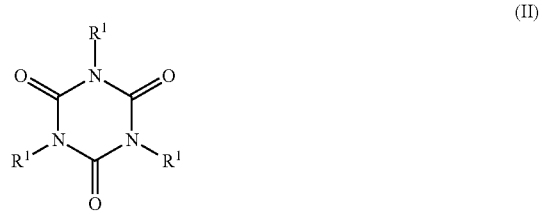

wherein each $R^1$ independently is a $X^5OX^6X^7SiX^8$ group, wherein each $X^5$ represents a hydrogen atom, a $C_1$-$C_4$ alkyl group, or a bond to a silicon atom of another monomer unit; $X^6$ and $X^7$ each independently represent a hydroxyl group, a $C_1$-$C_4$ alkyl group, a $C_1$-$C_4$ alkoxy group, or an oxygen atom bonded to a silicon atom of another monomer unit; and each $X^8$ represents a $C_1$-$C_5$ alkylene group bonded to a nitrogen atom of the cyclic polyurea; and
(iii) at least one catalyst metal.

Embodiment 36

The catalyst of embodiment 35, wherein each $Z^{15}$ represents a hydroxyl group, a $C_1$-$C_2$ alkoxy group, or an oxygen atom bonded to a silicon atom of another siloxane unit and each $Z^{16}$ represent a hydroxyl group, a $C_1$-$C_2$ alkyl group, a $C_1$-$C_2$ alkoxy group, or an oxygen atom bonded to a silicon atom of another siloxane unit.

Embodiment 37

The catalyst of embodiment 35 or 36, wherein each $Z^{15}$ represents a hydroxyl group, ethoxy, or an oxygen atom bonded to a silicon atom of another siloxane and each $Z^{16}$ represent a hydroxyl group, ethoxy, or an oxygen atom bonded to a silicon atom of another siloxane.

Embodiment 38

The catalyst of any one of embodiments 35-37, wherein each $X^5$ represents a hydrogen atom, a $C_1$-$C_2$ alkyl group or a bond to a silicon atom of another monomer unit; $X^6$ and $X^7$ each independently represent a hydroxyl group, a $C_1$-$C_2$ alkyl group, a $C_1$-$C_2$ alkoxy group or an oxygen atom bonded to a silicon atom of another monomer unit and $X^8$ represents a $C_1$-$C_4$ alkylene group bonded to a nitrogen atom of the cyclic polyurea.

Embodiment 39

The catalyst of any one of embodiments 35-38, wherein each $X^5$ represents a hydrogen atom, methyl or a bond to a silicon atom of another monomer unit; $X^6$ and $X^7$ each independently represent a hydroxyl group, methoxy or an oxygen atom bonded to a silicon atom of another monomer unit and $X^8$ represents —$CH_2CH_2CH_2$— bonded to a nitrogen atom of the cyclic polyurea.

Embodiment 40

The catalyst of any one of embodiments 35-39, wherein the organosilica material binder further comprises at least one other monomer selected from the group consisting of:

(i) at least one independent unit of Formula $[Z^3OZ^4SiCH_2]_3$ (III), wherein each $Z^3$ represents a hydrogen atom, a $C_1$-$C_4$ alkyl group or a bond to a silicon atom of another monomer and $Z^4$ represents a $C_1$-$C_6$ alkyl group;

(ii) at least one independent unit of Formula $Z^5OZ^6Z^7Z^8Si$ (IV), wherein each $Z^5$ represents a hydrogen atom or a $C_1$-$C_4$ alkyl group or a bond to a silicon atom of another monomer; and $Z^6$, $Z^7$ and Ze are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group and an oxygen atom bonded to a silicon atom of another monomer;

(iii) at least one independent unit of Formula $Z^9Z^{10}Z^{11}Si-R-SiZ^9Z^{10}Z^{11}$ (V), wherein each $Z^9$ independently represents a hydroxyl group, a $C_1$-$C_4$ alkoxy group or an oxygen bonded to a silicon atom of another monomer; $Z^{10}$ and $Z^{11}$ each independently represent a hydroxyl group, a $C_1$-$C_4$ alkoxy group, a $C_1$-$C_4$ alkyl group or an oxygen bonded to a silicon atom of another monomer; and R is selected from the group consisting a $C_1$-$C_8$ alkylene group, a $C_2$-$C_5$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;

(iv) at least one independent unit of Formula $M^1(OZ^{12})_3$ (VI), wherein $M^1$ represents a Group 13 metal and each $Z^{12}$ independently represents a hydrogen atom, a $C_1$-$C_6$ alkyl or a bond to a silicon atom of another monomer;

(v) at least one independent unit of Formula $(Z^3O)_2M^2$-O—$Si(OZ^4)_3$ (VII), wherein $M^2$ represents a Group 13 metal and $Z^{13}$ and $Z^{14}$ each independently represent a hydrogen atom, a $C_1$-$C_6$ alkyl group or a bond to a silicon atom of another monomer; and (vi) a combination thereof.

Embodiment 41

The catalyst of embodiment 40, wherein at least one independent unit of Formula (III) is present, wherein each $Z^3$ represents a hydrogen atom, a $C_1$-$C_2$ alkyl group or a bond to a silicon atom of another siloxane monomer and each $Z^4$ represents a $C_1$-$C_2$ alkyl group.

Embodiment 42

The catalyst of embodiment 40 or 41, wherein each $Z^3$ represents a hydrogen atom, ethyl or a bond to a silicon atom of another siloxane monomer and each $Z^4$ represents a methyl.

Embodiment 43

The catalyst of any one of embodiments 40-42, wherein at least one independent unit of Formula (IV) is present, wherein each $Z^5$ represents a hydrogen atom, a $C_1$-$C_2$ alkyl group or a bond to a silicon atom of another monomer; and $Z^6$, $Z^7$ and $Z^8$ are each independently selected from the group consisting of a hydroxyl group, a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroalkyl group, a nitrogen-containing optionally substituted $C_4$-$C_{10}$ heterocycloalkyl group and an oxygen bonded to a silicon atom of another monomer.

Embodiment 44

The catalyst of any one of embodiments 40-43, wherein $Z^6$, $Z^7$ and $Z^8$ are each independently selected from the group consisting of a hydroxyl group, a $C_1$-$C_2$ alkyl group, $C_1$-$C_2$ alkoxy group, and an oxygen bonded to a silicon atom of another monomer.

Embodiment 45

The catalyst of any one of embodiments 40-44, wherein each $Z^5$ represents a hydrogen atom, methyl, ethyl, or a bond to a silicon atom of another monomer; and $Z^6$, $Z^7$ and $Z^8$ are each independently selected from the group consisting of a hydroxyl group, methyl, methoxy, ethoxy,

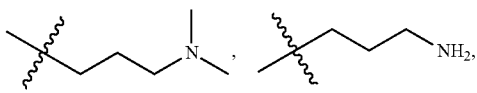

-continued

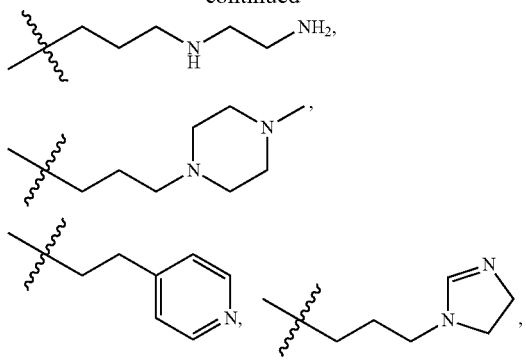

and an oxygen bonded to a silicon atom of another monomer.

Embodiment 46

The catalyst of any one of embodiments 40-45, The catalyst of claim 46, wherein at least one independent unit of Formula (V) is present, wherein each $Z^9$ represents a hydroxyl group, a $C_1$-$C_2$ alkoxy group or an oxygen bonded to a silicon atom of another monomer; $Z^{10}$ and $Z^{11}$ each independently represent a hydroxyl group, a $C_1$-$C_2$ alkoxy group, a $C_1$-$C_2$ alkyl group or an oxygen bonded to a silicon atom of another monomer; and R is selected from the group consisting of a $C_1$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl and an optionally substituted $C_4$-$C_{12}$ heterocycloalkyl group.

Embodiment 47

The catalyst of any one of embodiments 40-46, wherein each $Z^9$ represents a hydroxyl group, methoxy, ethoxy or an oxygen bonded to a silicon atom of another monomer; $Z^{10}$ and $Z^{11}$ each independently represent a hydroxyl group, methoxy, ethoxy or methyl or an oxygen bonded to a silicon atom of another monomer; and R is selected from the group consisting of —CH$_2$—, —CH$_2$CH$_2$—, —HC=CH—

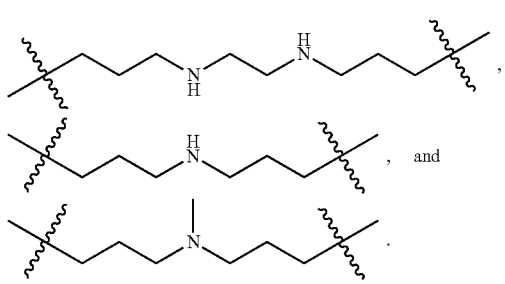

Embodiment 48

The catalyst of any one of embodiments 40-47, wherein at least one independent unit of Formula (VI) is present, wherein $M^1$ is Al or B and each $Z^{12}$ represents a hydrogen atom, a $C_1$-$C_4$ alkyl group or a bond to a silicon atom or another monomer.

Embodiment 49

The catalyst of any one of embodiments 40-48, wherein at least one unit of Formula (VII) is present, wherein $M^2$ is Al or B and $Z^{13}$ and $Z^{14}$ each independently represent a hydrogen atom, a $C_1$-$C_4$ alkyl group or a bond to a silicon atom of another monomer.

Embodiment 50

The catalyst of any one of embodiments 35-49, wherein the organosilica material binder is present in the catalyst in an amount of about 5.0 wt % to about 99 wt %.

Embodiment 51

The catalyst of any one of embodiments 35-50, wherein the microporous material is present in the catalyst in an amount of at most about 95.0 wt %.

Embodiment 52

The catalyst of any one of embodiments 35-51, wherein the at least one catalyst metal is selected from the group consisting of a Group 8 metal, a Group 9 metal, a Group 10 metal and a combination thereof, particularly selected from the group consisting of Pt, Pd, Ir, Rh, Re, Ru, Os and a combination thereof and more particularly selected from the group consisting of Pt, Pd, and a mixture thereof.

Embodiment 53

The catalyst of any one of embodiments 35-52, wherein the at least one microporous material is selected from the group consisting of a zeolite, a SAPO, an ALPO and a combination thereof, particularly selected from the group consisting of ZSM-5, ZSM-11, ZSM-22, ZSM-23, ZSM-35, ZSM-48, ZSM-50, ZSM-57, MCM-49, MCM-22, SAPO-11, SAPO-41, AlPO-11, AlPO-H$_2$, and AlPO-41.

Embodiment 54

The catalyst of any one of embodiments 35-53, wherein the catalyst has a total surface area of about 300 m$^2$/g to about 1500 m$^2$/g.

Embodiment 55

The catalyst of any one of embodiments 35-54, wherein the catalyst has a pore volume of about 0.3 cm$^3$/g to about 1.0 cm$^3$/g.

EXAMPLES

Example 1-Catalyst Synthesis Examples

Comparative Example 1A

High surface area alumina-bound (Versal™ 300; SA>~200 m$^2$/g) ZSM-48 was used as Comparative Sample A having ~65% ZSM-48 (made according to previously published methods, such as described in U.S. Patent Application Publication No. 2011/0192766, which is incorporated by reference herein for this purpose).

Example 1B

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1,3,5-trisilacyclohexane ([(EtO)$_2$SiCH$_2$]$_3$) was added, producing a mixture having the approximate molar composition:

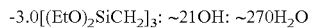
~3.0[(EtO)$_2$SiCH$_2$]$_3$: ~21OH: ~270H$_2$O

The mixture was stirred for ~1 day at room temperature (~20-25° C.) to form a sol solution.

Organosilica powder was separately made by forming a solution of ~18.6 g of ~30% NH$_4$OH and ~23.8 g deionized water (DI) water. The pH of the solution was ~12.6. To the solution, ~12.0 g of 1,1,3,3,5,5-hexaethoxy-1,3,5-trisilacyclohexane ([(EtO)$_2$SiCH$_2$]$_3$) was added, producing a mixture having the approximate molar composition:

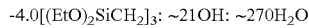
~4.0[(EtO)$_2$SiCH$_2$]$_3$: ~21OH: ~270H$_2$O

The mixture was stirred for ~1 day at room temperature (~20-25° C.), transferred to an autoclave, and aged at ~90° C. for ~1 day to produce a gel. The gel was dried at ~120° C. under vacuum for ~1 day. This produced a solidified gel, which was ground to a white powder. Neither surface directing agent nor porogen were used.

~14.6 g of the sol solution was mixed with ~2.4 g of the organosilica powder and ~6.5 g of H-form calcined ZSM-48 (heated to ~1000° F. for 1-4 hours, washed with ~1N NH$_4$OH, and heated to ~1000° F. for 1-4 hours) to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours to form Sample A having ~65% ZSM-48.

Example 1C

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1,3,5-trisilacyclohexane ([(EtO)$_2$SiCH$_2$]$_3$) was added, producing a mixture having the approximate molar composition:

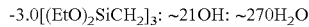
~3.0[(EtO)$_2$SiCH$_2$]$_3$: ~21OH: ~270H$_2$O

The mixture was stirred for ~1 day at room temperature (~20-25° C.) to form a sol solution.

Organosilica powder was separately made by forming a solution of ~18.6 g of ~30% NH$_4$OH and ~23.8 g deionized water (DI) water. The pH of the solution was ~12.6. To the solution, ~12.0 g of 1,1,3,3,5,5-hexaethoxy-1,3,5-trisilacyclohexane ([(EtO)$_2$SiCH$_2$]$_3$) was added, producing a mixture having the approximate molar composition:

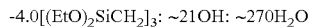
~4.0[(EtO)$_2$SiCH$_2$]$_3$: ~21OH: ~270H$_2$O

The mixture was stirred for ~1 day at room temperature (~20-25° C.), transferred to an autoclave, and aged at ~90° C. for ~1 day to produce a gel. The gel was dried at ~120° C. under vacuum for ~1 day. This produced a solidified gel, which was ground to a white powder. Neither surface directing agent nor porogen were used.

~14.6 g of the sol solution was mixed with ~2.4 g of the organosilica powder and ~6.5 g of H-form calcined ZSM-48 (heated to ~1000° F. for 1-4 hours, washed with ~1N NH$_4$OH, and heated to ~1000° F. for 1-4 hours) to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours. The particles were further steamed at ~890° F. in ~100% steam for ~3 hours to produce Sample B having ~65% ZSM-48.

Example 1D

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1,3,5-trisilacyclohexane ([(EtO)$_2$SiCH$_2$]$_3$) was added, producing a mixture having the approximate molar composition:

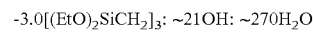
~3.0[(EtO)$_2$SiCH$_2$]$_3$: ~21OH: ~270H$_2$O

The mixture was stirred for ~1 day at room temperature (~20-25° C.) to form a sol solution.

Organosilica powder was separately made by forming a solution of ~84 g of HCl solution (pH ~2) and ~6.0 g of 1,1,3,3,5,5-hexaethoxy-1,3,5-trisilacyclohexane ([(EtO)$_2$SiCH$_2$]$_3$), producing a mixture having the approximate molar composition:

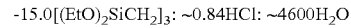
~15.0[(EtO)$_2$SiCH$_2$]$_3$: ~0.84HCl: ~4600H$_2$O

The mixture was stirred for ~1 day at room temperature (~20-25° C.), transferred to an autoclave, and aged at ~90° C. for ~1 day to produce a gel. The gel was dried at ~120° C. under vacuum for ~1 day. This produced a solidified gel, which was ground to a white powder. Neither surface directing agent nor porogen were used.

~15 g of the sol solution was mixed with ~2.1 g of the organosilica powder and ~7 g of H-form calcined ZSM-48 (heated to ~1000° F. for 1-4 hours, washed with ~1N NH$_4$OH, and heated to ~1000° F. for 1-4 hours) to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours to form Sample C having ~68% ZSM-48.

Example 1E

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1,3,5-trisilacyclohexane ([(EtO)$_2$SiCH$_2$]$_3$) was added, producing a mixture having the approximate molar composition:

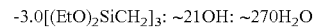
~3.0[(EtO)$_2$SiCH$_2$]$_3$: ~21OH: ~270H$_2$O

The mixture was stirred for ~1 day at room temperature (~20-25° C.) to form a sol solution.

~14.4 g of the sol solution was mixed with ~7 g of H-form calcined ZSM-48 (heated to ~1000° F. for 1-4 hours, washed with ~1N NH$_4$OH, and heated to ~1000° F. for 1-4 hours) to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours to form Sample D having ~86% ZSM-48.

Example 1F

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1,3,5-trisilacyclohexane ([(EtO)$_2$SiCH$_2$]$_3$) was added, producing a mixture having the approximate molar composition:

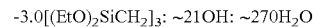
~3.0[(EtO)$_2$SiCH$_2$]$_3$: ~21OH: ~270H$_2$O

The mixture was stirred for ~1 day at room temperature (~20-25° C.) to form a sol solution.

~14.4 g of the sol solution was mixed with ~7 g of H-form calcined ZSM-48 (heated to ~1000° F. for 1-4 hours, washed with ~1N NH$_4$OH, and heated to ~1000° F. for 1-4 hours) to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours. The particles were further steamed at ~890° F. in ~100% steam for ~3 hours to produce Sample E having ~86% ZSM-48.

Example 1G

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1,3,5-trisilacyclohexane ([(EtO)$_2$SiCH$_2$]$_3$) was added, producing a mixture having the approximate molar composition:

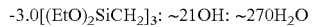
~3.0[(EtO)$_2$SiCH$_2$]$_3$: ~21OH: ~270H$_2$O

The mixture was stirred for ~1 day at room temperature (~20-25° C.) to form a sol solution.

~11.4 g of the sol solution was mixed with ~7 g of H-form calcined/steamed ZSM-5 to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours to form Sample F having ~88% ZSM-5.

Example 1H

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1,3,5-trisilacyclohexane ([(EtO)$_2$SiCH$_2$]$_3$) was added, producing a mixture having the approximate molar composition:

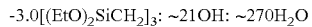
~3.0[(EtO)$_2$SiCH$_2$]$_3$: ~21OH: ~270H$_2$O

The mixture was stirred for ~1 day at room temperature (~20-25° C.) to form a sol solution.

Figure 3:
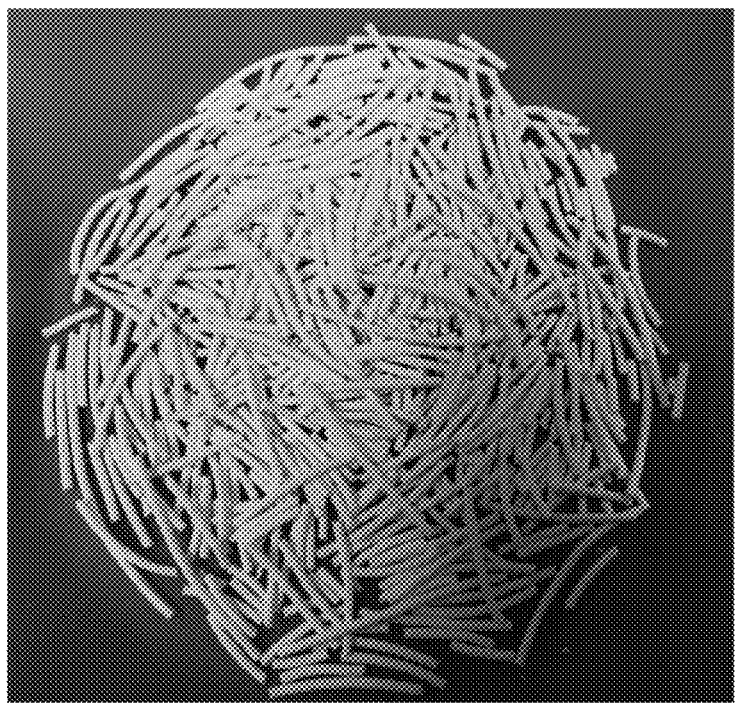
FIG. 3 illustrates cylinder-shaped catalyst particles (Sample G) having ~88 wt % ZSM-48 and ~12 wt % organosilica material binder, made according to Example 1H.

~11.4 g of the sol solution was mixed with ~7 g of H-form calcined ZSM-48 (heated to ~1000° F. for 1-4 hours, washed with ~1N NH$^4$OH, and heated to ~1000° F. for 1-4 hours) to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours to form Sample G having ~88% ZSM-48 and ~12 wt % organosilica binder. FIG. 3 shows the cylinder-shaped catalyst particles of Sample G.

Example 1I

A solution was formed with ~18.6 g of ~30% NH$_4$OH and ~23.8 g deionized (DI) water. The pH of the solution was ~12.6. To the solution ~9.0 g of 1,1,3,3,5,5-hexaethoxy-1, 3,5-trisilacyclohexane ([(EtO)$_2$SiCH$_2$]$_3$) was added, producing a mixture having the approximate molar composition:

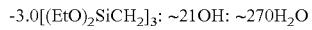
~3.0[(EtO)$_2$SiCH$_2$]$_3$: ~21OH: ~270H$_2$O

The mixture was stirred for ~1 day at room temperature (~20-25° C.) to form a sol solution.

Figure 4:
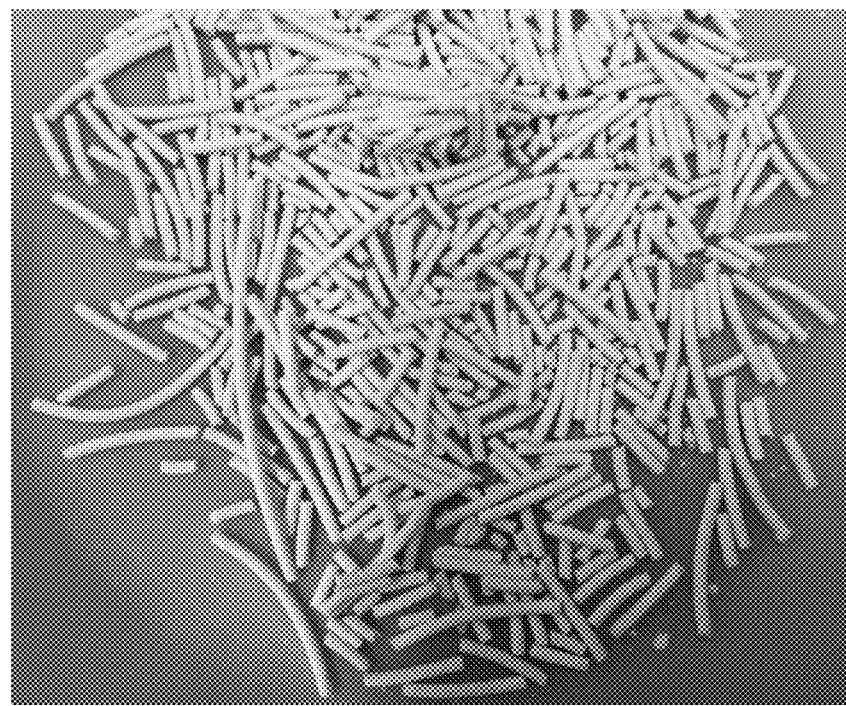
FIG. 4 illustrates cylinder-shaped catalyst particles (Sample H) having ~88 wt % ZSM-5 and ~12 wt % organosilica material binder, made according to Example 1I.

~11.4 g of the sol solution was mixed with ~7 g of H-form calcined/steamed ZSM-5 to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours to form Sample G having ~88% ZSM-5 and ~12 wt % organosilica binder. FIG. 4 shows the cylinder-shaped catalyst particles of Sample H.

Example 1J

A solution was formed with ~18.6 g of ~30% NH$_4$OH and ~23.8 g deionized (DI) water. The pH of the solution was ~12.6. To the solution ~9.0 g of 1, 1,3,3,5,5-hexaethoxy-1, 3,5-trisilacyclohexane ([(EtO)$_2$SiCH$_2$]$_3$) was added, producing a mixture having the approximate molar composition:

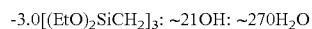
~3.0[(EtO)$_2$SiCH$_2$]$_3$: ~21OH: ~270H$_2$O

The mixture was stirred for ~1 day at room temperature (~20-25° C.) to form a sol solution.

Organosilica powder was separately made by forming a solution of ~84 g of HCl solution (pH ~2) and ~6.0 g of 1,1,3,3,5,5-hexaethoxy-1,3,5-trisilacyclohexane ([(EtO)$_2$SiCH$_2$]$_3$), producing a mixture having the approximate molar composition:

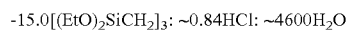
~15.0[(EtO)$_2$SiCH$_2$]$_3$: ~0.84HCl: ~4600H$_2$O

The mixture was stirred for ~1 day at room temperature (~20-25° C.), transferred to an autoclave, and aged at ~90° C. for ~1 day to produce a gel. The gel was dried at ~120° C. under vacuum for ~1 day. This produced a solidified gel, which was ground to a white powder. Neither surface directing agent nor porogen were used.

Figure 5:
FIG. 5 illustrates quadrilobe-shaped catalyst particles (Sample I) having ~68 wt % MCM-49 and ~32 wt % organosilica material binder, made according to Example 1J.

~15 g of the sol solution was mixed with ~7 g of H-form calcined MCM-49 and ~2.1 g of the organosilica powder to make a paste for extrusion. The paste was extruded through an extrusion die to produce shaped particles (quadrulobes). The shaped particles were cured in an oven at ~70° C. for ~16-24 hours and then dried at ~120° C. under vacuum for ~16-24 hours to form Sample I having ~68% MCM-49 and ~32 wt % organosilica binder. FIG. 5 shows the quadrulobe-shaped catalyst particles of Sample I.

Example 1K

A solution was formed with ~6.21 g of ~30% NH$_4$OH and ~7.92 g deionized (DI) water. The pH of the solution was ~12.6. To the solution ~2.0 g of 1,1,3,3,5,5-hexaethoxy-1, 3,5-trisilacyclohexane ([(EtO)$_2$SiCH$_2$]$_3$) was added, producing a mixture having the approximate molar composition:

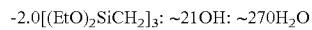
~2.0[(EtO)$_2$SiCH$_2$]$_3$: ~21OH: ~270H$_2$O

The mixture was stirred for ~1 day at room temperature (~20-25° C.) to form a sol solution.

Figure 6A:
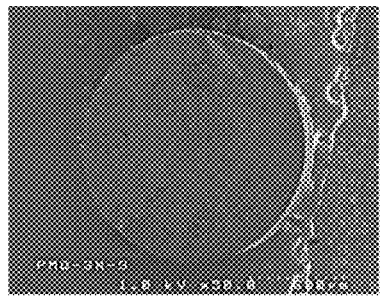
FIGS. 6A, 6B, and 6C illustrate scanning electron microscope (SEM) cross-section images of a catalyst (Sample J, made according to Example 1K) having ~92 wt % ZSM-48 and ~8.0 wt % organosilica material binder at various magnifications.
Figure 6B:
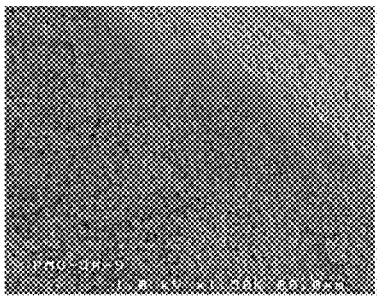
Figure 6C:
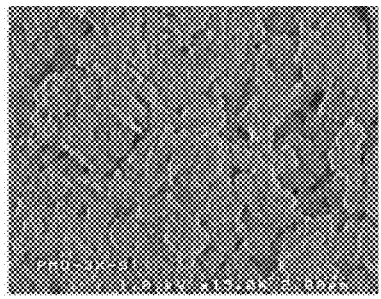
Figure 6D:
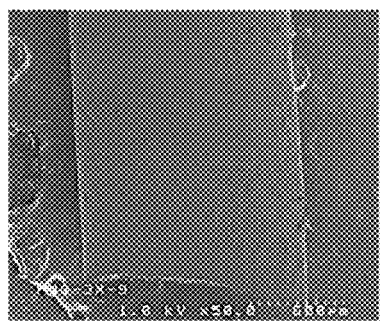
FIGS. 6D, 6E, and 6F illustrate scanning electron microscope (SEM) side view images of a catalyst surface (Sample J, made according to Example 1K) having ~92 wt % ZSM-48 and ~8.0 wt % organosilica material binder at various magnifications.
Figure 6E:
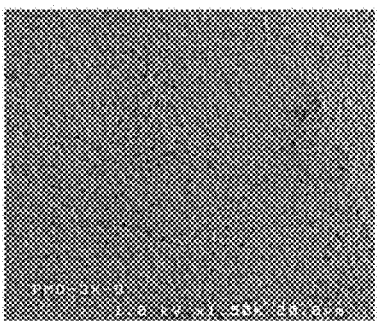
Figure 6F:
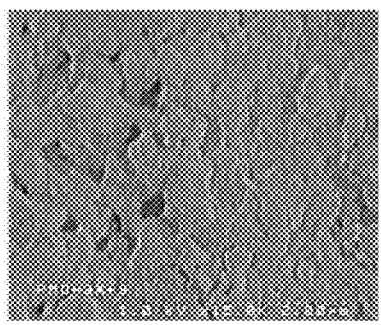
Figure 7A:
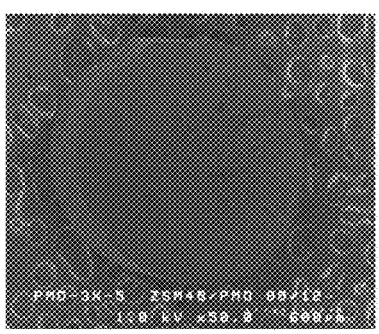
FIGS. 7A, 7B, and 7C illustrate scanning electron microscope (SEM) cross-section images of a catalyst (Sample J, made according to Example 1K) having ~88 wt % ZSM-48 and ~12 wt % organosilica material binder at various magnifications.
Figure 7B:
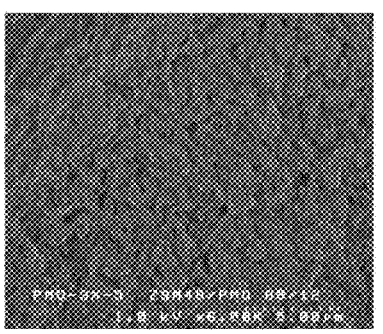
Figure 7C:
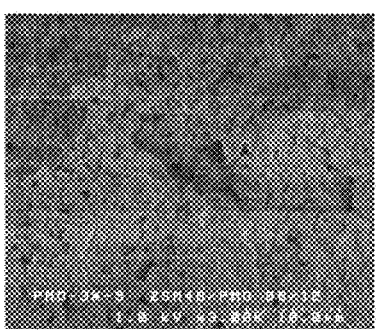
Figure 7D:
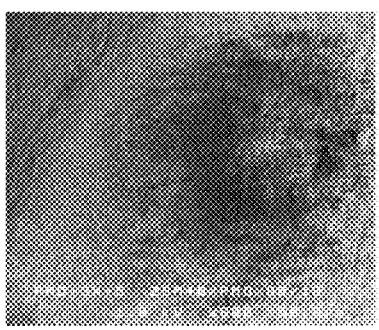
FIGS. 7D, 7E, and 7F illustrate scanning electron microscope (SEM) side view images of a catalyst surface (Sample J, made according to Example 1K) having ~88 wt % ZSM-48 and ~12 wt % organosilica material binder at various magnifications.
Figure 7E:
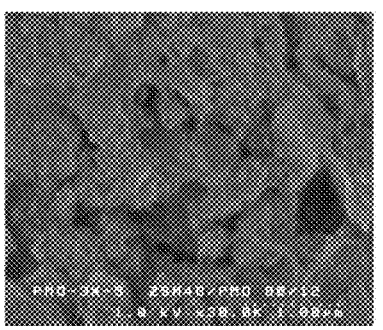
Figure 7F:
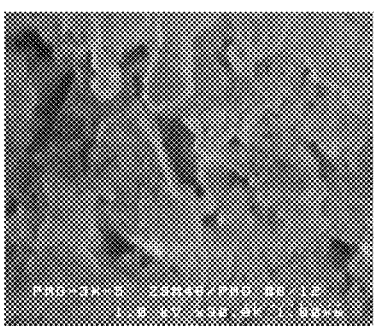

~10.8 g of the sol solution was mixed with ~7 g of H-form calcined ZSM-48 (heated to ~1000° F. for 1-4 hours, washed with ~1N NH$_4$OH, and heated to ~1000° F. for 1-4 hours) to make a paste for extrusion. The paste was extruded through an extrusion die to produce shaped particles (cylinders). The shaped particles were cured in an oven at ~70° C. for ~16-24 hours and then dried at ~120° C. under vacuum for ~16-24 hours to form Sample J having ~92% ZSM-5 and ~8 wt % organosilica binder. FIGS. 6A-6C provide scanning electron microscope (SEM) cross-section images of Sample J. FIGS. 6D-6F illustrate SEM side view images of of Sample J.

Example 2-Catalyst Property Analysis

The following various analysis methods were performed on the catalyst samples. The results are provided in Tables 1-3.

Nitrogen Porosimetry

The nitrogen adsorption/desorption analyses was performed with different instruments, e.g., TriStar™ 3000, TriStar II™ 3020 and Autosorb™-1. All the samples were pre-treated at ~120° C. in vacuum for ~4 hours before collecting the $N_2$ isotherm. The analysis program calculated the experimental data and report BET surface area (total surface area), microporous surface area (S), total pore volume, pore volume for micropores, pore size distribution (nm), average pore diameter (or radius), etc.

2,2-Dimethylbutane (2,2-DMB) and 2,3-Dimethylbutane (2,3-DMB) Sorption and Diffusivity 2,2-DMB and 2,3-DMB sorption and diffusivity may be determined as described in U.S. Pat. Nos. 7,902,414 and 8,507,744, which are incorporated by reference for that purpose. Diffusional resistance for porous crystalline materials is typically reported as the Diffusion Parameter, $D/r^2 \times 10^6$, wherein D is the diffusion coefficient ($cm^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^2$ where t is the time (sec) required to reach the sorbate loading Q. Graphical solutions for the plane sheet model are given by J. Crank in "The Mathematics of Diffusion", Oxford University Press, Ely House, London, 1967.

The hydrocarbon diffusivity, expressed as the inverse of the characteristic diffusion time. $D/r^2$, was determined by the rate of 2,2-dimethylbutane (2,2-DMB) uptake for the catalysts indicated in Tables 1-3. Prior to hydrocarbon adsorption, about 50 mg of the sample was heated in air to ~500'C, e.g., to remove moisture and any hydrocarbon or coke impurities. For 2,2-DMB adsorption, the sample was cooled to ~120° C. after the air calcination step and then exposed to a flow of ~60 torr (~8 kPag) of 2,2-DMB in nitrogen.

Mesitylene Sorption:

Mesitlylene sorption may be determined as described in U.S. Pat. No. 5,240,892. One method for measuring the diffusion characteristics, such as crystal surface area, of a porous crystalline silicate is by determination of its capability for sorbing mesitylene. Such sorption is carried out under static conditions at room temperature under pressure for such time as necessary to effect equilibrium, e.g., a temperature of ~72° F. a pressure of ~0.5 mm Hg, for about 6 hours. The procedure is further described by Wu et al, "New Developments in Zeolite Science Technology", Proceeding of the 7th International Zeolite Conference, Tokyo, Japan, pp. 547-554 and G. R. Landolt, Anal. Chem. (1971) 43, 613, both of which are incorporated herein by reference.

The mesitylene uptake and sorption rate was measured placing a weighted sample of the calcined molecular sieve in contacting with vapor mesitylene at a mesitylene partial pressure of ~0.27 kPaa (~2 torr) at ~100° C. The partial pressure was kept constant by continuously flowing vapor mesitylene to the adsorption chamber. The increase of weight was measured with time on stream. The equilibrium amount of mesitylene uptake and rate of update were calculated as described in "Principles and Practice of Heterogeneous Catalysis", eds. J. M. Thomas, and W. J. Thomas, First Edition, 1997.

Collidine Number Measurement

The collidine number of a molecular sieve may be measured by thermogravimetric analysis (TGA). Samples can be dried at ~200° C. to constant weight (weight change less than ±1% for the period of 1 hour). The weight of the dried sample, the sorbate, can then be measured. The sorbent, 2,4,6-collidine, can be delivered by a sparger maintained at ~3 torr collidine partial pressure and carried over the sample by nitrogen passed at ~200 ml/min for ~60 min. The collidine number is expressed as micromoles of adsorbed per gram of the sorbate.

n-Hexane Sorption:

n-Hexane sorption may be determined as described in U.S. Pat. No. 6,613,951. Micropore volume (n-hexane) measurements were made on a computer controlled (Vista/Fortran) duPont 951™ Thermalgravimetric analyzer. Isotherms were measured at ~90° C. and adsorption values taken at ~75 torr n-hexane. The diffusion measurements were made on a TA Instruments 2950™ Thermalgravimetric Analyzer equipped with a Thermal Analysis 2000 controller, a gas switching accessory and an automatic sample changer. Diffusion measurements were made at ~120° C. and ~60 torr 2,2-dimethylbutane and data were plotted as uptake versus square root of time.

Alpha Test:

The alpha value test is a measure of the cracking activity of a catalyst and is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that.

TABLE 1

Comparison of structural and hexane cracking properties of alumina bound and organosilica bound ZSM-48.

| | Comparative Sample A- Steamed 65% ZSM-48 w/V300 Quadralobes | Sample A- 65% $NH_4NO_3$ ZSM-48 Cylinders | Sample B- Steamed 65% $NH_4NO_3$ ZSM-48 Cylinders |
|---|---|---|---|
| Alpha | 60-80 | 55 | 64 |
| Micropore Vol. (cc/gm) | 0.023 | 0.095 | |
| Mesitylene Sorption (mg/gm) | 25 | 43 | 32 |
| Mesitylene Diffusivity (D/r2) | 3.000 | 5,400 | 25,900 |
| Collidine Adsorption (μmoles/gm) | 49.5 | 46 | 30 |
| n-Hexane Sorption (mg/gm) | 30 | 59 | 43 |
| Surface Area ($m_2$/gm) | 250 | 645 | 440 |
| 23DMB Sorption (mg/gm) | 8 | 31 | |
| 23DMB Diffusivity (mg/gm) | 183,300 | 880,000 | |
| Pore Size Distribution (nm) | 7.2-9.0 | 5.3 | |
| Pore Volume (cc/gm) | 0.42-0.53 | 0.66 | |
| Micropore Surface Area ($m^2$/gm) | 45-60 | 204 | |

TABLE 2

Comparison of structural and hexane cracking properties of alumina bound and organosilica bound ZSM-48 crosslinked with HCl and NH₄NO₃.

| | Comparative Sample A-Steamed 65% ZSM-48 w/V300 Quadralobes | Sample A-65% ZSM-48 NH₄NO₃ Cylinders | Sample C-68% ZSM-48 HCl Cylinders | Sample D-86% ZSM-48 Cylinders |
|---|---|---|---|---|
| Alpha | 60-80 | 55 | 59 | 66 |
| Micropore Vol. (cc/gm) | 0.023 | 0.095 | 0.054 | 0.043 |
| Mesitylene Sorption (mg/gm) | 25 | 43 | 30 | 30 |
| Mesitylene Diffusivity (D/r2) | 3,000 | 5,400 | | 4,300 |
| Collidine Adsorption (μmoles/gm) | 49.5 | 46 | 48 | 63 |
| n-Hexane Sorption (mg/gm) | 30 | 59 | 54 | 51 |
| Surface Area (m²/gm) | 250 | 645 | 408 | 440 |
| 23DMB Sorption (mg/gm) | 8 | 31 | 20 | 30 |
| 23DMB Diffusivity (mg/gm) | 183,300 | 880,000 | 641,300 | 83,400 |
| Pore Size Distribution (nm) | 7.2-9.0 | 5.3 | 6.7 | 7.3 |
| Pore Volume (cc/gm) | 0.42-0.53 | 0.66 | 0.53 | 0.60 |
| Micropore Surface Area (m²/gm) | 45-60 | 204 | 124 | 99 |

TABLE 3

Comparison of structural and hexane cracking properties of alumina bound and organosilica bound ZSM-48 crosslinked with HCl and NH₄NO₃.

| | Sample E-Steamed 86% ZSM-48 Cylinders | Sample A-65% ZSM-48 NH₄NO₃ Cylinders | Sample B-Steamed 65% ZSM-48 Cylinders | Comparative Sample A-Steamed 65% ZSM-48 w/V300 Quadralobes | Sample F-8% ZSM-5 (steamed) Cylinders |
|---|---|---|---|---|---|
| Alpha | 88 | 55 | 64 | 60-80 | 150 |
| Micropore Vol. (cc/gm) | 0.03 | 0.095 | | 0.023 | |
| Mesitylene Sorp. (mg/gm) | 17 | 43 | 32 | 25 | 60 |
| Mesitylene Diffusiv. (D/r²) | 19,600 | 5,400 | 25,900 | 3,000 | 4,500 |
| Collidine Sorp. (μmoles/gm) | 42 | 46 | 30 | 49.5 | 55 |
| n-Hexane Sorp. (mg/gm) | 35 | 59 | 43 | 30 | 106 |
| Surface Area (m²/gm) | | 645 | 440 | 250 | 540 |
| 23DMB Sorp. (mg/gm) | 20 | 31 | | 8 | 59 |
| 23DMB Diffus. (mg/gm) | 743,600 | 880,000 | | 183,300 | 173,900 |
| Pore Size Distrib. (nm) | | 5.3 | | 7.2-9.0 | |
| Pore Vol. (cc/gm) | | 0.66 | | 0.42-0.53 | |
| Micropore SA (m²/gm) | | 204 | | 45-60 | |

What is claimed is:

1. A catalyst comprising:

(i) at least one microporous material, wherein the microporous material is a zeolite, a molecular sieve comprising aluminophosphate and/or silicoaluminophosphate, or combinations thereof;

(ii) a porous organosilica material binder, which is a polymer comprising independent units of a monomer selected from the group consisting of:

(a) a monomer of Formula $[Z^{15}Z^{16}SiCH2]3$ (I), wherein each $Z^{15}$ represents a hydroxyl group, a C1-C4 alkoxy group or an oxygen atom bonded to a silicon atom of another monomer and each $Z^{16}$ represents a hydroxyl group, a C1-C4 alkoxy group, a C1-C4 alkyl group, or an oxygen atom bonded to a silicon atom of another monomer; and (b) a cyclic polyurea monomer of Formula

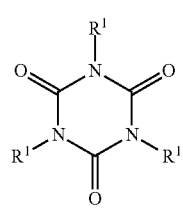

(II)

wherein each $R^1$ independently is a $X^5OX^6X^7SiX^8$ group, wherein each $X^5$ represents a hydrogen atom, a C1-C4 alkyl group, or a bond to a silicon atom of another monomer unit; $X^6$ and $X^7$ each independently represent a hydroxyl group, a C1-C4 alkyl group, a C1-C4 alkoxy group, or an oxygen atom bonded to a silicon atom of another monomer unit; and each $X^8$ represents a C1-C8 alkylene group bonded to a nitrogen atom of the cyclic polyurea; and (iii) at least one catalyst metal, wherein the at least one catalyst metal is incorporated into the microporous material, the porous organosilica material binder and/or a catalyst particle comprising the at least one microporous material bound with the polymer, and the porous organosilica material binder is present in the catalyst in an amount of at least about 1.0 wt % based on the total weight of the microporous material and the porous organosilica material binder.

2. The catalyst of claim 1, wherein the independent units of the polymer include a monomer of Formula (I), each $Z^{15}$ represents a hydroxyl group, a C1-C2 alkoxy group, or an oxygen atom bonded to a silicon atom of another siloxane unit and each $Z^{16}$ represent a hydroxyl group, a C1-C2 alkyl group, a C1-C2 alkoxy group, or an oxygen atom bonded to a silicon atom of another siloxane unit.

3. The catalyst of claim 1, wherein the independent units of the polymer include a monomer of Formula (I), each $Z^{15}$ represents a hydroxyl group, ethoxy, or an oxygen atom bonded to a silicon atom of another siloxane and each $Z^{16}$ represent a hydroxyl group, ethoxy, or an oxygen atom bonded to a silicon atom of another siloxane.

4. The catalyst of claim 1, wherein the independent units of the polymer include a monomer of Formula (I), each $X^5$ represents a hydrogen atom, a C1-C2 alkyl group or a bond to a silicon atom of another monomer unit; $X^6$ and $X^7$ each independently represent a hydroxyl group, a C1-C2 alkyl group, a C1-C2 alkoxy group or an oxygen atom bonded to a silicon atom of another monomer unit and $X^8$ represents a C1-C4 alkylene group bonded to a nitrogen atom of the cyclic polyurea.

5. The catalyst of claim 1, wherein the independent units of the polymer include a monomer of Formula (I), each $X^5$ represents a hydrogen atom, methyl or a bond to a silicon atom of another monomer unit; $X^6$ and $X^7$ each independently represent a hydroxyl group, methoxy or an oxygen atom bonded to a silicon atom of another monomer unit and $X^8$ represents —CH2CH2CH2—bonded to a nitrogen atom of the cyclic polyurea.

6. The catalyst of claim 1, wherein the porous organosilica material binder further comprises at least one other monomer selected from the group consisting of:
(i) at least one independent unit of Formula [$Z^3OZ^4SiCH2$]3 (III), wherein each $Z^3$ represents a hydrogen atom, a C1-C4 alkyl group or a bond to a silicon atom of another monomer and $Z^4$ represents a C1-C6 alkyl group;
(ii) at least one independent unit of Formula $Z^5OZ^6Z^7Z^8Si$ (IV), wherein each $Z^5$ represents a hydrogen atom or a C1-C4 alkyl group or a bond to a silicon atom of another monomer; and $Z^6$, $Z^7$ and $Z^8$ are each independently selected from the group consisting of a hydroxyl group, a C1-C4 alkyl group, a C1-C4 alkoxy group, a nitrogen-containing C1-C10 alkyl group, a nitrogen-containing heteroalkyl group, a nitrogen-containing optionally substituted heterocycloalkyl group and an oxygen atom bonded to a silicon atom of another monomer;
(iii) at least one independent unit of Formula $Z^9Z^{10}Z^{11}Si$-R-Si$z^9z^{10}Z^{11}$ (V), wherein each $Z^9$ independently represents a hydroxyl group, a C1-C4 alkoxy group or an oxygen bonded to a silicon atom of another monomer; $Z^{10}$ and $Z^{11}$ each independently represent a hydroxyl group, a C1-C4 alkoxy group, a C1-C4 alkyl group or an oxygen atom bonded to a silicon atom of another monomer; and R is selected from the group consisting a C1-C8 alkylene group, a C2-C8 alkenylene group, a C2-C8 alkynylene group, a nitrogen-containing C1-C10 alkylene group, an optionally substituted C6-C20 aralkyl and an optionally substituted C4-C20 heterocycloalkyl group;
(iv) at least one independent unit of Formula $M^1(OZ^{12})3$ (VI), wherein $M^1$ represents a Group 13 metal and each $Z^{12}$ independently represents a hydrogen atom, a C1-C6 alkyl or a bond to a silicon atom of another monomer;
(v) at least one independent unit of Formula $(Z^{13}O)2M^2$-O—Si$(OZ^{14})3$ (VII), wherein $M^2$ represents a Group 13 metal and $Z^{13}$ and $Z^{14}$ each independently represent a hydrogen atom, a C1-C6 alkyl group or a bond to a silicon atom of another monomer; and
(vi) a combination thereof.

7. The catalyst of claim 6, wherein at least one independent unit of Formula (III) is present, wherein each $Z^3$ represents a hydrogen atom, a C1-C2 alkyl group or a bond to a silicon atom of another siloxane monomer and each $Z^4$ represents a C1-C2 alkyl group.

8. The catalyst of claim 7, wherein each $Z^3$ represents a hydrogen atom, ethyl or a bond to a silicon atom of another siloxane monomer and each $Z^4$ represents a methyl.

9. The catalyst of claim 6, wherein at least one independent unit of Formula (IV) is present, wherein each $Z^5$ represents a hydrogen atom, a C1-C2 alkyl group or a bond to a silicon atom of another monomer; and $Z^6$, $Z^7$ and $Z^8$ are each independently selected from the group consisting of a hydroxyl group, a C1-C2 alkyl group, C1-C2 alkoxy group, a nitrogen-containing C3-C10 alkyl group, a nitrogen-containing C4-C10 heteroalkyl group, a nitrogen-containing optionally substituted C4-C10 heterocycloalkyl group and an oxygen bonded to a silicon atom of another monomer.

10. The catalyst of claim 9, wherein $Z^6$, $Z^7$ and $Z^8$ are each independently selected from the group consisting of a hydroxyl group, a C1-C2 alkyl group, C1-C2 alkoxy group, and an oxygen bonded to a silicon atom of another monomer.

11. The catalyst of claim 9, wherein each $Z^5$ represents a hydrogen atom, methyl, ethyl, or a bond to a silicon atom of another monomer; and $Z^6$, $Z^7$ and $Z^8$ are each independently selected from the group consisting of a hydroxyl group, methyl, methoxy, ethoxy,

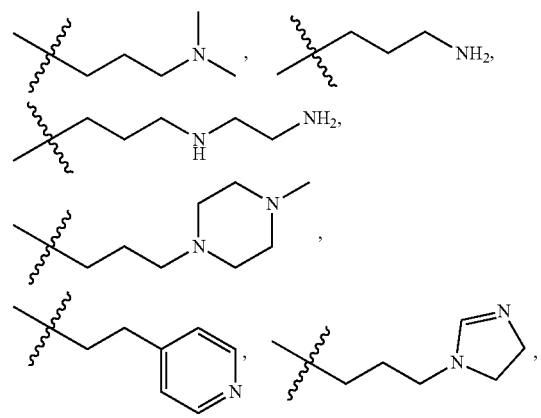

and an oxygen bonded to a silicon atom of another monomer.

12. The catalyst of claim 6, wherein at least one independent unit of Formula (V) is present, wherein each $Z^9$ represents a hydroxyl group, a C1-C2 alkoxy group or an oxygen bonded to a silicon atom of another monomer; $Z^{10}$ and $Z^{11}$ each independently represent a hydroxyl group, a C1-C2 alkoxy group, a C1-C2 alkyl group or an oxygen bonded to a silicon atom of another monomer; and R is selected from the group consisting of a C1-C4 alkylene group, a C2-C4 alkenylene group, a C2-C4 alkynylene group, a nitrogen-containing C4-C10 alkylene group, an optionally substituted C6-C10 aralkyl and an optionally substituted C4-C12 heterocycloalkyl group.

13. The catalyst of claim 12, wherein each $Z^9$ represents a hydroxyl group, methoxy, ethoxy or an oxygen bonded to a silicon atom of another monomer; $Z^{10}$ and $Z^{11}$ each independently represent a hydroxyl group, methoxy, ethoxy, methyl or an oxygen bonded to a silicon atom of another monomer; and R is selected from the group consisting of —CH2—, —CH2CH2—, —HC═CH—,

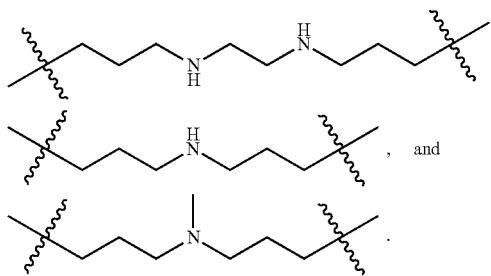

, and

14. The catalyst of claim 6, wherein at least one independent unit of Formula (VI) is present, wherein $M^1$ is Al or B and each $Z^{12}$ represents a hydrogen atom, a C1-C4 alkyl group or a bond to a silicon atom or another monomer.

15. The catalyst of claim 6, wherein at least one unit of Formula (VII) is present, wherein $M^2$ is Al or B and $Z^{13}$ and $Z^{14}$ each independently represent a hydrogen atom, a C1-C4 alkyl group or a bond to a silicon atom of another monomer.

16. The catalyst of claim 1, wherein the porous organosilica material binder is present in the catalyst in an amount of about 5.0 wt % to about 99 wt %.

17. The catalyst of claim 1, wherein the microporous material is present in the catalyst in an amount of at most about 95.0 wt %.

18. The catalyst of claim 1, wherein the at least one catalyst metal is selected from the group consisting of a Group 8 metal, a Group 9 metal, a Group 10 metal and a combination thereof.

19. The catalyst of claim 1, wherein the at least one catalyst metal is selected from the group consisting of Pt, Pd, Ir, Rh, Re, Ru, Os and a combination thereof.

20. The catalyst of claim 19, wherein the at least one catalyst metal is selected from the group consisting of Pt, Pd, and a mixture thereof.

21. The catalyst of claim 1, wherein the at least one microporous material is selected from the group consisting of a zeolite, a SAPO, an ALPO and a combination thereof.

22. The catalyst of claim 1, wherein the at least one microporous material is selected from the group consisting of ZSM-5, ZSM-11, ZSM-22, ZSM-23, ZSM-35, ZSM-48, ZSM-50, ZSM-57, MCM-49, MCM-22, SAPO-11, SAPO-41, AlPO-11, AlPO-H2, and AlPO-41.

23. The method of claim 1, wherein the catalyst has a pore volume of about 0.3 cm³/g to about 1.0 cm³/g.

24. The method of claim 1, wherein the catalyst has a total surface area of about 300 m²/g to about 1500 m²/g.

* * * * *